(12) United States Patent
Klassen et al.

(10) Patent No.: US 10,041,041 B2
(45) Date of Patent: Aug. 7, 2018

(54) COMPOSITIONS AND METHODS FOR TREATING RETINAL DISEASES

(71) Applicant: THE REGENTS OF THE UNIVERSITY OF CALIFORNIA, Oakland, CA (US)

(72) Inventors: Henry Klassen, Irvine, CA (US); Jing Yang, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/715,464

(22) Filed: May 18, 2015

(65) Prior Publication Data
US 2015/0328262 A1 Nov. 19, 2015

Related U.S. Application Data

(62) Division of application No. 14/118,223, filed as application No. PCT/US2012/038342 on May 17, 2012, now Pat. No. 9,107,897.

(60) Provisional application No. 61/487,419, filed on May 18, 2011.

(51) Int. Cl.
*A61K 35/30* (2015.01)
*C12N 5/079* (2010.01)
*A61K 9/00* (2006.01)
*C12N 5/0797* (2010.01)

(52) U.S. Cl.
CPC .......... *C12N 5/0621* (2013.01); *A61K 9/0019* (2013.01); *A61K 9/0048* (2013.01); *A61K 35/30* (2013.01); *C12N 5/0623* (2013.01); *C12N 2500/02* (2013.01); *C12N 2500/38* (2013.01);

(Continued)

(58) Field of Classification Search
None
See application file for complete search history.

(56) References Cited

U.S. PATENT DOCUMENTS 7,514,259 B2 4/2009 Young et al.
8,241,897 B2 8/2012 Klassen et al.
(Continued)

FOREIGN PATENT DOCUMENTS

EP 2279247 A4 8/2012
WO 02076386 A3 10/2002
(Continued)

OTHER PUBLICATIONS

Klassen et al, "Multipotent retinal progenitors express developmental markers, differentiate into retinal neurons, and preserve light-mediated behavior" Investigative Ophthalmology & Visual Science, 2004, v 45, p. 4167-4173.

(Continued)

*Primary Examiner* — David W Berke-Schlessel
(74) *Attorney, Agent, or Firm* — Greer, Burns & Crain; Gregory P. Einhorn

(57) ABSTRACT

Disclosed herein are compositions and methods for treating, ameliorating or preventing a retinal disease or condition; improving a photopic (day light) vision; for improving correcting visual acuity, improving macular function, improving a visual field, or improving scotopic (night) vision by administration of retinal progenitor cells. The subject matter described herein also provides cell populations comprising retinal progenitor cells and methods of isolation thereof.

10 Claims, 55 Drawing Sheets

(52) U.S. Cl.
CPC ...... *C12N 2500/90* (2013.01); *C12N 2509/00* (2013.01); *C12N 2533/52* (2013.01)

(56) References Cited

U.S. PATENT DOCUMENTS

| | | |
|---|---|---|
| 9,730,962 B2 | 8/2017 | Klimanskaya et al. |
| 2008/0213893 A1 | 9/2008 | Klassen et al. |

FOREIGN PATENT DOCUMENTS

| | | |
|---|---|---|
| WO | 2007100692 A3 | 9/2007 |
| WO | 2007130060 A3 | 11/2007 |

OTHER PUBLICATIONS

Ahmad et al, "In vitro analysis of a mammalian retinal progenitor that gives rise to neurons and glia" Brain Research, 1999, v 831, p. 1-10.

Wang et al, "Isolation, culture and differentiation of the human fetal retinal progenitor cells" IOVS, 2005, v 46, p. 3243.

Yang et al, "Aqueous humor enhances the proliferation of rat retinal precursor cells in culture, and this effect is partially reproduced by ascorbic acid" Stem Cells, 2006, v 24, p. 2766-2775.

Ezashi et al, "Low O2 tensions and the prevention of differentiation of hES cells" Proceedings of the National Academy of Sciences, 2005, v 102, p. 4783-4788.

Lamba et al, "Efficient generation of retinal progenitor cells from human embryonic stem cells" Proceedings of the National Academy of Science, 2006, v 103, p. 12769-12774.

Bhattacharya et al, "Direct identification and enrichment of retinal stem cells/progenitors by Hoechst Dye Efflux Assay", IOVS, 2003, v 44, n 6, p. 2764-2773.

Hee, International Search Report and Written Opinion for PCT/US2012/038342, Korean Intellectual Property Office, dated Dec. 26, 2012.

Klassen et al, "Stem cells and retinal repair" Progress in Retinal and Eye Research, 2004, v 23, n 2, p. 149-181.

Klassen et al, "Isolation of retinal progenitor cells from post-mortem human tissue and comparison with autologous brain progenitors" Journal of Neuroscience Research, 2004, v 77, n 3, p. 334-343.

Klassen et al, "Progenitor cells from the porcine neural retina express photoreceptor markers after transplantation to the subretinal space of allorecipients" Stem Cells, 2007, v 25, p. 1222-1230.

Nickitas-Etienne, International Preliminary Report on Patentability, PCT/US2012/038342, International Bureau of WIPO, dated Nov. 19, 2013.

Redenti et al, "Retinal tissue engineering using mouse retinal progenitor cells and a novel biodegradable, thin-film poly (e-caprolactone) nanowire scaffold" J. Ocul. Biol. Dis. Inform., 2008, v 1, n 1, p. 19-29.

Taranova et al, "SOX2 is a dose-dependent regulator of retinal neural progenitor competence" Genes and Development, 2006, v 20, p. 1187-1202.

Tropepe et al, "Retinal stem cells in the adult mammalian eye" Science, 2000, v 287, p. 2032-2036.

Zhou, Third Office Action for Chinese Patent Application 201280035828.X, State Intellectual Property Office of China, dated Mar. 2, 2016.

Zhou, Second Office Action for Chinese Patent Application 201280035828.X, State Intellectual Property Office of China, dated Aug. 25, 2015.

Armandola, Extended European Search Report for European Patent Application EP 12785466, European Patent Office, dated Nov. 28, 2014.

Klassen, Henry, et al., "Isolation of Retinal Progenitor Cells From Post-Mortem Human Tissue and Comparison With Autologous Brain Progenitors", Journal of Neuroscience Research, vol. 77, (2004), pp. 334-343.

Klassen, Henry, et al., "Multipotent Retinal Progenitors Express Developmental Markers, Differentiate into Retinal Neurons, and Preserve Light-Mediated Behavior", Investigative Ophthalmology & Visual Science, vol. 45, No. 11, Nov. 2004, pp. 4167-4173.

Klassen, Henry, et al., "Neural precursors isolated from the developing cat brain show retinal integration following transplantation to the retina of the dystrophic cat", Veterinary Ophthalmology, vol. 10, No. 4, (2007), pp. 245-253.

Klassen, Henry, et al., "Progenitor Cells from the Porcine Neural Retina Express Photoreceptor Markers After Transplantation to the Subretinal Space of Allorecipients", Stem Cells, vol. 25, (2007), pp. 1222-1230 www.StemCells.com.

Klassen, Henry, et al., "Photoreceptor Differentiation following Transplantation of Allogeneic Retinal Progenitor Cells to the Dystrophic Rhodopsin Pro347Leu Transgenic Pig", Stem Cells International, vol. 2012, Article ID 939801, 9 pages.

Lamba, Deepak, A., et. al. "Transplantation of Human Embryonic Stem Cell-Derived Photoreceptors Restores Some Visual Function in Crx-Deficient Mice", Cell Stem Cell, vol. 4, Jan. 9, 2009, pp. 73-79.

Maclaren, R.E., et al., "Retinal repair by transplantation of photoreceptor precursors", Nature, vol. 444, Nov. 9, 2006, pp. 203-207.

Takahashi, Masayo, et al., "Widespread Integration and Survival of Adult-Derived Neural Progenitor Cells in the Developing Optic Retina", Molecular and Cellular Neuroscience, vol. 12, (1998), pp. 340-348.

Warfvinge, Karin, et al., "Xenotransplantation of Human Neural Progenitor Cells to the Subretinal Space of Nonimmunosuppressed Pigs", Journal of Transplantation, vol. 2011, Article ID 948740, 6 pages.

You, X. Joanne, et al., "Feline Neural Progenitor Cells II: Use of Novel Plasmid Vector and Hybrid Promoter to Drive Expression of Glial Cell Line-Derived Neurotrophic Factor Transgene", Stem Cells International, vol. 2012, Article ID 604982, 9 pages.

Young, Michael, J., et al., "Neuronal Differentiation and Morphological Integration of Hippocampal Progenitor Cells Transplanted to the Retina of Immature and Mature Dystrophic Rats", Molecular and Cellular Neuroscience, vol. 16, (2000), pp. 197-205.

Yupin Cai, First Office Action for CN 2015107452076 dated Feb. 5, 2018.

Schmitt et al., "Molecular Characterization of Human Retinal Progenitor Cells" IOVS, Dec. 2009, v 50, n 12, p. 5901-5908.

Mohyeldin A. et al., Oxygen in Stem Cell Biology: A Critical Component of the Stem Cell Niche. Cell Stem Cell, Aug. 6, 2010, vol. 7, No. 2, pp. 150-161.

Santilli G. et al., Mild hypoxia enhances proliferation and multipotency of human neural stem cells. PLoS One, Jan. 5, 2010, vol. 5, No. 1, pp. e8575.

Yang J. et al., Aqueous humor enhances the proliferation of rat retinal precursor cells in culture, and this effect is partially reproduced by ascorbic acid. Stem cells, Aug. 10, 2006, vol. 24, No. 12, pp. 2766-2775.

OH, Search Report and Written Opinion for SG 10201603773U dated Sep. 28, 2017.

Klassen et al., "Surface markers expressed by multipotent human and mouse neural progenitor cells include tetraspanins and non-protein epitopes." Neuroscience Letters, 2001, v 312, p. 180-182.

Aftab et al., "Growth kinetics and transplantation of human retinal progenitor cells." Experimental Eye Research, 2009, v 89, p. 301-310.

Klassen et al., "The immunological properties of adult hippocampal progenitor cells." Vision Research, 2003, v 43, p. 947-956.

Office Action for Japanese Patent Application JP 2016-517910 dated Oct. 20, 2017.

Armandola, Examination Report for EP 12785466.9 dated Feb. 6, 2018.

Temple, Office Action for Canadian Patent Application 2,835,215 dated Apr. 5, 2018.

A
Advanced DMEM/F12 vs. DMEM/F12
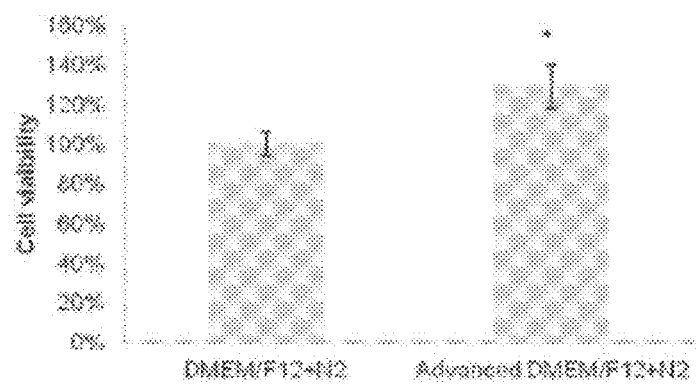
B
Medium supplements
N2 vs. B27 (Xeno-Free)
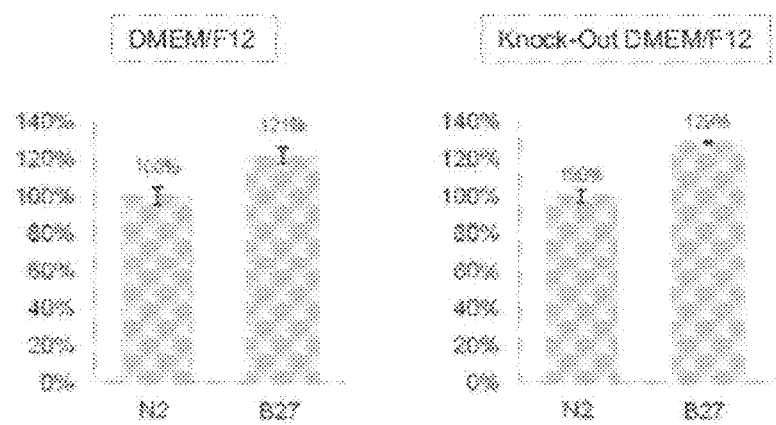
FIGURE 6

A
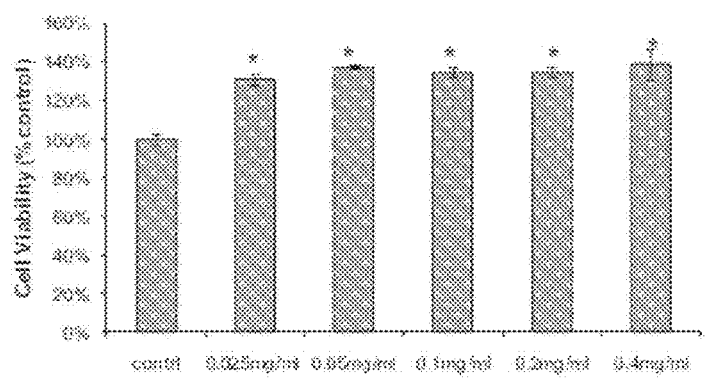
B 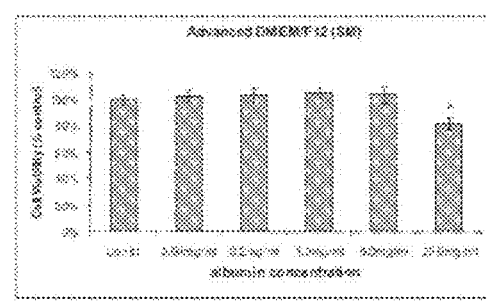 C 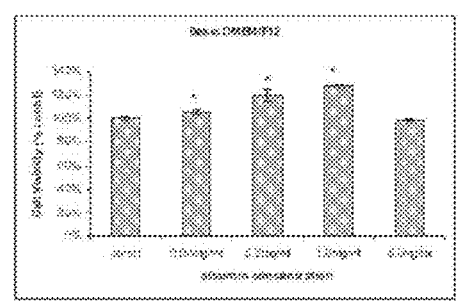
FIGURE 7

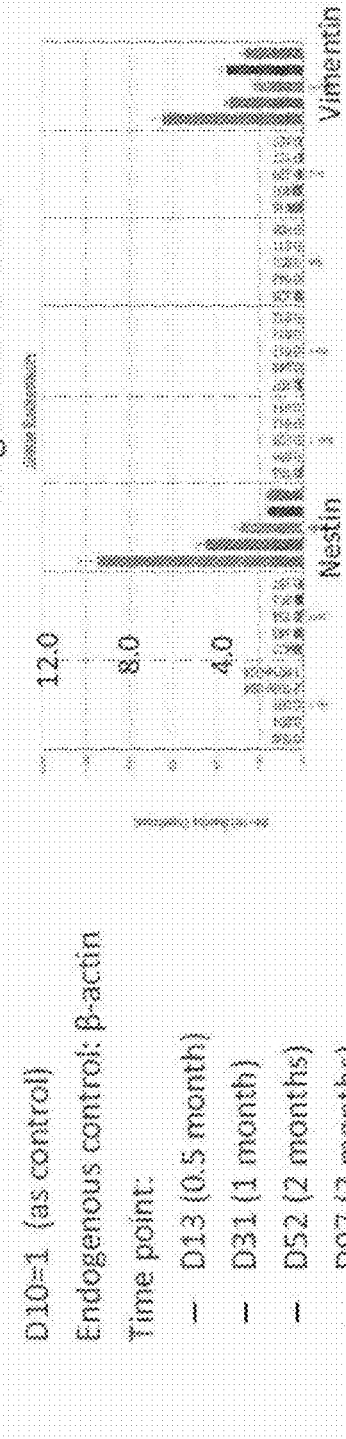
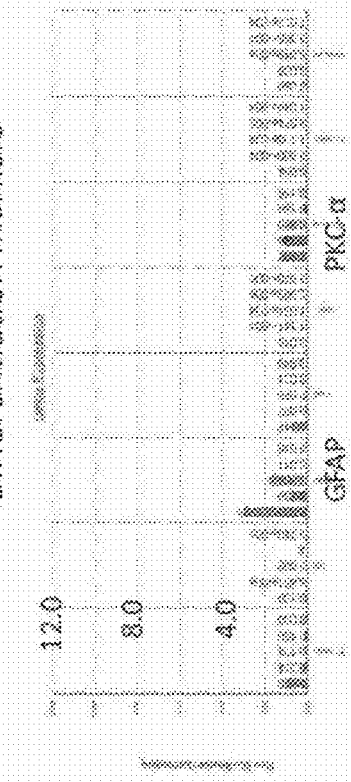
FIGURE 15

Top 10 genes up-regulated >10 fold
(hRPC vs h-fibroblast=1)

| | 070809hRPC | 073109hRPC | 011310hRPC |
|---|---|---|---|
| 1 | AQP4 | AQP4 | |
| 2 | CD133 | CD133 | |
| 3 | GFAP | GFAP | GFAP |
| 4 *** (down) | Klf4 | Klf4 | Klf4 |
| 5 | Map2 | Map2 | Map2 |
| 6 | Mash1 | Mash1 | |
| 7 | Nestin | Nestin | Nestin |
| 8 | Notch1 | Notch1 | |
| 9 | Recoverin | Recoverin | Recoverin |
| 10 | six6 | six6 | six6 |
| 11 | sox2 | sox2 | sox2 |

FIGURE 22

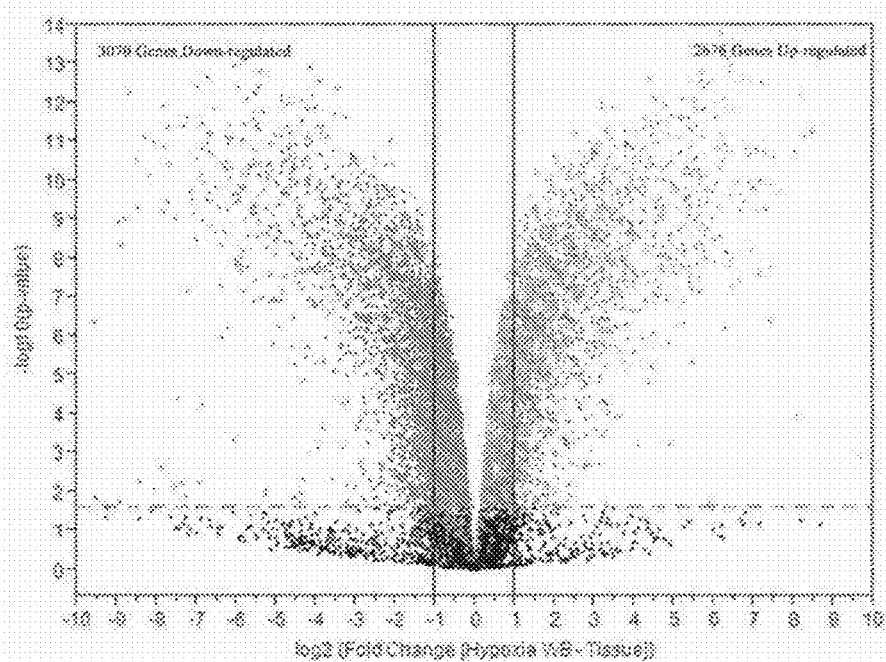
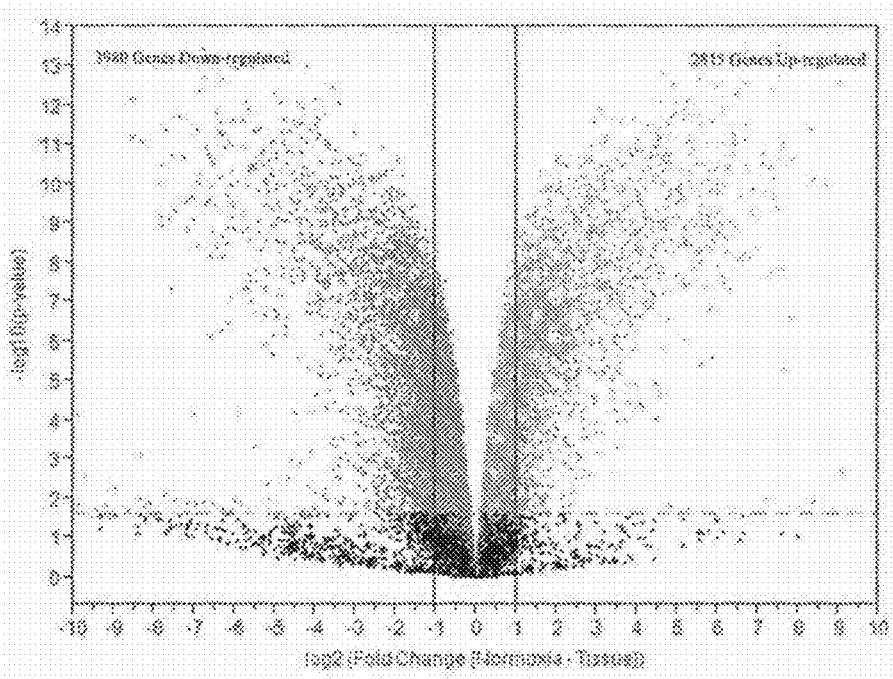
FIGURE 38 cRPC time point design

FIGURE 40

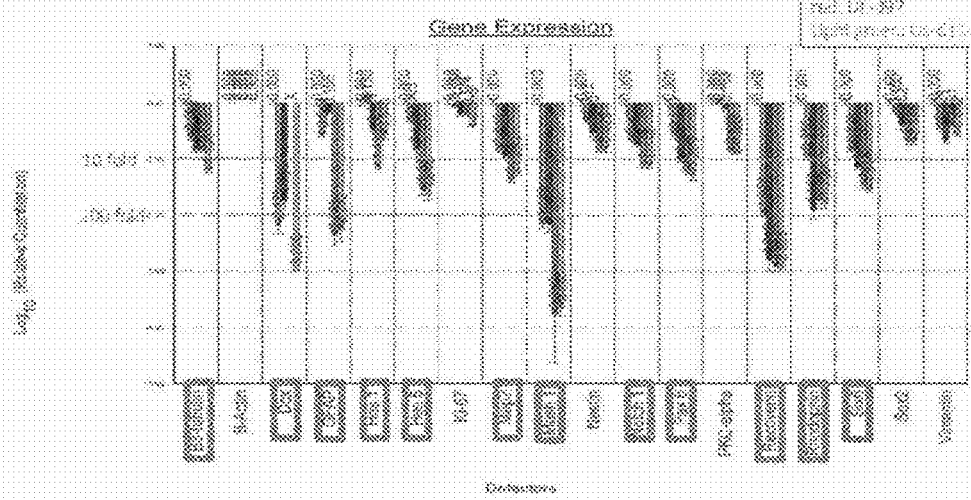
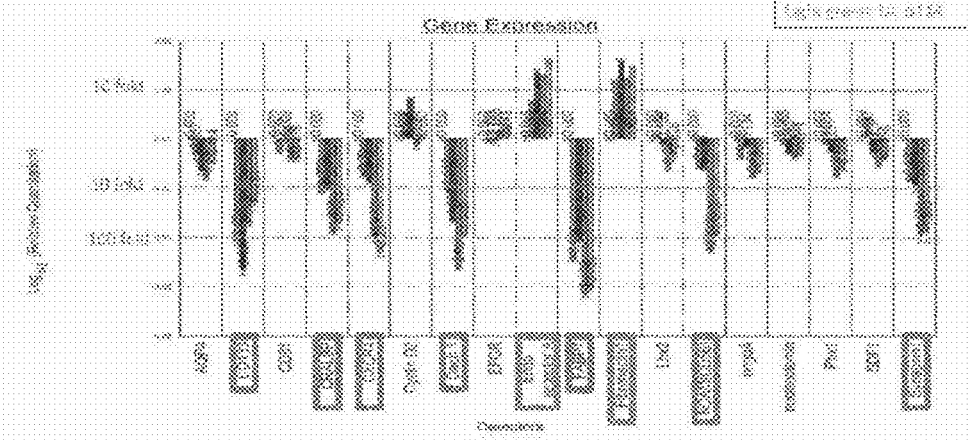
FIGURE 42

|  | retina | cultured hRPC | | |
|---|---|---|---|---|
|  | retina tissue | Normoxia hRPC | Hypoxia hRPC | ICC confirmed |
| Nestin | 86% | 99% | 99% | 95% |
| Sox2 | 70% | 90-99% | 90-99% | 90% |
| Ki67 |  |  |  | 40-50% |
| GFAP | 0.5% | 5-10% | 5-10% | 5% |
| MHC I | 2% | 90% | 90% |  |
| MHC II | 0% | 1-3% | 0-1% |  |
| FAS (CD95) | 0% | 40-60% | 40-60% |  |
| CXCR4 | 80% | 5-30% | 90% |  |
| CD15 | 4-8% | 4-8% | 15-35% | 12% |
| GD2 | 2% | 2-4% | 15% | 6% |

FIGURE 48

Red: Rod opsin; Green: M-cone opsin; Blue: PNA (M-&S-cone sheaths)

COMPOSITIONS AND METHODS FOR TREATING RETINAL DISEASES

CROSS-REFERENCE TO RELATED APPLICATIONS

This United States utility patent application is a divisional of U.S. utility patent application Ser. No. 14/118,223, filed Feb. 18, 2014 (now pending), which is a § 371 national phase of PCT international patent application no. PCT/US2012/038342, having an international filing date of May 17, 2012, which claims benefit of priority to U.S. Provisional Patent Application Ser. No. 61/487,419, filed May 18, 2011. The aforementioned applications are expressly incorporated herein by reference in their entirety and for all purposes.

TECHNICAL FIELD

The subject matter described herein relates generally to the fields of stem cell biology and regenerative medicine. In particular, the subject matter disclosed herein provides compositions and methods for treating, ameliorating or preventing a retinal disease or condition; improving a photopic (day light) vision; improving or correcting visual acuity, improving macular function, improving a visual field, or improving scotopic (night) vision by administration of retinal progenitor cells. The subject matter described herein also provides cell populations comprising retinal progenitor cells and methods of isolation thereof. In alternative embodiments, provided herein are compositions and methods for treating, ameliorating or preventing a retinal disease or condition, e.g., an Usher's disease, retinitis pigmentosa (RP), a degenerative retinal disease, an age related macular degeneration (AMD), a wet AMD or a dry AMD, geographic atrophy, a retinal photoreceptor disease, a diabetic retinopathy, cystoid macular edema, uveitis, a retinal detachment, a retinal injury, macular holes, macular telangiectasia, a traumatic or an iatrogenic retinal injury, a ganglion cell or optic nerve cell disease, a glaucoma or an optic neuropathy, an ischemic retinal disease such as retinopathy of prematurity, retinal vascular occlusion, or ischemic optic neuropathy; or improving a photopic (day light) vision; or for improving correcting visual acuity, or improving macular function, or improving a visual field, or improving scotopic (night) vision. In alternative embodiments, provided herein are heterogeneous mixtures of fetal neural retinal cells and methods and compositions (e.g., kits, formulations and the like) for making and using them.

BACKGROUND

Retinal degenerations are a heterogeneous group of eye diseases that result in the permanent loss of vision and affect millions of individuals worldwide. Although the molecular mechanisms underlying these conditions vary, they share a common endpoint: the irreversible death of the photoreceptor cells. No effective treatment is currently available to restore lost photoreceptors and visual function and most therapeutic interventions can at best only slow down the disease progression.

Prior clinical studies in patients with retinal degeneration have involved the use of fetal retinal sheet transplants. This transplantation strategy relies on the immature retinal sheet extending cell processes and forming synaptic connections with the degenerate host retina. The rationale behind this is that the inner retinal neurons of the host remain intact and therefore only require synaptic connections with photoreceptors for visual function to be restored. Studies investigating retinal sheet transplantation in patients have shown some subjective visual improvement, however graft rejection, tissue availability, and unreliable clinical efficacy have prevented this approach from becoming a viable treatment option.

Stem cells and other pluripotent cells have also been contemplated for use in treating patients with retinal degenerations and can be isolated from a number of sources including embryonic tissue, adult brain, genetically manipulated dermal fibroblasts and even the retina. However, embryonic or stem cells have so far shown little ability to differentiate into retinal phenotypes when transplanted into the adult retina unless first pre-differentiated into fetal-like retinal progenitor populations. Moreover, the yields and efficiency of engraftment are low and contamination with residual tumor-forming pluripotent cells has been problematic. The current challenge in the field of photoreceptor cell placement involves understanding the developmental processes that guide cells towards photoreceptor differentiation, so that large numbers of these cells might be transplanted at the optimal stage with minimal risk of immune reactions or transformation of implanted cells to a tumorigenic phenotype.

SUMMARY

In alternative embodiments, provided herein are compositions and methods for treating, ameliorating or preventing a retinal disease or condition, e.g., an Usher's disease, retinitis pigmentosa (RP), a degenerative retinal disease, an age related macular degeneration (AMD), a wet AMD or a dry AMD, geographic atrophy, a retinal photoreceptor disease, a diabetic retinopathy, cystoid macular edema, uveitis, a retinal detachment, a retinal injury, macular holes, macular telangiectasia, a traumatic or an iatrogenic retinal injury, a ganglion cell or optic nerve cell disease, a glaucoma or an optic neuropathy, an ischemic retinal disease such as retinopathy of prematurity, retinal vascular occlusion, or ischemic optic neuropathy; or improving a photopic (day light) vision; or for improving correcting visual acuity, or improving macular function, or improving a visual field, or improving scotopic (night) vision. In alternative embodiments, provided herein are heterogeneous mixtures of fetal neural retinal cells and methods and compositions (e.g., kits, formulations and the like) for making and using them.

In alternative embodiments, provided herein are formulations, products of manufacture or compositions comprising a heterogeneous mixture of mammalian fetal neural retinal cells, made by a method comprising:

(a) harvesting a sample of cells comprising a plurality of mammalian fetal neural retinal cells from a mammalian fetus:

(i) at about 17 to 18 weeks gestational age, or at about 16 to 19 weeks gestational age, or 15 to 20 weeks, or 14 to 26 weeks, or at about 14, 15, 16, 17, 18, 19, 20, 21, 22, 23, 24, 25 or 26 weeks, gestational age for humans, or about 3, 4, 5, 6, 7, 8, 9, 10 or 11 weeks for non-human animals, optionally feline, canine or porcine cells, or 6 to 7 for feline or 6 to 9 for porcine cells, or (ii) at a stage after which a mammalian retina is clearly formed but before photoreceptor outer segments are fully formed and retinal vascularization substantially completed or completed, or at an analogous mammalian fetal staging, wherein optionally the sample of cells comprise human or feline or canine cells;

(b) enzymatically dissociating the harvested sample of cells to make a dissociated suspension of cells and/or and small- and medium-sized cellular clusters, wherein optionally the harvested sample of cells and/or and small cellular clusters are enzymatically dissociated using trypsin or equivalent, or TRYP-LE EXPRESS™ (TrypLE™ Express. Invitrogen-Life Technologies. Carlsbad Calif.) or equivalent; and (c) culturing the cells and/or and small cellular clusters in a sterile environment comprising serum-free media or serum-comprising media, and antibiotics and antifungals or no antibiotics or anti-fungals, for no more than about 1, 2, 3, 4, 5, 6, 7, 8, 9 or 10 or more passages, wherein optionally the cells and/or and small cellular clusters are cultured in a culture media comprising a Dulbecco's Modified Eagle Medium: Nutrient Mixture F-12™ (DMEM/F12™) media or an ADVANCED DMEM/F12™ media (Gibco-Invitrogen-Life Technologies, Carlsbad Calif.)) or an ULTRACULTURE™ media (BioWhittaker-Lonza Walkersville, Inc., Walkersville, Md.), optionally together with N2 supplement (Invitrogen) or B27 or B27 Xeno Free (Invitrogen), L-glutamine or GlutaMax (Invitrogen), and human recombinant growth factors consisting of EGF and bFGF (Invitrogen), or other growth factors, and optionally the DMEM/F12™ media is used for human cells and the ULTRACULTURE™ media is used for feline or canine cells, and optionally culturing or growing the cells under low oxygen conditions, or oxygen conditions that approximate or closely mimic oxygen levels of a developing fetal retina during gestation, or at about 2%, 2.5%, 3%, 3.5% oxygen, and optionally the media is supplemented with vitamin C, and optionally the vitamin C is added every 1 or 2 days, and optionally the vitamin C is added in an amount to have an initial concentration of about 0.1 mg/ml or 0.05 mg/ml, or between about 0.01 mg/ml to about 0.5 mg/ml), and optionally the media is supplemented with albumin, or human or feline or canine albumin, or recombinant albumin, or albumin is added in an amount to have an initial concentration of about 1.0 mg/ml), and optionally the sample of cells is screened for the presence of a pathogen, a bacteria, an endotoxin, a fungus, a mycoplasma, a virus, a hepatitis virus or an HIV virus, and optionally the sample of cells is screened for the presence of a normal karyotype, and optionally the sample of cells does not exhibit elevated telomerase activity, and optionally the sample of cells is screened for viability, optionally the sample of cells is screened for tumorigenicity.

In alternative embodiments of the formulations, products of manufacture or compositions, the method for making the heterogeneous mixture of fetal neural retinal cells further comprises:

(a) selecting fetal neural retinal cells on the basis of cell surface or genetic markers, optionally selecting the cells either before culturing (prospectively) or after culturing or both, wherein optionally the cell surface or genetic markers comprise CD15/LeX/SSEA1 and/or GD2 ganglioside; optionally CD9, CD81, CD133 or AQP4, CXCR4; or (b) selecting fetal neural retinal cells on the basis of a fetal neural retinal cell transcriptome profile, proteome profile and/or a genomic profile.

In alternative embodiments, the method for making a heterogeneous mixture of fetal neural retinal cells of the invention further comprises:

culturing the cells under conditions that cause them to proliferate at an optimal rate (or near optimal rate) and/or express a fetal neural retinal cell phenotype or transcriptome profile, wherein optionally the fetal neural retinal cell phenotype profile comprises expression of (optionally moderate) levels of Ki67, a p21, and/or a telomerase and/or high levels of one or more stem cell markers associated with a multipotent but not a pluripotent cell, or optionally the fetal neural retinal cell phenotype profile comprises (gene or message) expression of a nestin, a vimentin, a Ki-67, a differentiation marker, a beta 3-tubulin, a glial fibrillary acidic protein (GFAP) and/or a rhodopsin, or any combination thereof;

and optionally Dach1, Lhx2 and/or Pax6 messages are measured.

In alternative embodiments, the formulation, product of manufacture or composition is formulated for injection, or injection into a vitreous cavity or a subretinal space.

In alternative embodiments, provided herein are methods for treating a retinal disease or condition comprising:

(a) providing a formulation, product of manufacture or composition of the invention; and (b) injecting the formulation, product of manufacture or composition of (a) into a vitreous cavity or a subretinal space, wherein optionally the vitreous cavity or subretinal space is a human or a feline or canine vitreous cavity or subretinal space, wherein optionally a standard intraocular injection procedure is used, wherein optionally the method further comprises an anterior chamber paracentesis, thereby improving the safety of the procedure, thereby treating the retinal disease or condition.

In alternative embodiments of the methods, the retinal disease or condition comprises a Usher's disease, retinitis pigmentosa (RP), a degenerative retinal disease, an age related macular degeneration (AMD), a wet AMD or a dry AMD, a retinal photoreceptor disease, a diabetic retinopathy, a retinal detachment, a retinal injury, a traumatic or an iatrogenic retinal injury, a ganglion cell or optic nerve cell disease, a glaucoma or an optic neuropathy.

In alternative embodiments, provided herein are methods for improving a photopic (day light) vision, comprising:

(a) providing a formulation, product of manufacture or composition of the invention; and (b) injecting the formulation, product of manufacture or composition of (a) into a vitreous cavity or a subretinal space, wherein optionally the vitreous cavity or subretinal space is a human or a feline or canine vitreous cavity or subretinal space, wherein optionally a standard intraocular injection procedure is used, wherein optionally the method further comprises an anterior chamber paracentesis, thereby improving the photopic (day light) vision.

In alternative embodiments, provided herein are methods for improving correcting visual acuity, or improving macular function, or improving a visual field, or improving scotopic (night) vision, comprising:

(a) providing a formulation, product of manufacture or composition of the invention; and (b) injecting the formulation, product of manufacture or composition of (a) into a vitreous cavity or a subretinal space, wherein optionally the vitreous cavity or subretinal space is a human or a feline or canine vitreous cavity or subretinal space, wherein optionally a standard intraocular injection procedure is used, wherein optionally the method further comprises an anterior chamber paracentesis, thereby correcting visual acuity, or improving macular function, or improving a visual field, or improving scotopic (night) vision.

In alternative embodiments, provided herein are methods for making a heterogeneous mixture of fetal neural retinal cells, made by a method comprising:

(a) at about 17 to 18 weeks gestational age, or at about 16 to 19 weeks gestational age, or 15 to 20 weeks, or 14 to 26 weeks, or at about 14, 15, 16, 17, 18, 19, 20, 21, 22, 23, 24, 25 or 26 weeks, gestational age for humans, or about 3, 4, 5, 6, 7, 8, 9, 10 or 11 weeks for non-human animals, optionally feline, canine or porcine cells, or 6 to 7 for feline or 6 to 9 for porcine cells, wherein optionally the sample of cells comprise human or feline or canine cells;

(b) enzymatically dissociating the harvested sample of cells to make a dissociated suspension of cells and/or and small- and medium-sized cellular clusters, wherein optionally the harvested sample of cells are enzymatically dissociated using trypsin or equivalent, or TRYP-LE EXPRESS™ (TRypLE™ Express, Invitrogen-Life Technologies, Carlsbad Calif.) or equivalent; and (c) culturing the cells in a sterile environment comprising serum-free media or serum-comprising media, and no antibiotics or anti-fungals, for no more than about 1, 2, 3, 4, 5, 6, 7, 8, 9 or 10 or more passages, wherein optionally the cells are cultured in a culture media comprising a Dulbecco's Modified Eagle Medium: Nutrient Mixture F-12™ (DMEM/F12™, media (Gibco-Invitrogen-Life Technologies. Carlsbad Calif.)) or an ULTRACULTURE media (BioWhittaker-Lonza Walkersville, Inc., Walkersville, Md.), and optionally the DMEM/F12™ media is used for human cells and the ULTRACULTURE™ media is used for feline or canine cells), and optionally the media is supplemented with vitamin C, and optionally the vitamin C is added every 1 or 2 days, and optionally the vitamin C is added in an amount to have an initial concentration of about 0.1 mg/ml or 0.05 mg/ml, or between about 0.01 mg/ml to about 0.5 mg/ml), and optionally the media is supplemented with albumin, or human or feline or canine albumin, or recombinant albumin, or albumin is added in an amount to have an initial concentration of about 1.0 mg/ml), and optionally the sample of cells is screened for the presence of a pathogen, a bacteria, an endotoxin, a fungus, a mycoplasma, a virus, a hepatitis virus or an HIV virus, and optionally the sample of cells is screened for the presence of a normal karyotype, and optionally the sample of cells does not exhibit elevated telomerase activity, and optionally the sample of cells is screened for viability, optionally the sample of cells is screened for tumorigenicity.

In alternative embodiments, provided herein are kits for treating a retinal disease or condition, or for practicing the method of the invention, comprising:

(a) a formulation, product of manufacture or composition of the invention; and/or (b) a heterogeneous mixture of fetal neural retinal cells made by the method of the invention.

In alternative embodiments, provided herein is a cell population comprising mammalian retinal progenitor cells expressing one or more markers selected from the group consisting of nestin, Sox2, Ki67, MHC Class I, and Fas/CD95, wherein nestin is expressed by greater than about 90%, or about 95-99% of the cells in the population, wherein Sox2 is expressed by greater than about 80%, or about 90-99% of the cells in the population, wherein Ki-67 is expressed by greater than about 30%, or about 40-60% of the cells in the population, wherein MHC Class I is expressed by greater than about 70%, or about 90% of the cells in the population, and wherein Fas/CD95 is expressed by greater than about 30%, or about 40-70% of the cells in the population. In some embodiments, the cells are derived from a human or non-human mammal.

In certain embodiments, the mammalian retinal progenitor cells in the population further express one or more markers selected from the group consisting of vimentin, CD9, CD81, AQP4, CXCR4, CD15/LeX/SSEA1, GD2 ganglioside, CD133, β3-tubulin MAP2, GFAP, OPN/SPP1, PTN, KDR, and TEK.

In another aspect, a method for isolating a population of mammalian retinal progenitor cells is provided, comprising harvesting mammalian fetal retinal tissue at a stage after which the retina is formed but before photoreceptor outer segments are fully formed throughout the retina and before retinal vascularization is substantially completed or completed; dissociating the harvested tissues to generate a dissociated suspension of cells and cell clusters; and culturing the dissociated suspension for about 10-30 passages, wherein the mammalian retinal progenitor cells express one or more markers selected from the group consisting of nestin, Sox2, Ki-67, β3-tubulin, MAP2, MHC Class I, and Fas/CD95, wherein nestin is expressed by greater than about 90%, or about 95-99% of the cells in the population, wherein Sox2 is expressed by greater than about 80%, or 90-99% of the cells in the population, wherein Ki-67 is expressed by greater than about 30%, or about 40-60% of the cells in the population, wherein MHC Class I is expressed by greater than about 70%, or about 90% of the cells in the population, and wherein Fas/CD95 is expressed by greater than about 30%, or about 40-70% of the cells in the population. In some embodiments, the tissues are harvested from a human or a non-human mammal. In some embodiments, the tissues are harvested from a human fetal retina at a gestational age between about 12 weeks to about 28 weeks, or from postnatal or neonatal retinal tissues. In other embodiments, the tissues are harvested from a non-human fetal retina at a gestational age between about 3 weeks to about 11 weeks. In other embodiments, the tissues are harvested from a non-human mammal at a gestational age between about 3 weeks to 11 weeks, or from postnatal or neonatal retinal tissues. The cells may be cultured at atmospheric oxygen levels or at low oxygen levels that approximate oxygen levels of a developing fetal retina during gestation, such as, e.g., between about 0.5% to about 7% and may also be cultured in serum-free or reduced serum cell culture media, which may optionally comprise additional supplements such as, for example, N2, B27, vitamin C and albumin.

In other aspects, a method for treating a retinal disease or condition in a subject in need thereof is provided, comprising administering to the subject an effective amount of a composition comprising mammalian retinal progenitor cells, wherein the mammalian retinal progenitor cells express one or more markers selected from the group consisting of nestin, Sox2, Ki-67, β3-tubulin, MAP2, MHC Class I, and Fas/CD95, wherein nestin is expressed by greater than about 90%, or about 95-99% of the cells in the population, wherein Sox2 is expressed by greater than about 80%, or about 90-99% of the cells in the population, wherein Ki-67 is expressed by greater than about 30%, or 40-60% of the cells in the population, wherein MHC Class I is expressed by greater than about 70%, or about 90% of the cells in the population, and wherein Fas/CD95 is expressed by greater than about 30%, or about 40-70% of the cells in the population, and optionally measuring changes in vision in the subject, thereby treating the retinal disease or condition.

In alternative embodiments, the subject is a human or a non-human mammal. In some embodiments, the composition is formulated for injection into a vitreous cavity or a subretinal space of the subject. The retinal disease or condition may comprise retinitis pigmentosa (RP), Leber's congenital amaurosis (LCA), Stargardt disease, Usher's syndrome, choroideremia, a rod-cone or cone-rod dystrophy, a ciliopathy, a mitochondrial disorder, progressive retinal atrophy, a degenerative retinal disease, age related macular degeneration (AMD), wet AMD, dry AMD, geographic atrophy, a familial or acquired maculopathy, a retinal photoreceptor disease, a retinal pigment epithelial-based disease, diabetic retinopathy, cystoid macular edema, uveitis, retinal detachment, traumatic retinal injury, iatrogenic retinal injury, macular holes, macular telangiectasia, a ganglion cell disease, an optic nerve cell disease, glaucoma, optic neuropathy, ischemic retinal disease, retinopathy of prematurity, retinal vascular occlusion, familial macroaneurysm, a retinal vascular disease, an ocular vascular diseases, a vascular disease, or ischemic optic neuropathy.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The following Detailed Description, given by way of example, but not intended to limit the subject matter described herein to specific embodiments described, may be understood in conjunction with the accompanying figures, incorporated herein by reference, in which:

FIG. 6 illustrates cell viability of human retinal progenitor cells (hRPCs) as a function of growth conditions: FIG. 6A shows comparison of growth conditions between Advanced DMEM/F12 containing supplemental vitamin C and albumin, and base DMEM/F12 cell culture media supplemented with N2.

FIG. 6 illustrates cell viability of human retinal progenitor cells (hRPCs) as a function of growth conditions: FIG. 6B illustrates an experiment comparing growth of hRPCs in cell culture medium supplemented with N2 or B27.

FIG. 7 illustrates cell viability of human retinal progenitor cells (hRPCs) as a function of cell culture supplementation conditions: FIG. 7A summarizes an experiment testing the effects of Vitamin C supplementation in hRPC cultures. Addition of vitamin C resulted in improved hRPC viability.

FIG. 7 illustrates cell viability of human retinal progenitor cells (hRPCs) as a function of cell culture supplementation conditions: FIGS. 7B and 7C depict an experiment testing the effects of albumin supplementation in hRPC cultures.

FIG. 11 shows the reproducibility of growth characteristics for three different cell samples used to generate a working cell bank.

FIG. 13A graphically illustrates hypoxic hRPC post-thaw cell viability; FIG. 13B graphically illustrates normoxic post-thaw cell viability; FIG. 13C graphically illustrates hypoxic and normoxic post-thaw cell viability; FIG. 13D graphically illustrates a growth curve as a function of cell numbers and passages in culture.

FIG. 15 is a graph showing a feline RPC gene profile over time using qPCR of nestin, vimentin, GFAP, and PKC-α marker transcripts.

FIG. 16B is a graph comparing feline RPC versus BPC.

FIG. 21A shows the results of qPCR (gene expression) analysis comparing expression levels of genes in hRPC versus human fibroblast (hFB). FIGS. 21B and 21C represent qPCR (gene expression) data from additional experiments.

FIG. 22 is a summary table showing a list of 11 genes (from the profile of approximately 26 used) that exhibit consistent behavior (in hRPC vs hFB) between different donations.

FIG. 28A illustrates gene expression by qPCR grown in standard proliferation medium (SM) conditions at different time points in culture; FIG. 28B illustrates gene expression by qPCR grown in SM-UL (initial UL, then SM) conditions at two different time points.

FIG. 29A illustrates gene expression by qPCR in standard proliferation medium (SM)-FBS (initial plating conditions SM+5% FBS, then changed to SM alone) conditions at different time points. FIG. 29B illustrates gene expression by qPCR with SM alone, at 2 different time points. FIG. 29C illustrates gene expression by qPCR with SM-hS (SM, after initial SM+human serum) at the same 2 time points. As previously, only GDNF is elevated.

FIGS. 38A and 38B graphically illustrate, or plot, each gene as a data point, plotted relative to fold change (up or down, X axis) and statistical significance (function of p-value, Y axis), providing an overview of how many genes are changing, how much and in which direction (up vs. down), called Volcano plots, comparing different hRPCs vs. tissue of origin.

FIG. 40 is a table summarizing time point design for feline RPCs: table of donations and treatment conditions are compared (the red underscore at UL-d76 corresponds to a clear upward inflection in growth curve for the cells, i.e., possible spontaneous immortalization).

FIGS. 41-44 show the results of an experiment measuring gene expression levels in feline RPCs by qPCR in UL media at the various time points: FIG. 41A illustrates gene expression by qPCR of feline cRPCs grown in UL medium at indicated time points. FIG. 41B includes additional markers not shown in FIG. 41A.

FIGS. 42-44 collectively represent additional data from the same experiment as shown in FIG. 41.

FIG. 48 show the results of a FACS analysis of hRPCs cultured under normoxic and hypoxic conditions. Markers of interest include nestin, Sox2, Ki-67, GFAP, MHC Class I and II, Fas/CD95, CXCR4, CD15, and GD2 ganglioside.

DETAILED DESCRIPTION

Figure 1:
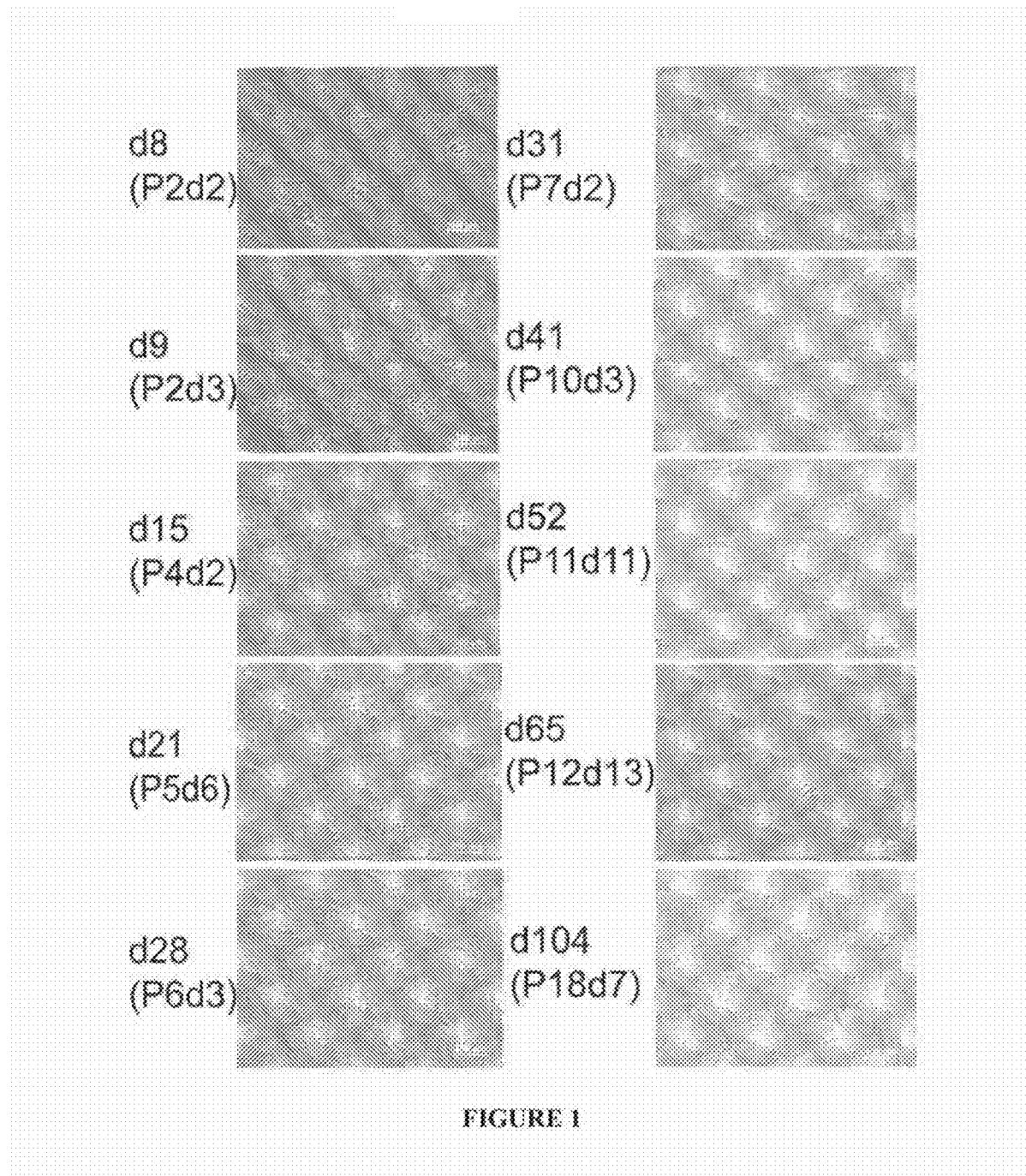
FIG. 1 illustrates the morphology of feline retina-derived progenitors, or RPCs. Morphology was maintained at different time points in the course of sustained culture.

The features, structures, or characteristics described throughout this specification may be combined in any suitable manner in one or more embodiments. For example, the usage of the phrases "exemplary embodiments," "example embodiments," "some embodiments," or other similar language, throughout this specification refers to the fact that a particular feature, structure, or characteristic described in connection with an embodiment may be included in at least one embodiment described herein. Thus, appearances of the phrases "exemplary embodiments," "example embodiments," "in some embodiments," "in other embodiments," or other similar language, throughout this specification do not necessarily all refer to the same group of embodiments, and the described features, structures, or characteristics can be combined in any suitable manner in one or more embodiments.

To facilitate the understanding of this disclosure, a number of terms are defined below. Terms defined herein have meanings as commonly understood by a person of ordinary skill in the areas relevant to the subject matter described herein. Terms such as "a", "an" and "the" are not intended to refer to only a singular entity, but include the general class of which a specific example may be used for illustration. The terminology herein is used to describe specific embodiments of the subject matter described herein, but their usage does not delimit the subject matter, except as outlined in the claims.

In alternative embodiments, provided herein are compositions and methods comprising or using heterogeneous mixtures of fetal neural retinal cells for treating, ameliorating or preventing a retinal disease or condition, e.g., Usher's disease, retinitis pigmentosa (RP), a degenerative retinal disease, an age related macular degeneration (AMD), a wet AMD or a dry AMD, a retinal photoreceptor disease, a diabetic retinopathy, a retinal detachment, a retinal injury, a traumatic or an iatrogenic retinal injury, a ganglion cell or optic nerve cell disease, a glaucoma or an optic neuropathy; or improving a photopic (day light) vision; or for improving correcting visual acuity, or improving macular function, or improving a visual field, or improving scotopic (night) vision. In alternative embodiments, this invention provides heterogeneous mixtures of fetal neural retinal cells and methods and compositions (e.g., kits, formulations and the like) for making and using them.

In alternative embodiments, provided herein are methods and uses of cultured retinal progenitor cells prepared as a cell suspension and used as allogeneic grafts injected into the vitreous cavity of patients with retinal disease. In alternative embodiments, provided herein are cell-based therapies comprising or consisting of use of cultured heterogeneous cell populations from an immature mammalian, e.g., human retina.

In alternative embodiments, proliferating mammalian, e.g., human retinal cells are grown from donor tissue, characterization performed, and cells injected under topical anesthesia directly to the vitreous cavity, without need for systemic immune suppression of the recipient, e.g., a patient.

In alternative embodiments, the compositions and methods of the invention are used for the treatment, prevention or amelioration of a retinal disease, e.g., a retinal degeneration, e.g., a retinitis pigmentosa (RP).

While the invention is not limited by any particular mechanism of action, in one embodiment, donor fetal retinal cells provide a trophic influence for the host retina, notably including host cones. This trophic effect is not only neuroprotective, but also has a rapid revitalizing effect on residual host retinal cells as determined by improved visual function. In one embodiment, donor cells are capable of integrating into the retina and, via cellular differentiation, replace photoreceptors (which can be in limited numbers). The overall effect is to both rapidly and sustainably restore and preserve clinically significant degrees of visual function in a retina otherwise destined to fail completely, leaving the patient completely blind. Accordingly, in one embodiment, the compositions and methods of the invention can rapidly and sustainably restore and preserve clinically significant degrees of visual function in a retina in a mammal, e.g., a human.

In alternative embodiments, methods of the invention comprise making and using dissociated suspensions of fetal retinal cells, e.g., human retinal progenitor cells (hRPCs), and optionally not including tissue or scaffolds. In alternative embodiments, these cells are injected in a vitreous cavity; where optionally no vitrectomy or subretinal surgery is required. In one embodiment, cells can be efficaciously implanted into (e.g., injected into) a subretinal space, or, they can be efficaciously implanted into (e.g., injected into) an eye using any standard intraocular injection procedure, e.g., using a hypodermic or an angled insertion pathway. In alternative embodiments no retinotomy or no intraocular gas or silicon oil is required.

In alternative embodiments, an anterior chamber paracentesis also can be performed, or not depending on situation, as determined by one of skill in the art. In alternative embodiments, no suturing of globe is needed during and/or after a procedure. In alternative embodiments only topical anesthesia is used, e.g., no local, regional, general anesthesia used.

In alternative embodiments, no anti-inflammatory and/or immune suppression is used; but optionally anti-inflammatory and/or immune suppression therapy as post-operative drops can be included. In alternative embodiments, tissue typing of graft and matching to patient is not required.

In alternative embodiments, there is no mandatory bed rest, post-op and/or need for "face-down" positioning. In alternative embodiments, a method of the invention is performed an outpatient procedure, and optionally does not require any overnight hospital stay.

In alternative embodiments, compositions and methods of the invention are used to prevent, ameliorate and/or treat a retinitis pigmentosa (RP), Usher's disease, or any degenerative retinal disease, e.g., AMD, or a retinal photoreceptor disease such as a retinal detachment, or a retinal disease such as a diabetic retinopathy, or a ganglion cell/optic nerve disease such as glaucoma or optic neuropathy.

In alternative embodiments, using or practicing the compositions and methods of the invention results in: improved photopic (day light) vision, optionally providing a rapid effect; increased best-corrected visual acuity; improved macular function, possibility of preserving or regaining central fixation; improved visual field; improvements in scotopic (night) vision, with time; where there is a concomitant hearing loss an in Usher's Syndrome, a reported increased (improved) sensitivity to sound; and/or for patients with LP vision (light perception only), where a treated eye has limited improvement—a marked improvement in visual acuity in a contralateral eye is provided.

In alternative embodiments, using or practicing the compositions and methods of the invention results in various systemic benefits, e.g.: changes in appearance in treated individuals possibly due to somatic improvements, which could be related to effect of light on circadian rhythms, pituitary function, release of hormones, vascular tone, etc.; improved sense of visual capabilities; improved ambulatory independence; improved sense of well-being; and/or improved activities of daily living.

In alternative embodiments, using or practicing the compositions and methods of the invention does not result in: development of unwanted cell growth, e.g., tumors; infections, e.g., no endopthalmitis—a risk for any intraocular procedure; transmission of disease (however, prion or mad cow disease may be difficult to rule out; uveitis and/or acute graft rejection; elevated intraocular pressure; angle closure; hypotony; retinal detachment and/or neovascularization.

In alternative embodiments, compositions and methods of the invention use retinal progenitor cultures comprising or consisting of: heterogeneous cultures of immature retinal cells, obtained from a fetal mammalian retina, which optionally are not clonally selected, but optionally are mixed. In alternative embodiments, the cells express progenitor markers and retinal markers. In alternative embodiments, the cells are raised under xeno-free conditions for clinical use, since xeno-contamination can be a safety issue. In alternative embodiments the cells are grown under completely serum-free conditions, or, the cells can be grown in a serum-containing condition, if desired.

In alternative embodiments the cells are not immortal, nor are they allowed to immortalize, or forced to immortalize. In alternative embodiments the cells do not proliferate indefinitely. Exemplary cell culture methods of this invention can improve rate and duration, and can improve donor cell yield significantly for a given tissue donation.

In alternative embodiments the cells are not stem cells per se, but rather they are immature and/or plastic, and optionally do not meet the definition for true stem cells.

In alternative embodiments, cells used to practice the invention are obtained from mammalian fetal tissue, and optionally do not persist for the life of the organism. In alternative embodiments, cell used to practice the invention cannot (in the absence of additional manipulation) give rise to a germ layer, or cannot (in the absence of additional manipulation) give rise to all three (3) germ layers; optionally they are pre-specified to make retinal tissue or cells.

In alternative embodiments, cells used to practice the invention are a population of closely related cells, not an isolated single cell type. In alternative embodiments, cell used to practice the invention are not pluripotent, and optionally can appear to be multipotent. In alternative embodiments, cells used to practice the invention have never been cultured in a pluripotent state; therefore they are safer. In alternative embodiments, cells used to practice the invention are not genetically modified, or alternatively, they are genetically modified (e.g., transformed stably or transiently, or inducibly).

In alternative embodiments, compositions and methods of the invention provide clinically significant trophic influences to a diseased retina, or provide regenerative influences to a macular and/or a scotopic visual function.

In alternative embodiments, cells used to practice the invention have low immunogenicity, e.g., as allografts, when placed in the eye, or in a vitreous cavity of the eye, or in a subretinal space.

In alternative embodiments, cell used to practice the invention are retinal progenitor cells (RPCs), as distinguished from a neural progenitor and/or a neural stem cells (NSCs). In alternative embodiments, mammalian fetal retinal or RPC cells used to practice the invention are multipotent, but are not equivalent to NSCs. In alternative embodiments, mammalian fetal retinal or RPC cells used to practice the invention are not from the brain, but are from the retina. In alternative embodiments, mammalian fetal retinal or RPC cells used to practice the invention give rise to photoreceptors (brain-derived progenitors are poor at this). In alternative embodiments, mammalian fetal retinal or RPC cells used to practice the invention are multipotent, but do not (in the absence of additional manipulation) give rise to oligodendrocytes (unlike NSCs).

In alternative embodiments, mammalian fetal retinal or RPC cells used to practice the invention are express quantitatively different gene profiles, e.g., as described herein; or they express quantitatively different soluble factor profiles; or they express quantitatively different surface marker profiles.

In alternative embodiments, mammalian fetal retinal or RPC cells used to practice the invention are from a mammalian fetal neural retina, not a ciliary margin, ciliary epithelium, nor RPE. In alternative embodiments, mammalian fetal retinal or RPC cells used to practice the invention are not descended from differentiated Mueller glia, they are not post-mitotic precursors per se, are not stem cells per se, and/or are not a single isolated cell type per se.

In alternative embodiments, mammalian fetal retinal cells or RPC cells used to practice the invention have a gene profile that is not fixed, constant or immutable; or they have a gene profile that dynamically changes quantitatively with time in culture.

In alternative embodiments, mammalian fetal retinal cells or RPC cells used to practice the invention are not found in the early embryo, e.g., the blastocyst. In alternative embodiments, mammalian fetal retinal cells or RPC cells used to practice the invention are not found in any useful abundance in the normal mature mammal, e.g., human. In alternative embodiments, mammalian fetal retinal cells or RPC cells used to practice the invention are found in their native abundance in the developing (fetal) mammalian, e.g., human, retina. In alternative embodiments, mammalian fetal retinal cells or RPC cells used to practice the invention do not normally reside in the bone marrow, nor are derived from same.

In alternative embodiments, mammalian fetal retinal cells or RPC cells used to practice the invention are mostly mitotic when grown under proliferation conditions, optionally along with a minority admixture of post-mitotic cells. In alternative embodiments, mammalian fetal retinal cells or RPC cells used to practice the invention are derived artificially from pluripotent cell lines, although optionally containing no population of residual pluripotent cell types.

In alternative embodiments, mammalian fetal retinal cells or RPC cells used to practice the invention give rise to (differentiate into) retinal cells including photoreceptors, but not oligodendrocytes.

In alternative embodiments, mammalian fetal retinal cells or RPC cells used to practice the invention are immunologically tolerated as ocular allografts in unrelated mammals, e.g., humans. In alternative embodiments, mammalian fetal retinal cells or RPC cells used to practice the invention are grafted to a vitreous cavity for mammalian, or human, vision or retinal disease therapeutic or prophylactic therapy.

In alternative embodiments, mammalian fetal retinal cells or RPC cells used to practice the invention do not come with any, or a substantial risk, of tumor formation or other unwanted cell growth.

In alternative embodiments, mammalian fetal retinal cells or RPC cells used to practice the invention are cultured as spheres or adherent monolayers, or as spheres and then monolayers, or as a combination of spheres and monolayers. In alternative embodiments, spheres are not required, or the cells are grafted as dissociated cells, not as spheres, or as mixture of both. In alternative embodiments, mammalian fetal retinal cells or RPC cells used to practice the invention comprise grafted cells that coalesce in vitreous, and optionally can become spheres.

While the invention is not limited by any particular mechanism of action, an exemplary mechanism of action is diffusible and/or trophic; evidence is consistent with concept of trophic reprogramming of moribund host cones, resulting in switch from apoptotic trajectory to regeneration of photic processing capability. This can be direct or indirect. Involvement of other ocular tissues not ruled out. This mechanism allows for placement of a graft of a heterogeneous mixture of fetal neural retinal cells of the invention in a vitreous or a subretinal space. In one aspect, vitreal placement enhances diffusion-based treatment effect. This mechanism can allows a graft of heterogeneous mixtures of fetal neural retinal cells of the invention to be placed out of the visual axis, yet still treat patient's macula.

In alternative embodiments, a vitreal placement is used to greatly simplify a treatment. This exemplary treatment can increase availability to needy patients worldwide; vitreal placement may aid in immune tolerance by being remote to vasculature. While the invention is not limited by any particular mechanism of action, in a relatively cell-free space, with few native antigen presenting cells, the exemplary vitreal placement of the invention: avoids potential complications of subretinal surgery, avoids risks of general anesthesia, does not require that a hole (retinotomy) be made in retina (which raises risk of retinal detachment, bleeding), and/or does not require the patient's retina undergo a focal detachment (focal detachment can lead to tears, bleeding, global detachment; in RP, detachment of diseased retinal will be a difficult/risky procedure).

In alternative embodiments visual benefits are rapid and may occur within first week post-treatment. In alternative embodiments, incremental benefits occur over longer periods.

In alternative embodiments, retinal cell replacement is possible, but not required for clinical efficacy; donor cell migration into retina is possible, but not required for clinical efficacy. In alternative embodiments, donor cell integration in retinal circuitry is possible, but not required for efficacy; donor cell integration into the outer nuclear layer/macula of host retina is possible, but not required for efficacy. In alternative embodiments, donor cell integration into retina is possible but not required for sustained graft survival.

In alternative embodiments, donor cells are cultured without antibiotics; this can avoid altering cells; and without antibiotics use of very low passage cells is possible since occult microbial contamination can be ruled out. In alternative embodiments, use of low passage cells have a low risk of transformation and/or tumor formation; and, use of low passage cells are closest to the natural cells present in the developing retina.

In alternative embodiments, DMEM/F12-based media or equivalents are preferential for growing human RPCs; and Ultraculture-based media or equivalents are preferential for growing feline progenitors.

The subject matter disclosed herein relates to a cell population comprising mammalian retinal progenitor cells that are isolated according to a defined cell culture method and which express characteristic markers. The cell population may be a culture of cells isolated from a mammal and grown in vitro. For example, the culture may comprise a suspension of cells or adherent cells cultured in a culture plate, dish, flask, or bioreactor. The sample may be homogeneous or heterogeneous, which may be determined by expression of one or more markers as defined herein. In some embodiments, the cell population disclosed herein is a mixed cell population and may contain a mixture of undifferentiated and differentiated cells. Relative expression levels of markers characteristic of the retinal progenitor cells defined herein may vary between cells within the population.

In alternative embodiments, the term "purified" or "enriched" indicates that the cells or cell populations are removed from their normal tissue environment and are present at a higher concentration as compared to the normal tissue environment. Accordingly, a "purified" or "enriched" cell population may further include cell types in addition to retinal progenitor cells and may include additional tissue components, and the term "purified" or "enriched" does not necessarily indicate the presence of only progenitor cells or exclude the presence of other cell types.

In alternative embodiments, the retinal progenitor cell populations as disclosed herein may be at least 5% pure, at least 10% pure, at least 15% pure, at least 20% pure, least 25% pure, at least 30% pure, at least 35% pure, at least 40% pure, at least 45% pure, at least 50% pure, at least 55% pure, at least 60% pure, at least 65% pure, at least 70% pure, at least 75% pure, at least 80% pure, at least 85% pure, at least 90% pure, at least 95% pure, at least 96% pure, at least 97% pure, at least 98% pure, at least 99% pure or at any increment between 5% and 99% pure.

In alternative embodiments, a "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 Daltons). In alternative embodiments, retinal progenitor cells may be characterized by the presence of one or more markers that can be expressed on the surface of the cells within the cell population (a "cell surface marker"), inside cells within the cell population (i.e., in the nucleus or cytoplasm of a cell), and/or expressed at the RNA or protein level as a "genetic" marker.

In alternative embodiments, the terms "express" and "expression" as used herein refers to transcription and/or translation of a nucleic acid sequence within a host cell. The level of expression of a desired product/protein of interest in a host cell may be determined or "screened" on the basis of either the amount of corresponding mRNA that is present in the cell, or the amount of the desired polypeptide/protein of interest encoded by the selected sequence as in the present examples. For example, mRNA transcribed from a selected sequence can be quantified or detected by Northern blot hybridization, ribonuclease RNA protection, in situ hybridization to cellular RNA, microarray analysis, or by reverse-transcription polymerase chain reaction (RT-PCR). Proteins encoded by a selected sequence can be detected or quantified by various antibody-based methods, e.g. by ELISA, by Western blotting, by radioimmunoassays, by immunoprecipitation, by assaying for the biological activity of the protein, by immunostaining of the protein (including, e.g., immunohistochemistry and immunocytochemistry), by flow cytometry or fluorescence activated cell sorting ("FACS") analysis, or by homogeneous time-resolved fluorescence (HTRF) assays.

Retinal progenitor cells may be characterized by their expression of molecular markers, including cell surface markers and non-surface ("genetic") markers. While it is common in the art to refer to cells as "positive" or "negative" for a particular marker, actual expression levels are a quantitatively determined. The number of molecules on the cell surface (or located elsewhere) can vary by several logs, yet still be characterized as "positive". It is also understood by those of skill in the art that a cell which is negative for staining, i.e. the level of binding of a marker specific reagent is not detectably different from a control, e.g. an isotype matched control, may express minor amounts of the marker. Characterization of the level of labeling ("staining") permits subtle distinctions between cell populations. The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

To normalize the distribution to a control, each cell is recorded as a data point having a particular intensity of staining. These data points may be displayed according to a log scale, where the unit of measure is arbitrary staining intensity. By way of example, the brightest stained cells in a sample can be as much as 4 logs more intense than unstained cells. When displayed in this manner, cells falling in the highest log of staining intensity are bright, while those in the lowest intensity are negative. The "low" positively stained cells have a level of staining above the brightness of an isotype matched control, but are not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Expression of markers may be subject to change during culture of retinal tissue from which the retinal progenitor cells and cell populations are derived. For example, differences in marker expression can be influenced by culture conditions such as oxygen levels (i.e., atmospheric oxygen conditions, or "normoxic" conditions; or low oxygen conditions, also known as "hypoxic" conditions). Those of ordinary skill in the art will be aware that marker expression of the retinal progenitor cells and cell populations is not static and may change as a function of one or more culture conditions, i.e., culture media, oxygen levels, number of passages, time in culture, etc.

Retinal progenitor cells and cell populations may express one or more, two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, twenty or more, twenty-five or more, thirty or more of the markers defined herein, or any increment in between up to fifty or more markers.

In alternative embodiments retinal progenitor cells and cell populations comprising retinal progenitor cells are characterized or screened by expression of one or more markers such as, e.g., nestin, vimentin, Sox2, Ki67, MHC Class I, Fas/CD95, MAP2, CD9, CD81, AQP4, CXCR4, CD15/LeX/SSEA1, GD2 ganglioside, CD133, β3-tubulin, GFAP, OPN/SPP1, PTN, KDR, and TEK. In certain embodiments, the retinal progenitor cells and cell populations express one or more markers selected from the group consisting of nestin, Sox2, Ki-67, MHC Class I, and Fas/CD95, wherein nestin is expressed by greater than 90%, or 95-99% of the cells in the population, wherein Sox2 is expressed by greater than 80%, or 90-99% of the cells in the population, wherein Ki-67 is expressed by greater than 30%, or 40-60% of the cells in the population (i.e., 60-85% of cells grown under normoxic/atmospheric oxygen conditions, 80-90% of cells grown under hypoxic conditions), wherein MHC Class I is expressed by greater than 70%, or 90% of the cells in the population, and wherein Fas/CD95 is expressed by greater than 30%, or 40-70% of the cells in the population. In some embodiments, the retinal progenitor cells and cell populations further express one or more markers selected from the group consisting of vimentin, CD9, CD81, AQP4, CXCR4, CD15/LexA/SSEA1, GD2 ganglioside, CD133, 133-tubulin, MAP2, GFAP, OPN/SPP1, PTN, KDR, and TEK. GFAP may be expressed by 5-10% of the cells in the population. MHC Class II may be expressed by 1-3% of the cells in the population. CXCR4 may be expressed by 5-30% of cells grown under atmospheric oxygen conditions, but 90% of cells grown under hypoxic conditions. CD15 may be expressed by 4-35% of cells in the population, i.e., 4-8% of cells grown under atmospheric oxygen conditions, at 15-35% of cells grown under hypoxic conditions. GD2 may be expressed by 2-15% of cells in the population, i.e., 2-4% of cells grown under atmospheric oxygen conditions, 15% of cells grown under hypoxic conditions.

In alternative embodiments retinal progenitor cells and cell populations are characterized or screened for low, trace, negative, or decreased expression of one or more of ABCA4, AIPL1, AKT3, APC2, BSN, CCNG2CDHR1, CRX, CD24, Claudin 11, CNTF, CNTFR, DACH1, DAPL1, DCX, DLG2 and 4, DLL4, EPHA7, EYS, FLT1, FSTL5, FZD5, FGF9, 10, and 14, GADD45G, GRIA2, HES5 and 6, HEY2, HEYL, HGF, HIF3A, IMPG1 and 2, JAK2 and 3, KLF4, MAP6, myelin basic protein (MBP), MYCN, Nanog, NBL1, NEFL, NEFM, NEUROD1, NEUROD4, NEUROG1, NEUROG2, NOTCH 1, 2, and 3, NRL, NRCAM, NRSN, NRXN1, 2, and 3, OCT4, OLIG2, OPN1MW1 and 2, OPN1SW, OTX2, PAR4, PAX6, PRPH2, RAX1 and 2, RBP3, RCVRN, RELN, RGR, rhodopsin, RICTOR, RP1, RRH, RXRG, SIX3 and 6, SOX 8, SLC25A27, STAT1, STAT3, SYP, SYT4, WIF1, VSX2, and VSX1 and 2. The expression pattern of these markers may be used to distinguish retinal progenitor cells or cell populations from tissues of origin, e.g., freshly isolated retinal tissues.

In alternative embodiments other markers whose expression may be increased relative to tissues of origin include, without limitation, ADM, ANGPT1, ANGPTL2 and 4, ATP5D, BHLHE40, CCL2, CCNB1, CCND2, and CCNDE1, CD44, CDKN2A, Claudin 1, 4, and 6, CPA4, CTGF, CXCL12, DKK2, EMP1, FOXC2, FZD6, GADD45B, HES1, HIF1A, HOXB4, IGF1, IGFBP3, 5, and 7, IL1A, IL1R, IL1RAP, IL4R, IL7R, IL11, IL18, JAG1, LIF, LOX, BDNF, EGF, EGFR, FGF1, 2, 5, and 9, KLF4, 5 and 12, MITF, MMP1, MYC, NCAN, NEFH, NOG, NTF3, NTRK2, NRP1 and 2, OSMR (IL31RA), OTX1, PAX8, PDGFA, B, and C, PLAU, PRRX1, RPE65, SDF-1, SFRP1 and 4, SIX1 and 4, SLC25A1, 19, and 20, TEK/TIE1, THBS1 and 2, TLR4, VEGFA, VEGFC WNT5A, and WNT7B.

In alternative embodiments retinal progenitor cells and cell populations are distinguished from other central nervous system progenitor cell types like brain progenitor cells and neural stem cells, and others which may be derived from fetal CNS tissues such as brain and spinal cord. Markers that may be increased relative to other CNS progenitor cells include, without limitation, ARR3 (arrestin C), CDF10, CDKN2A, CTGF, CXCL12/SDF1, BHLHE41, BMP2, DKK1, EGFR, EPHB2, FN1, FOSL1 and 2, FOXD1, GABBR1, GAS1 and 6, GBX2, HHEX, HOXB2, IGFBPS and 7, INHBA, JAG1, KDR, KLF10LHX9, LHX2, LIF, MET, NEUROD1, NTF3, NTRK2, OPTN (optineurin), RCVRN, SAG (S-arrestin), SERPINF1 (PEDF), SFRP1, SOX3, TBX3, TGFB, WIF, WNT5A, and WNT5B. Markers that may be decreased relative to other CNS progenitor cells include, without limitation, AQP4, ASLL1, CLDN11, CDKN1B, CCL2, CCNG2, CXCR4 (SDF1 receptor), DCX, DLX2 and 5, EMX2, EPHA3, 4, and 7, FABP7, FOXG1, GRIA 1, 2, and 3, HGF, IL2, KLF4, LIFR, MNX1, NGF, NKX2-2, NOTCH1, NPY, NPY2R, OLIG2, OMG, PBX1, PDGFRA, RTN1, SCGN, SOX11, TFAP2B, TNFRSF21, and WNT7A.

In alternative embodiments cell populations may be harvested from healthy subjects (i.e., individuals not harboring a retinal disease), from diseased subjects, and may include not only fresh retinal cell populations, but also frozen retinal cell populations. Sources include, without limitation, whole eyes, or retinal tissues, or other sources, obtained from embryonic, fetal, pediatric or adult tissue. The methods can include further enrichment or purification procedures or steps for cell isolation by positive selection for other retinal progenitor cell specific markers. The retinal progenitor cells and cell populations may be obtained or harvested from any mammalian species or subjects, e.g. human, primate, equine, bovine, porcine, canine, feline, ferret, rabbit, rodent, e.g. mice, rats, hamster, etc.

In vertebrate embryonic development, the retina and the optic nerve originate as outgrowths of the developing brain, so the retina is considered part of the central nervous system (CNS) and is actually brain tissue. The retina is a layered structure with several layers of neurons interconnected by synapses. From closest to farthest from the vitreous body, that is, from closest to the front exterior of the head towards the interior and back of the head, the retinal layers include the inner limiting membrane comprised of Müller cell footplates, the nerve fiber layer containing axons of the ganglion cell nuclei, the ganglion cell layer, which contains nuclei of ganglion cells, the axons of which become the optic nerve fiber, the inner plexiform layer that contains the synapse between the bipolar cell axons and the dendrites of the ganglion and amacrine cells, the inner nuclear layer, which contains the nuclei and surrounding cell bodies (perikarya) of the bipolar cells, the outer plexiform layer, containing projections of rods and cones ending in the rod spherule and cone pedicle, respectively, the outer nuclear layer, which contain cell bodies of rods and cones, the external limiting membrane, which separates the inner segment portions of the photoreceptors from their cell nucleus, the photoreceptor layer, and the retinal pigment epithelium (RPE), which is a single layer of cuboidal cells. The neurons that are directly sensitive to light are the photoreceptor cells, comprised mainly of two types: the rods and cones. Rods function mainly in dim light and provide black-and-white vision, while cones support daytime vision and the perception of color. A third type of photoreceptor is the photosensitive ganglion cell, is important for reflexive responses to bright daylight.

In some embodiments, cells are harvested from a mammalian fetal retina at a stage after which the retina is formed, but before photoreceptor outer segments are fully formed throughout the retina and before retinal vascularization has been completed or substantially completed. The stages are typically between fetal gestational ages of about 12 weeks to about 28 weeks in a human fetus. For non-human cells from larger mammals, such as feline or porcine retinal progenitor cells, the stages are typically between fetal gestational ages of about 3 weeks to about 11 weeks. See, for example, Anand-Apte, B. and Hollyfield, J. G. "Developmental Anatomy of the Retinal and Choroidal Vasculature." In *The Retina and Its Disorders*, Besharse, J. and Bok, D., Academic Press, (2001). However, the subject matter disclosed herein also includes harvesting cells from postnatal or neonatal mammalian tissue.

In alternative embodiments retinal progenitor cells are purified from other tissue components after or concurrent with the processing of a tissue sample. In one embodiment, progenitor cells are purified from other cells and tissue components after the tissue sample has been cultured under conditions suitable for cell growth and for a time sufficient to allow cells to adhere to the culture dish. In certain embodiments, purification of cells comprises obtaining cells that migrate from the tissue sample during culture and are present in the culture media or loosely adhered to a fibronectin or other substrate, or a feeder cell layer. These cells may be obtained by routine methods, such as removing and centrifuging the media to pellet cells therein, and washing the cells remaining in the culture dish with a solution such as phosphate-buffered saline (PBS) or Hanks Balanced Salt Solution to remove those cells loosely attached as an adherent cell layer. This wash solution may then also be centrifuged to obtain cells. In some embodiments, purification of retinal progenitor cells and cell populations may further comprise separating cells from certain insoluble tissue components, including residual tissue material, such as lipids. Cells may be separated from other tissue components by any means known and available in the art, including, e.g., the use of density gradients, centrifugation, sorting by flow cytometry or magnetic cell separation (MACS), and filtration or combinations thereof. Examples of specific methods of purifying cells are known and described in the art, e.g., in U.S. Pat. No. 6,777,231. In certain embodiments, negative separation methods are employed to remove one or more particular types of cells.

In certain embodiments, tissue is processed or "dissociated". Dissociation may be carried out by physical dissociation and/or by exposure to an enzyme preparation that facilitates the release of cells from other tissue components to create a "dissociated suspension" of cells and/or cell clusters. Examples of such enzymes include matrix metalloproteinases, clostripain, papain, trypsin, trypsin-like, pepsin, pepsin-like, neutral protease-type and collagenases. Suitable proteolytic enzymes are described in U.S. Pat. Nos. 5,079,160; 6,589,728; 5,422,261; 5,424,208; and 5,322,790. In some embodiments, the enzyme preparation includes trypsin alone or in combination with one or more additional enzymes. Enzymatic dissociation may be carried out in conjunction with physical dissociation by, for example, mincing, pipetting, chopping, homogenizing, grinding, freeze-thawing, osmotically shocking, to remove unwanted cells or connective tissue and ultimately resulting in single cell cultures or may include cell clusters that can be defined by size, i.e., "small", "medium" and "large". Cell cluster size is subjective and may vary in the practice of the subject matter disclosed herein.

Cell culture describes a process by which cells are grown under controlled conditions, generally outside of their natural environment. In alternative embodiments cell populations are grown or cultured in any cell culture medium known in the art. In alternative embodiments, "Basal medium" used in the present invention refers to any medium that can support cell growth. The basal medium provides standard inorganic salts such as zinc, iron, magnesium, calcium, and potassium, vitamins, glucose, buffer system, and key amino acids. The basal medium that can be used in the present invention includes, but is not limited to, Minimum Essential Medium Eagle, ADC-1, LPM (Bovine Serum Albumin-free), F10 (Ham), F12 (Ham), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153, and Ultraculture. Preferred media for use in culturing the retinal progenitor cells disclosed herein are Advanced DMEM/F12 and Ultraculture. A number of these media are summarized in Methods in Enzymology, Volume LVIII, "Cell Culture," pp. 62-72.

In alternative embodiments "Conditioned medium" refers to a medium that is altered as compared to a base or basal medium. For example, the conditioning of a medium may cause molecules, such as nutrients and/or growth factors, to be added to or depleted from the original levels found in the base medium. In some embodiments, a medium is conditioned by allowing cells of certain types to be grown or maintained in the medium under certain conditions for a certain period of time. For example, a medium can be conditioned by allowing retinal progenitor cells to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media.

Examples of cell culture supplements or additives include, without limitation, ingredients to replace partly or wholly the role of serum in supporting cell survival or growth. In alternative embodiments, it includes insulin, transmetalloproteins, trace elements, vitamins, or other factors. These factors are generally not included in the basal medium but are provided by serum used generally in culturing cells. The supplement or additive may comprise at least one or more of the following components that support cell growth: one or more insulins or replacements thereof, one or more transmetalloproteins or replacements thereof, one or more trace elements (e.g., selenium, iron, zinc, copper, cobalt, chromium, iodine, fluoride, manganese, molybdenum, vanadium, nickel, tin), one or more vitamins (e.g., Vitamin C, Vitamin E, Vitamin A, Vitamin B-group), one or more salts (e.g., sodium salts, magnesium salts, calcium salts, or phosphate salts), one or more buffers (e.g., phosphate buffered saline, HEPES buffer), one or more amino acids (e.g., L-glutamine), one or more hormones, hormone-like compounds or growth factors (such as, e.g., transferrin, EGF, NGF, ECGF, PDGF, FGF, IGF, LIF, interleukins, interferons, TGF, and/or VEGF, glucagon, corticosteroids, vasopressin, prostaglandins), serum albumin or replacements thereof, one or more carbohydrates (glucose, galactose, fructose, mannose, ribose, glycolytic metabolites), one or more antibiotics and/or antimycotics (e.g., penicillin, streptomycin, Fungizone), and one or more lipids (e.g., free and protein-bound fatty acids, triglycerides, phospholipids, cholesterol, ethanolamine). Many commercialized serum replacement additives, such as KnockOut Serum Replacement (KOSR), N2, B27, StemPro, Insulin-Transferrin-Selenium Supplement (ITS), and G5 are well known and are readily available to those skilled in the art. These additives are characterized by well-defined ingredients, so the concentrations of its components can be determined based on its proportion in the medium.

In alternative embodiments cultures of mammalian retinal progenitor cells can be produced in medium containing reduced serum or no serum. Examples of serum include fetal bovine serum, calf serum, newborn calf serum, goat serum, horse serum, human serum, rabbit serum, rat serum, mouse serum, among others. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some embodiments, retinal progenitor cells and cell populations comprising retinal progenitor cells are grown without serum ("serum-free"), without serum replacement and/or without any supplement.

In some embodiments, retinal progenitor cells or cell populations comprising retinal progenitor cells are cultured under "xeno-free" conditions. "Xeno-free" or "xenogen-free" refers to conditions where cells of a certain species (e.g., human cells) are grown or cultured only in the presence of human products or supplements (e.g., human serum albumin, human serum), but not products from other species. This is particularly important for cells that are used for transplantation into a human. Cells that have been exposed to a variety of undefined animal-derived products make them undesirable for clinical applications, because of an increased risk of graft rejection, immunoreactions, and viral or bacterial infections, prions, and yet unidentified zoonoses. Moreover, for all mammalian uses, including human use or non-human mammalian uses (e.g., veterinary uses), cells are screened for normal karyotype or presence of infection or contamination, e.g., by mycoplasma, gram negative bacteria (e.g., endotoxin test), fungi and the like. Cells may also be screened for tumorigenicity or transformation to a cancerous phenotype by telomerase activity assay, hTERT gene expression, and growth in soft agar or tumor formation in nude mice. Such assays are known in the art and well within the purview of the skilled artisan.

In alternative embodiments retinal progenitor cells or cell populations comprising retinal progenitor cells may be cultured on feeder cell layers (e.g., embryonic or adult fibroblasts), or in the presence of an extracellular matrix scaffold or substrates such as collagen, entactin, heparin sulfate proteoglycans, fibronectin, laminin, gelatin, or Matrigel. For example, PURECOL® collagen is known as the standard of all collagens for purity (>99.9% collagen content), functionality, and the most native-like collagen available. PURECOL® collagen is approximately 97% Type I collagen with the remainder being comprised of Type III collagen, and is ideal for coating of surfaces, providing preparation of thin layers for culturing cells, or use as a solid gel. Another example of a scaffold or substrate known in the art is CELLstart (Invitrogen).

In alternative embodiments cell culture conditions can involve growth of cells in an incubator set at 37° C., 5% $CO_2$. Retinal progenitor cells or cell populations comprising retinal progenitor cells may be cultured under normoxic or atmospheric (20%), and can be grown under conditions that approximate oxygen levels of a developing fetal retina during gestation, i.e., "low" or "hypoxic" conditions, e.g., 0.5%, 1%, 1.5%, 2%, 2.5%, 3%, 3.5%, 4%, 4.5%, 5%, 5.5%, 6%, 6.5% or 7% oxygen, or any increment in between.

Plating density refers to the number of cells per volume of culture medium or the number of cells per $cm^2$ in adherent culture. A similar term in this context is "confluence", which is commonly used as a measure of the number of the cells in a cell culture dish or a flask, and refers to the coverage of the dish or the flask by the cells. For example, 100 percent confluency means the dish is completely covered by the cells, and therefore no more room left for the cells to grow; whereas 50 percent confluency means roughly half of the dish is covered and there is still room for cells to grow.

Passaging (also known as subculture or splitting cells) involves transferring a small number of cells into a new vessel. In alternative embodiments cells are cultured for a longer time if they are split regularly, as it avoids the senescence associated with prolonged high cell density. Suspension cultures are easily passaged with a small amount of culture containing a few cells diluted in a larger volume of fresh media. For adherent cultures, cells first need to be detached; this is commonly done with a mixture of an enzyme such as trypsin-EDTA or non-enzymatic solution like Cell Dissociation Buffer; however, a variety of enzyme or non-enzyme mixes or preparations are available for this purpose. A small number of detached cells can then be used to seed a new culture.

Most primary cell cultures have limited lifespan and do not proliferate indefinitely. After a certain number of population doublings (called the Hayflick limit), cells undergo the process of senescence and stop dividing, while generally retaining viability. In alternative embodiments, the retinal progenitor cells and cell populations can be cultured for no more than 10 passages, for example, are passaged one, two, three, four, five, six, seven, eight, nine, or ten passages. In alternative embodiments, cells can be passaged more than 10 times, such as, e.g., eleven, twelve, thirteen, fourteen, fifteen, sixteen, seventeen, eighteen, nineteen, twenty or more passages. In certain embodiments, the retinal progenitor cells and cell populations are cultured for about 10-30 passages. In alternative embodiments, retinal progenitor cells and cell populations comprising them are preferably not immortal, nor are they allowed to immortalize, or forced to immortalize. While the cells described herein are considered immature progenitor cells, the cell populations comprising the retinal progenitor cells may contain cells that may be considered "multipotent" stem cells per se, wherein such cells are generally capable under certain culture conditions of differentiating into retinal tissue or retinal cells, including retinal progenitor cells. In alternative embodiments "Multipotent" refers to immature, undifferentiated and/or unspecialized cells that have the ability to self-renew, but are limited in the ability to differentiate and are essentially committed to produce specific cell types. In certain embodiments, cells and cell populations described herein comprise closely related cells, but are not necessarily indicative of a single cell type.

In alternative embodiments retinal progenitor cells are genetically modified to express one or more heterologous or exogenous nucleic acid sequences of interest. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Nucleic acid sequences include plasmids, amplicons, cDNA, mRNA, antisense RNA, siRNA, but are not limited to these examples. The term "gene" refers to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants.

Any methodology known in the art can be used for genetically altering the tissue. One exemplary method is to insert a gene into the cells of the tissue with a recombinant viral vector. Any one of a number of different vectors can be used, such as viral vectors, plasmid vectors, linear DNA, etc., as known in the art, to introduce an exogenous nucleic acid fragment encoding for a therapeutic agent into target cells and/or tissue. These vectors can be inserted, for example, using any of infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound and others as known in the art.

In alternative embodiments a "vector" is used to refer to a carrier nucleic acid molecule into which a nucleic acid sequence can be inserted for introduction into a cell where it can be replicated. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences. In addition to encoding a modified polypeptide, a vector may encode non-modified polypeptide sequences such as a tag or targeting molecule. Useful vectors encoding such fusion proteins include pIN vectors, vectors encoding a stretch of histidines, and pGEX vectors, for use in generating glutathione S-transferase (GST) soluble fusion proteins for later purification and separation or cleavage.

In alternative embodiments vectors of the present invention are designed primarily to introduce into cells a heterologous nucleic acid molecule, such as a gene that is "operably linked" or under the control of one or more control sequences. A "promoter" refers to one or more transcriptional control modules that are clustered around the initiation site for RNA polymerase II and other transcriptional activator proteins. Any promoter/enhancer combination (as per the Eukaryotic Promoter Data Base EPDB) could also be used to drive expression of a nucleic acid molecule of interest (i.e., constitutive, inducible, repressible, tissue specific). Also, the vectors may contain a selectable marker to facilitate their manipulation in vitro or ex vivo. Vectors may also contain a polyadenylation signal, which may be obtained from the human growth hormone (hGH) gene, the bovine growth hormone (BGH) gene, or SV40. In addition, vectors may also contain internal ribosome binding sites (IRES) elements are used to create multigene, or polycistronic, messages. IRES elements are able to bypass the ribosome scanning model of 5-methylated cap-dependent translation and begin translation at internal sites (Pelletier, J. and Sonenberg, N. (1988) Nature 334(6180): 320-325). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In alternative embodiments, a vector is a viral vector. Viral vectors known in the art include, without limitation, adenoviral vectors, retroviral vectors, vaccinia viral vectors, adeno-associated viral vectors, polyoma viral vectors, alphaviral vectors, rhabdoviral vectors, lentiviral vectors, Epstein-Barr viral vectors, picornaviral vectors, or herpesviral vectors.

In other embodiments, a nucleic acid sequence may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh, P. C. and Bachhawat, B. K. (1991) Targeted Diagn. Ther. 4: 87-103). One example of a commercially available liposomes or lipid formulations is Lipofectamine (Invitrogen). Others include FuGENE (Promega), PromoFectin (PromoKine), Affectene (Qiagen), Polyfect (Qiagen), Superfect (Qiagen), and Trans-Messenger (Qiagen).

The subject matter disclosed herein also provides methods of treating a retinal disease or condition in a subject in need thereof by administering to the subject a composition comprising a cell population comprising mammalian retinal progenitor cells into a subject's vitreous cavity or subretinal space, and optionally measuring changes or improvements in vision in the subject.

In alternative embodiments the term "treating" in its various grammatical forms in relation to the present invention refers to curing, reversing, attenuating, alleviating, minimizing, suppressing or halting the deleterious effects of a disease state, disease progression, disease causative agent or other abnormal condition. For example, treatment may involve alleviating a symptom (i.e., not necessary all symptoms) of a disease or attenuating the progression of a disease. In alternative embodiments the term "preventing" means that the effects of a disease state or disease causative agent has been obviated due to administration of an agent, such as those disclosed herein. A similar term in this context is "prophylaxis".

"Patient" or "subject" are used interchangeably herein and refer to the recipient of treatment. Mammalian and non-mammalian subjects are included. In some embodiment, the subject is a mammal, such as a human, non-human primate, canine, murine, feline, bovine, ovine, porcine, or caprine. In some embodiments, the subject is a human.

Cell populations and related compositions described herein may be provided to a subject or patient by a variety of different means. In certain embodiments, they are provided locally, e.g., to a site of actual or potential injury or disease. In some embodiment, they are provided using a syringe or needle to inject the compositions at a site of possible or actual injury or disease. In other embodiments, they are provided systemically, i.e., administered to the bloodstream intravenously or intra-arterially. The particular route of administration will depend, in large part, upon the location and nature of the disease or injury being treated or prevented. Accordingly, the subject matter described herein includes providing a cell population or composition of the invention via any known and available method or route, including but not limited to oral, parenteral, intravenous, intra-arterial, intranasal, and intramuscular administration. The determination of suitable dosages and treatment regimens may be readily accomplished based upon information generally known in the art and obtained by a physician. Treatment may comprise a single treatment or multiple treatments. In particular, for preventative purposes, it is contemplated in certain embodiments that purified cell populations of the invention are administered following a stress that might potentially cause retinal injury. In other embodiments, the cell populations and compositions may be locally administered as a single injection to the vitreous cavity or subretinal space of the subject. Alternatively, the compositions or cell populations may be administered two times, three times, four times, or any number of times in the practice of the methods provided herein.

In alternative embodiments methods of the invention comprise isolation and characterization of mammalian retinal progenitor cells and compositions comprising such cells that are harvested from donor tissue, grown in culture, and formulated for administration to a subject or patient. In some embodiments, the methods comprise administering the compositions under topical anesthesia directly to the vitreous cavity, without need for systemic immune suppression of the subject. In alternative embodiments, tissue typing of graft and matching to patient or subject is not required, but may be performed if desired. Tissue typing and matching techniques are well known to those skilled in the art.

The retinal progenitor cells and cell populations used to practice this invention may be formulated as a composition for administration by any or a variety of means including orally, parenterally, by inhalation spray, nasally, topically, intrathecally, intrathecally, intracerebrally, epidurally, intracranially or rectally. Compositions and formulations disclosed herein can comprise pharmaceutically or veterinarily acceptable liquids, carriers, adjuvants and vehicles and can be in the form of liquids, tablets, capsules, implants, aerosols, gels, liposomes, nanoparticles and the like.

In some embodiments, the retinal progenitor cells and cell populations may be administered to a subject in the form of pharmaceutical or veterinary compositions. The phrase "pharmaceutically acceptable" refers to molecular entities and compositions that do not produce adverse, allergic, or other untoward reactions when administered to an animal or a human. As used herein, "pharmaceutically acceptable carrier" includes any and all aqueous and nonaqueous carriers which includes water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the presence of microorganisms may be ensured both by sterilization procedures and by the inclusion of various antibacterial and antifungal agents, for example, paraben, chlorobutanol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. It must be stable under the conditions of manufacture and storage and must be preserved against the contaminating action of microorganisms, such as bacteria and fungi. The use of such media and agents for pharmaceutically active substances is well known in the art.

In certain embodiments, an effective amount of the retinal progenitor cells or cell populations must be administered to the subject. An "effective amount" or "therapeutically effective amount" refers to the amount of the composition that produces a desired effect. An effective amount will depend, for example, in part, upon the molecule or agent delivered (here the retinal progenitor cells or cell populations), the indication for which the therapeutic agent is being used, the route of administration, and the size (body weight, body surface or organ size) and condition (the age and general health) of the subject or patient. Accordingly, the clinician or physician may titer the dosage and modify the route of administration to obtain the optimal therapeutic effect. An effective amount of a particular agent for a specific purpose can be determined using methods well known to those in the art. For any composition defined herein, the effective amount can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

Examples of effective amounts of the compositions described herein include cell suspensions at a volume of 5 µl, 10 µl, 15 µl, 20 µl, 25 µl, 50 µl, 100 µl, 150 µl, 200 µl, 250 µl, 300 µl, 350 µl, 400 µl, 450 µl, 500 µl or any increment in between up to 5000 µl (5 ml). The lower and upper volume limits are limited by the delivery system and/or method. See, e.g., Kayikcuiglu, O. R. et al, (2006) Retina 26(9): 1089-90. For example, the upper volume limit when administered without vitrectomy is approximately 200 µl due to increased intraocular pressure. The upper volume limit when administered with vitrectomy into the vitreous cavity is limited by the volume of the vitreous cavity and can comprise up to 5 ml or more. The upper limit for subretinal injection may be up to 200 µl due to retinal detachment. In alternative embodiments, these volumes include anywhere between 1000 to 10 million cells per dose, or 1000 to 2000 cells per dose, 2000 to 3000 cells per dose, 3000 to 4000 cells per dose, 400 to 5000 cells per dose, 5000 to 6000 cells per dose, 6000 to 7000 cells per dose, 7000 to 8000 cells per dose, 8000 to 9000 cells per dose, 9000 to 10,000 cells per dose, 10,000 to 15,000 cells per dose, 15,000 to 20,000 cells per dose, 20,000 to 25,000 cells per dose, 25,000 to 30,000 cells per dose, 30,000 to 35,000 cells per dose, 35,000 to 40,000 cells per dose, 40,000 to 45,000 cells per dose, 45,000 to 50,000 cells per dose, 50,000 to 55,000 cells per dose, 55,000 to 60,000 cells per dose, 60,000 to 65,000 cells per dose, 65,000 to 70,000 cells per dose, 70,000 to 75,000 cells per dose, 75,000 to 80,000 cells per dose, 80,000 to 85,000 cells per dose, 85,000 to 90,000 cells per dose, 90,000 to 95,000 cells per dose, 95,000 to 100,000 cells per dose, 100,000 to 125,000 cells per dose, 125,000 to 150,000 cells per dose, 150,000 to 200,000 cells per dose, 200,000 to 250,000 cells per dose, 250,000 to 300,000 cells per dose, 300,000 to 350,000 cells per dose, 350,000 to 400,000 cells per dose, 400,000 to 450,000 cells per dose, 450,000 to 500,000 cells per dose, 500,000 to 550,000 cells per dose, 550,000 to 600,000 cells per dose, 600,000 to 650,000 cells per dose, 650,000 to 700,000 cells per dose, 700,000 to 750,000 cells per dose, 750,000 to 800,000 cells per dose, 800,000 to 850,000 cells per dose, 850,000 to 900,000 cells per dose, 900,000 to 950,000 cells per dose, 950,000 to 1,000,000 cells per dose or in any increment in between 1000 cells and up to 10 million cells per dose. Dosages may, of course, vary according to frequency and duration of administration. In alternative embodiments the dosage of cells in the compositions described herein contains a high number of cells in a small volume, such as, for example, 0.5 million cells per 100 µl. Cell numbers may be counted by any method known in the art, such as by hemacytometer, spectrophotometry, Coulter counter, flow cytometry, etc. Dosing may be administered once or may be administered over the course of several treatments.

In alternative embodiments compositions of the invention can be formulated for parenteral administration into the eye (particularly into the vitreous cavity or subretinal space), a vitreous cavity or a subretinal space, retina, brain, nerve or CNS by transscleral delivery, or by any method or protocol known in the art, e.g., including a transscleral delivery as described in U.S. Pat. No. 7,585,517; a sustained release delivery device for delivery to the interior of a patient's eye as described in U.S. Pat. No. 7,883,717; a device for insertion in the vitreous region of the eye as described in U.S. Pat. Nos. 5,378,475 or 5,466,233; or by use of a hypodermic syringe or angled insertion pathway, e.g., as described in U.S. Patent Application Publication Nos. 20110112470 or 20100256597 (describing a microneedle for targeted administration to a patient's eye); or via a hydrophilic polymer hydrogel with dimensions to pass through a puncta lacrimali e.g., as described in U.S. Patent Application Publication No. 20100209478; or a device that provides access to the sub-retinal space in a human eye e.g., as described in U.S. Patent Application Publication No. 20100191176. Anterior chamber paracentesis also can be performed as determined by one of skill in the art. In alternative embodiments, methods do not require suturing of globe during and/or after a procedure, particularly for intravitreal placement. However, this may be necessary for methods utilizing a vitrectomy procedure, for example, when placing cells in the subretinal space.

The compositions disclosed herein may also be formulated for intrathecal, intracerebral epidural, subcutaneous, intravenous, intramuscular and/or intraarterial administration; e.g., as described in U.S. Patent Application Publication No. 200500480021; by injection routes but also including a variety of infusion techniques. Administration may be carried out through the use of catheters or pumps, e.g., an intrathecal pump, or an implantable medical device. In alternative embodiments methods of the invention also may involve administration or transplantation of implants and artificial organs, bioreactor systems, cell culture systems, plates, dishes, tubes, bottles and flasks and the like, comprising the retinal progenitor cells, cell populations, or compositions disclosed herein, such as those described in U.S. Pat. Nos. 7,388,042; 7,381,418; 7,379,765; 7,361,332; 7,351,423; 6,886,568; 5,270,192; and U.S. Patent Application Publication Nos. 20040127987; 20080119909; 20080118549; 20080020015; 20070254005; 20070059335; 20060128015.

In alternative embodiments methods provided herein may be used for treating, ameliorating or preventing a retinal disease or condition, such as, without limitation, retinitis pigmentosa (RP), Leber's congenital amaurosis (LCA), Stargardt disease, Usher's syndrome, choroideremia, a rod-cone or cone-rod dystrophy, a ciliopathy, a mitochondrial disorder, progressive retinal atrophy, a degenerative retinal disease, age related macular degeneration (AMD), wet AMD, dry AMD, geographic atrophy, a familial or acquired maculopathy, a retinal photoreceptor disease, a retinal pigment epithelial-based disease, diabetic retinopathy, cystoid macular edema, uveitis, retinal detachment, traumatic retinal injury, iatrogenic retinal injury, macular holes, macular telangiectasia, a ganglion cell disease, an optic nerve cell disease, glaucoma, optic neuropathy, ischemic retinal disease, retinopathy of prematurity, retinal vascular occlusion, familial macroaneurysm, a retinal vascular disease, an ocular vascular diseases, a vascular disease, or ischemic optic neuropathy; for improving a photopic (day light) vision; or for improving correcting visual acuity, or improving macular function, or improving a visual field, or improving scotopic (night) vision.

In alternative embodiments treatment methods of the invention utilize topical anesthesia, however any local, regional or general anesthesia may be used during administration. Examples of local anesthetics suitable for use in the methods disclosed herein include, without limitation, mepricaine, proparacaine, prilocaine, ropivacaine, benzocaine, bupivacaine, butamben picrate, chlorprocaine, cocaine, dibucaine, dimethisoquin, dyclonine, etidocaine, hexylcaine, ketamine, lidocaine, mepivacaine, pramoxine, procaine, tetracaine, salicylates and derivatives, esters, salts and mixtures thereof.

The compositions comprising retinal progenitor cells or cell populations may optionally be co-administered with one or more drugs. Examples of drugs may include anti-angiogenesis agents such as angiostatin, anecortave acetate, thrombospondin, VEGF receptor tyrosine kinase inhibitors and anti-vascular endothelial growth factor (anti-VEGF) drugs such as ranibizumab and bevacizumab, pegaptanib, sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as acetbutolol, atenolol, bisoprolol, carvedilol, asmolol, labetalol, nadolol, penbutolol, pindolol, propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluorometholone, loteprednol, medrysone, fluocinolone acetonide, triamcinolone acetonide, triamcinolone, triamcinolone acetonide, beclomethasone, budesonide, flunisolide, fluorometholone, fluticasone, fludrocortisone, hydrocortisone, hydrocortisone acetate, loteprednol, rimexolone and non-steroidal anti-inflammatory agents including, for example, aspirin, diclofenac, flurbiprofen, ibuprofen, bromfenac, nepafenac, and ketorolac, salicylate, indomethacin, naxopren, piroxicam and nabumetone diflunisal, etodolac, fenoprofen, flurbiprofen, indomethacine, ketoprofen, meclofenamate, mefenamic acid, meloxicam, nabumetone, oxaprozin, piroxicam, salsalate, sulindac and tolmetin; COX-2 inhibitors like celecoxib, rofecoxib and Valdecoxib; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin, tobramycin, amikacin and streptomycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B, caspofungin, clotrimazole, fluconazole, itraconazole, ketoconazole, voriconazole, terbinafine, nystatin and miconazole; anti-malarial agents such as chloroquine, atovaquone, mefloquine, primaquine, quinidine and quinine; anti-mycobacterium agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate;

Other examples of drugs may also include antiviral agents such as idoxuridine trifluorothymidine, acyclovir, cidofovir, famciclovir, gancyclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other antiviral agents such as interferons, ribavirin and trifluridiene; anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other anti-bacterials such as aztreonam, chloramphenicol, clindamycin, linezolid, nitrofurantoin and vancomycin.

Other examples of drugs may also include immune-modulating agents such as antiallergenics, including, for example, sodium chromoglycate, antazoline, methapyriline, chlorpheniramine, cetrizine, pyrilamine, prophenpyridamine; aldesleukin, adalimumab, azathioprine, basiliximab, daclizumab, etanercept, hydroxychloroquine, infliximab, leflunomide, methotrexate, mycophenolate mofetil, and sulfasalazine; anti-histamine agents such as azelastine, emedastine, loratadine, desloratadine, cetirizine, diphenhydramine, chlorpheniramine, dexchlorpheniramine, clemastine, cyproheptadine, fexofenadine, hydroxyzine, promethazine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor, transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers, sodium channels blockers, glutamate inhibitors such as memantine, neurotrophic factors, nitric oxide synthase inhibitors; free radical scavengers or anti-oxidants; chelating compounds; apoptosis-related protease inhibitors; compounds that reduce new protein synthesis; radiotherapeutic agents; photodynamic therapy agents; gene therapy agents; genetic modulators; and dry eye medications such as cyclosporine A, delmulcents, and sodium hyaluronate; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban.

Other therapeutic agents may include prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-flurouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

The uses and methods described herein can rapidly and sustainably restore and/or preserve clinically significant degrees of visual function in a retina in mammalian subjects, including but not limited to, improved photopic (day light) vision, increased best-corrected visual acuity, improved macular function, preserving or regaining central fixation, improved visual field, improvements in scotopic (night) vision, increased or improved sensitivity to sound, and improvements in visual acuity in a contralateral eye. Other changes may include various systemic benefits, e.g., changes in appearance due to somatic improvements, which could be related to effect of light on circadian rhythms, pituitary function, release of hormones, vascular tone; an improved sense of visual capabilities; improved ambulatory independence; improved sense of well-being; and/or improved activities of daily living. Such changes in vision can be measured by methods known in the art. Visual benefits may occur within first week post-treatment, but may also occur as incremental benefits over longer periods of time. Retinal cell replacement and/or donor cell migration into the retina, retinal circuitry, or outer nuclear layer or macula may occur, but is not required for clinical efficacy; donor cell migration into retina is possible, but not required for clinical efficacy.

Measuring changes in vision, including improvements in vision resulting from treatment with the retinal progenitor cell compositions disclosed herein can be achieved using standard ophthalmic examination techniques, including but not limited to, fundus examination, best corrected visual acuity (BCVA), IOP, slit lamp examination, fluorescein angiography (FA), Optical Coherence Tomography (OCT), stereo-fundus photography, electroretinography (ERG), cone flicker electroretinography, perimetry (visual field), microperimetry, dark adaptation, maze negotiating skill, optokinetic/optomotor responses, pupillary responses, visual evoked potentials (VIP), and adaptive optics scanning laser ophthalmoscopy (AOSLO).

Kits and Instructions

The invention provides kits comprising compositions (e.g., a heterogeneous mixture of fetal neural retinal cells) and methods of the invention (e.g., treating a retinal disease or condition, or making a heterogeneous mixture of fetal neural retinal cell), including instructions for use thereof. In alternative embodiments, the invention provides kits comprising a composition, product of manufacture, or mixture or culture of cells (e.g., heterogeneous mixture of fetal neural retinal cells) of the invention; wherein optionally the kit further comprises instructions for practicing a method of the invention.

The invention provides kits comprising a cell population comprising the mammalian retinal progenitor cells described herein, whether provided as cells in culture, fresh or frozen, or formulated as a composition for administration into a subject. The kit may further comprise instructions for practicing a method of the invention. Such kits may additional comprise an agent that binds one or more marker of retinal progenitor cells described herein (e.g., an antibody or oligonucleotide primer), and basal or conditioned medium. For example, a kit may include: a first container comprising an antibody specific for one or more markers, wherein said antibody is adapted for isolation or detection, e.g., by being conjugated to a fluorescent marker or magnetic bead; and a second container comprising basal or conditioned medium. In various related embodiments, the kits may further comprise one or more additional reagents useful in the preparation of a cell population of the present invention, such as cell culture medium, extracellular matrix-coated cell culture dishes, and enzymes suitable for tissue processing. The kit may also include instructions regarding its use to purify and expand the retinal progenitor cells or cell populations obtained from a tissue sample. In other embodiments, the kits may further comprise a means for obtaining a tissue sample from a patient or donor, and/or a container to hold the tissue sample obtained.

Veterinary Applications

In alternative embodiments, compositions and methods of the invention can be used for veterinary applications; e.g., this invention demonstrates the first successful growing of feline RPCs, and the first therapeutic application to the retina in a dystrophic cats and other animals, e.g. any mammalian pet, common domesticated and rare wild mammalian species, zoo animals, farm animals, sport (e.g., racing dogs or horses) animals, and the like.

There are a number of domesticated animals that harbor genes causing blindness as a result of extensive inbreeding. These included cats, dogs, and horses, and probably other species. There are retinal diseases and injuries that occur in wild and domestic animals that will benefit from treatment using compositions and methods of the invention.

Products of Manufacture, Implants and Artificial Organs

The invention also provides implants and artificial organs, bioreactor systems, cell culture systems, plates, dishes, tubes, bottles and flasks and the like comprising one more formulations or pharmaceuticals of the invention comprising a heterogeneous mixture of fetal neural retinal cells.

In alternative embodiments the invention provides a bioreactor, implant, stent, artificial organ or similar devices comprising a heterogeneous mixture of fetal neural retinal cells; for example, implants analogous to or as described in U.S. Pat. Nos. 7,388,042; 7,381,418; 7,379,765; 7,361,332; 7,351,423; 6,886,568; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

The invention will be further described with reference to the following examples; however, it is to be understood that the invention is not limited to such examples.

EXAMPLES

Example 1

Isolation and Culture of Retinal Progenitor Cells

Whole fetal eyes of approximately 16 to 19 weeks gestational age (GA) fetuses were obtained from donors and placed in a 15 ml tube containing RPMI-1640 medium with L-glutamine (BioWhittaker). The eyes were shipped on ice for a period of 4.5 hours to approximately 21.5 hours. At the same time, blood samples from the donor were drawn and sent for testing for exposure to adventitious agents. On arrival, each eyeball was examined to ensure that the corneas were clear and of normal shape, then placed under a laminar flow hood under sterile conditions. Whole fetal eyes were rinsed three times in 40 ml cold phosphate-buffered saline (PBS) containing antibiotics in separate 50 ml tubes. The optic nerve and remaining mesenchymal tissue were then removed by dissection. This approach was taken to avoid possible contamination of retinal isolates with unwanted cells of non-retinal origin. After dissection, the eyes were rinsed one more time in cold PBS containing antibiotics.

Under a binocular dissection microscope, a hole was punctured in each eye at the surgical limbus using a 1 ml "TB"-type syringe mounted with 25⅝ gauge needle. The eyeball was then opened circumferentially by cutting with fine scissors along the limbus. The anterior structures (cornea, lens) and any remaining vitreous body were removed from the eye cup. The retina was then freed by carefully teasing away from the retinal pigment epithelium (RPE), and transferred into a small petri dish containing approximately 2 ml cold DMEM/F12 medium. The retinal tissue was manually broken into small pieces by gentle trituration through a 1 ml tip in the Petri-dish. The retinal chunks were transferred in suspension into a 15 ml cold conical bottom tube, and any remaining tissue was collected by rinsing the petri dish 2-3 times in 1 ml cold DMEM/F12 and adding it to the 15 ml tube. The tissue was spun down by centrifugation at 1000 rpm (179×g) for 5 minutes and the supernatant was discarded.

The tissues were then subjected to enzymatic digestion by incubation in 0.8 ml undiluted TrypLE Express (Invitrogen) for 40 seconds at room temperature. The trypsinized tissues were then drawn up and down through a 1 ml pipette tip. The trypsin was neutralized by subsequently adding 10 ml of cold fresh serum-free cell culture medium and the mixture collected by centrifugation at 1000 rpm (179×g) for 4 minutes. The supernatant was removed and the pellet resuspended in cold fresh cell culture medium, then cell viability and cell number were determined by Trypan blue (Invitrogen) dye exclusion, and counted using Countess (Invitrogen) or manually. Approximately $10 \times 10^6$ cell clusters were obtained, wherein approximately 80% were small/medium clusters, approximately 9 to 18% were single cells, and approximately 1 to 2% were big clusters. This technique resulted in around 92% cell viability.

Cells were then seeded into two T75 culture flasks previously coated with human (xeno-free) fibronectin. Human plasma fibronectin (Invitrogen) was used in some experiments. In other experiments, ornithine, polylysine, laminin or Matrigel were used. The cells were then incubated at 37° C. under 5% $CO_2$ and atmospheric oxygen or alternatively, in 3% 02 using a LowOx incubator. During culture, care was taken to further dissociate the clusters by trypsinization and/or trituration to prevent premature differentiation as the cells are subsequently passaged. Every one or two days, 90% of the cell culture medium was changed and cells were passaged at 60-80% confluence, optionally at 40-90% confluence, using TrypLE Express for 5 to 6 minutes at 37° C. Trypsinization was stopped by adding 10 ml of cold medium or cold PBS. Cell viability was determined by Trypan blue staining, and cell number was counted. Dissociated cells were subsequently seeded into new fibronectin-coated flasks or plates at a density of 1 to $6.7 \times 10^4/cm^2$.

Cells were prepared for freezing by first harvesting them with TrypLE Express. The cells were collected by centrifugation at 1000 rpm (179×g) for 5 minutes. The supernatant was removed and the cell pellet resuspended in fresh medium or cold PBS. Cell viability and cell number were determined. The cells were subsequently spun down again at 1000 rpm for 5 minutes and resuspended in cell cryopreservation medium (90% fresh complete medium, 10% DMSO), aliquoting 0.5 to 5×10$^6$ cells per cryovial. The cryovials were placed at 1° C. in a freezing container, and then moved to a freezer at −80° C., a liquid nitrogen tank, or other sustained low temperature storage.

To thaw cells, the cryovials were removed from liquid nitrogen/storage and placed in a 37° C. water bath for 2-3 minutes until ice crystals disappeared. The thawed cells were then transferred to a cold 15 ml conical tube immediately using 1 ml pipette tip and the vials rinsed twice with cold fresh medium. Ten milliliters of cold fresh medium were added into the 15 ml tube dropwise with gentle shaking. The cells were then collected by centrifugation at 800 rpm (115×g) for 3 minutes, the supernatant discarded, and the resultant cell pellet resuspended in fresh medium. Cell number and viability were determined as described herein, and then the cells were seeded into new fibronectin-coated flasks and incubated under the conditions described above.

Figure 2:
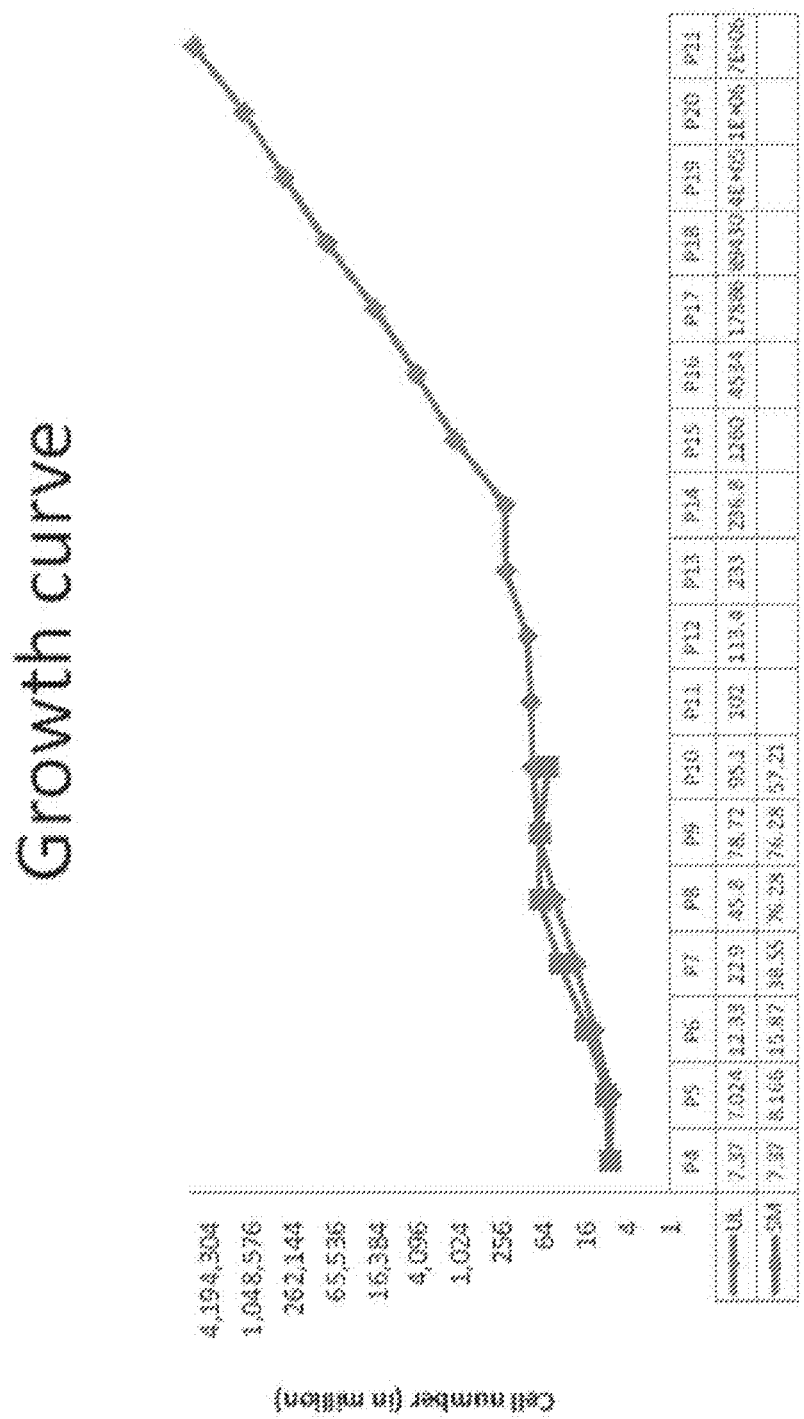
FIG. 2 is a graph representing a growth curve showing the differences in growth of the feline RPCs in SM medium versus UL medium.

The morphology of feline retina-derived progenitors is shown in FIG. 1. As seen in this figure, morphology was maintained at different time points in the course of sustained culture. FIG. 2 illustrates a growth curve of feline RPCs grown in two different types of cell culture media. The feline RPCs in SM senesced at passage day 10 (P10), whereas the same cells in UL continued to grow. After P14, there was an upward inflection in growth.

Figure 3:
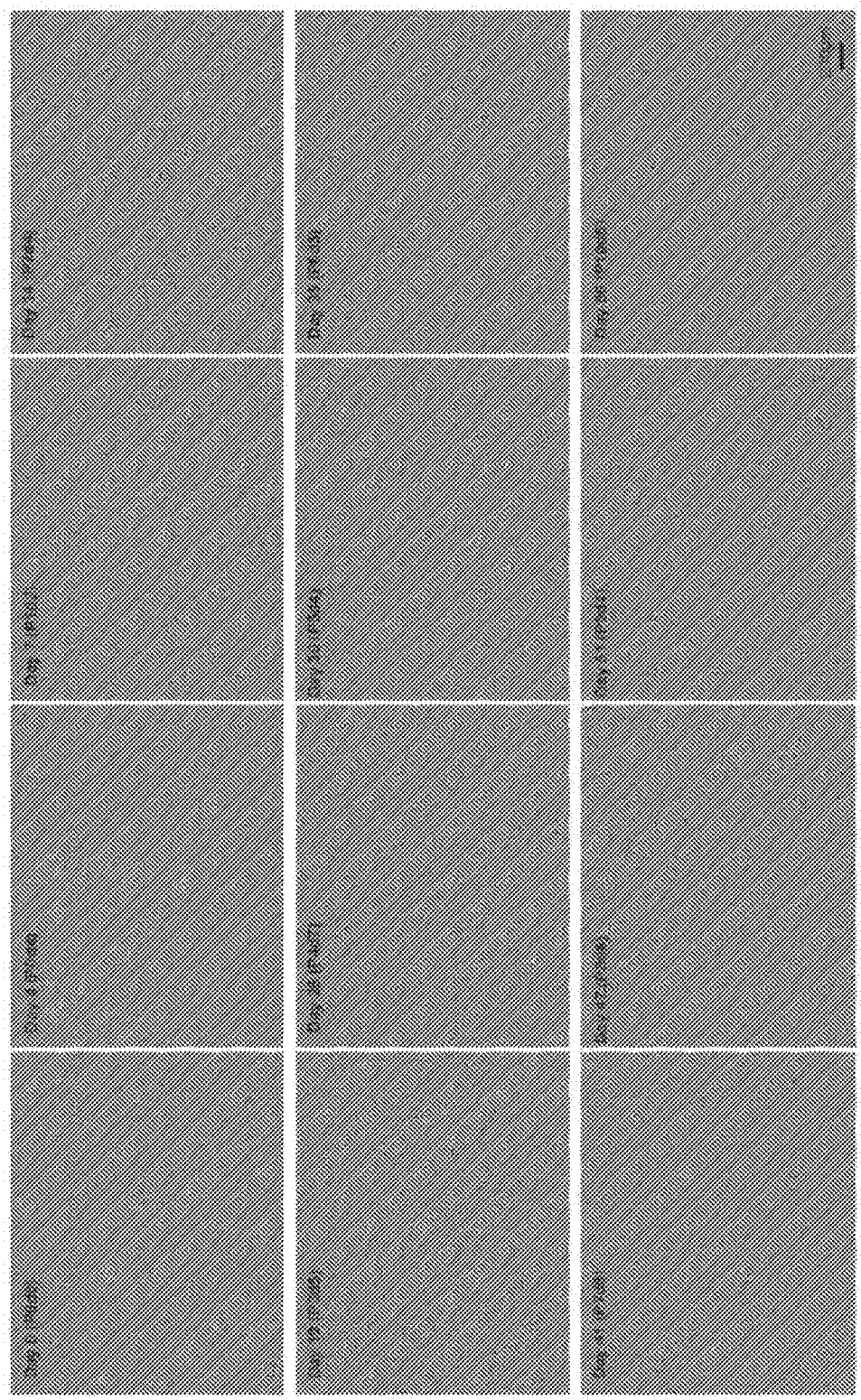
FIG. 3 shows the morphology of human RPCs (hRPCs) over time in culture (Day 0 to Day 56).

The morphology of human cells in FIG. 3 shows small clusters of cells that were seen initially, and which were systematically converted to adherent single cell cultures by end of the first week. This was accomplished by dissociation during the passaging procedure as described above. In general, initial use of small or medium-sized clusters promoted cellular viability, which was advantageous in the complete absence of serum. Subsequent complete dissociation, while maintaining relatively high cell density, can promote proliferation while avoiding differentiation.

Figure 4:
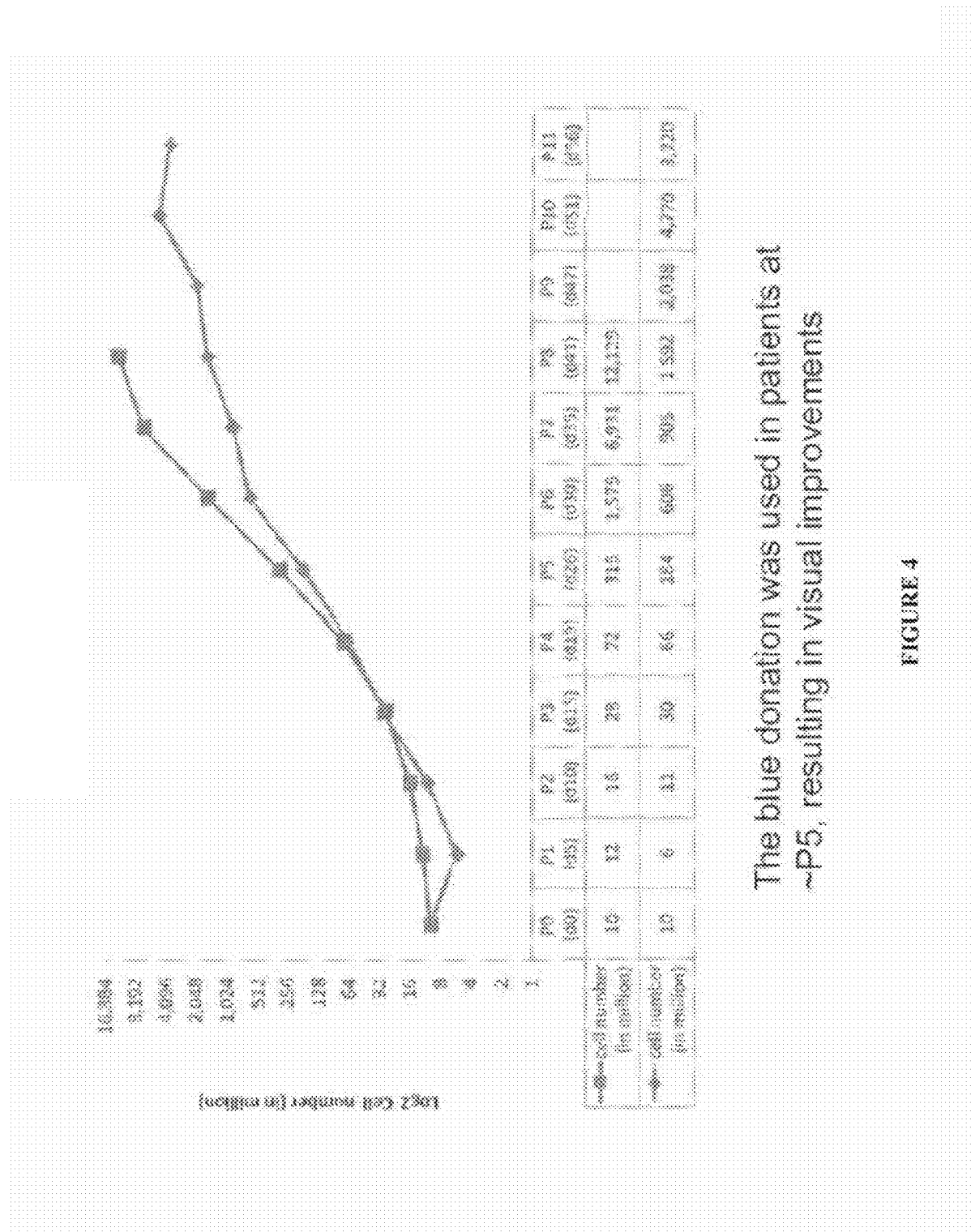
FIGS. 4 and 5 are graphs showing the growth kinetics of hRPCs over time.
Figure 5:
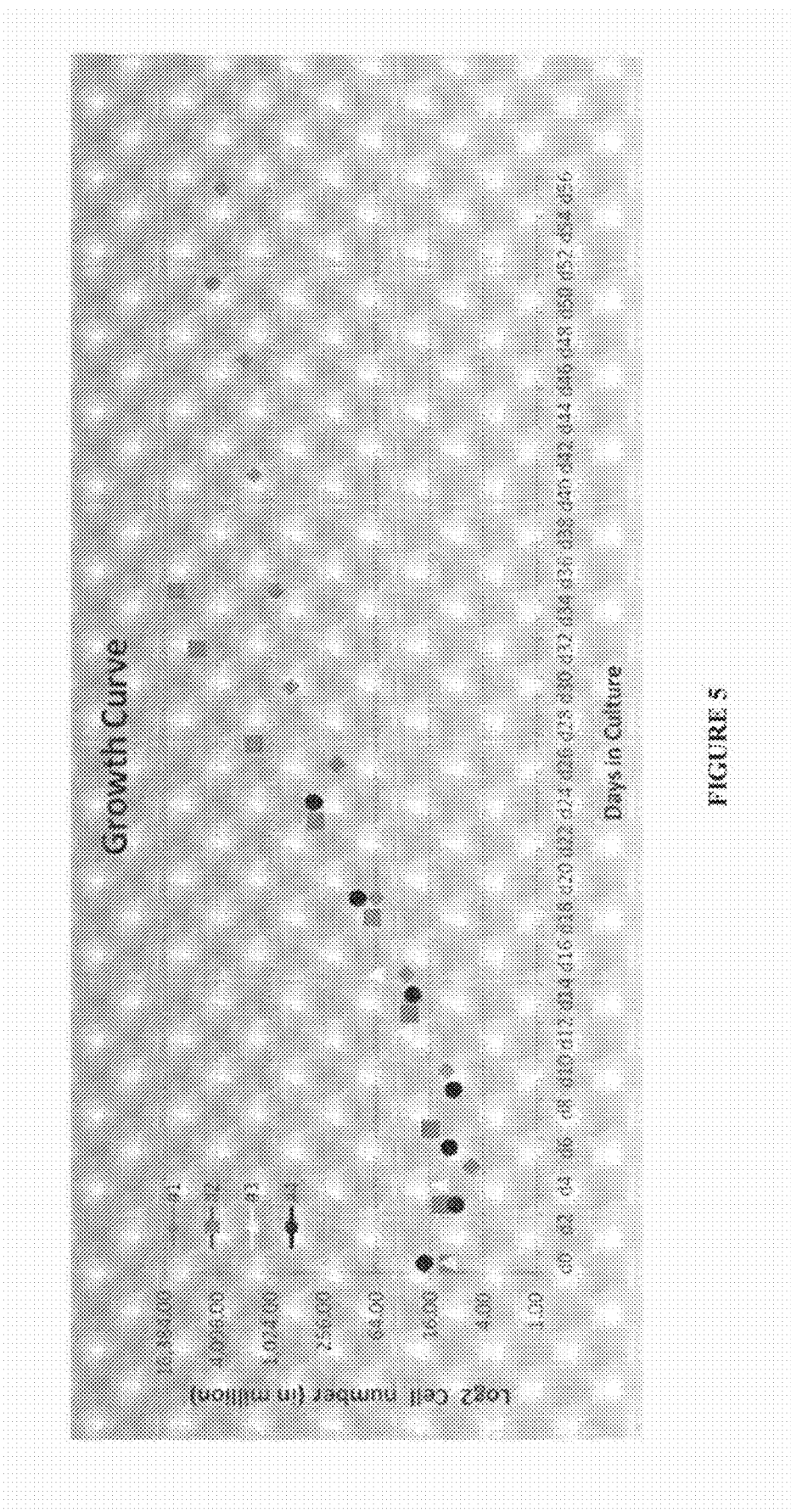

The growth kinetics of hRPCs are seen in FIGS. 4 and 5. Cells originating from donation were used clinically at P4. Growth seen under atmospheric oxygen is substantial, and was sustained for at least 10 passages (P10), yet growth was not indefinite. Unlimited growth characteristics are contraindicated as they may be indicative of pluripotency, immortalization and an increased risk of tumorigenesis.

Various serum- and xeno-free cell culture media were tested to determine the optimum condition for propagating RPCs, including DMEM/F12 (standard, Advanced and KnockOut; Invitrogen), Neurobasal (Invitrogen), Ultraculture (Lonza), and ReNcell (Chemicon). Cell culture media used in the culture of RPCs were sometimes supplemented with N2 supplement (Invitrogen), B27 (Invitrogen or other brand), Stempro (Invitrogen), vitamin C, albumin, recombinant human epidermal growth factor (EGF), basic fibroblast growth factor (bFGF), GlutaMAX I, L-Glutamine, and/or Penicillin-Streptomycin (Invitrogen) for first 2 weeks. "SM" as provided herein refers to standard growth medium based on DMEM/F12. "UL" is referred to herein as growth medium using Ultraculture as the base medium. Serum-free media was used in the absence of antibiotics or with antibiotics for first two weeks, followed by antibiotic-free media for about 6 weeks. No antifungal agents were used. FIG. 5 shows the results of experiments conducted to determine the optimum medium for RPCs. For base medium, standard DMEM/F12, a media supplemented with N2 Supplement, growth factors, glutamine or GLUTA-MAX™ (GlutaMax™), was compared with "Advanced DMEM/F12", supplemented in the same way. As seen in FIG. 6A, the "Advanced" version, which also contains supplemental vitamin C and albumin, proved more effective and increased yield of hRPCs by 18-29%.

The effects of cell culture supplementation were also explored. To that end, the N2 supplement was also compared with the B27 xeno-free supplement. FIG. 6B shows that supplementation with B27 xeno-free does increase yield of RPCs. N2 modestly increases yield, and those amounts are sufficient for therapeutic efficacy. The effects of additional vitamin C were also tested. A vitamin C supplement was added to the culture medium every two days. FIG. 7A shows that vitamin C does improve hRPC yield by approximately 30%. Although Advanced DMEM/F12 contains added vitamin C, it is evident that higher levels (0.05 mg/ml to 0.1 mg/ml) provided by additional supplementation are helpful for hRPC growth. Fresh vitamin C added every two days is sufficient; daily addition was not found to be necessary. Finally, supplementation with albumin was tested. Xeno-free human recombinant albumin was added to medium at 1.0 mg/ml and an enhancement of proliferation was observed (up to 27%) when added to standard DMEM/F12-based medium, but no detectable improvement was observed when additional albumin was added to Advanced DMEM/F12-based medium which is the favored base medium at this juncture (and already contains added albumin) See FIGS. 7B and 7C.

Figure 8:
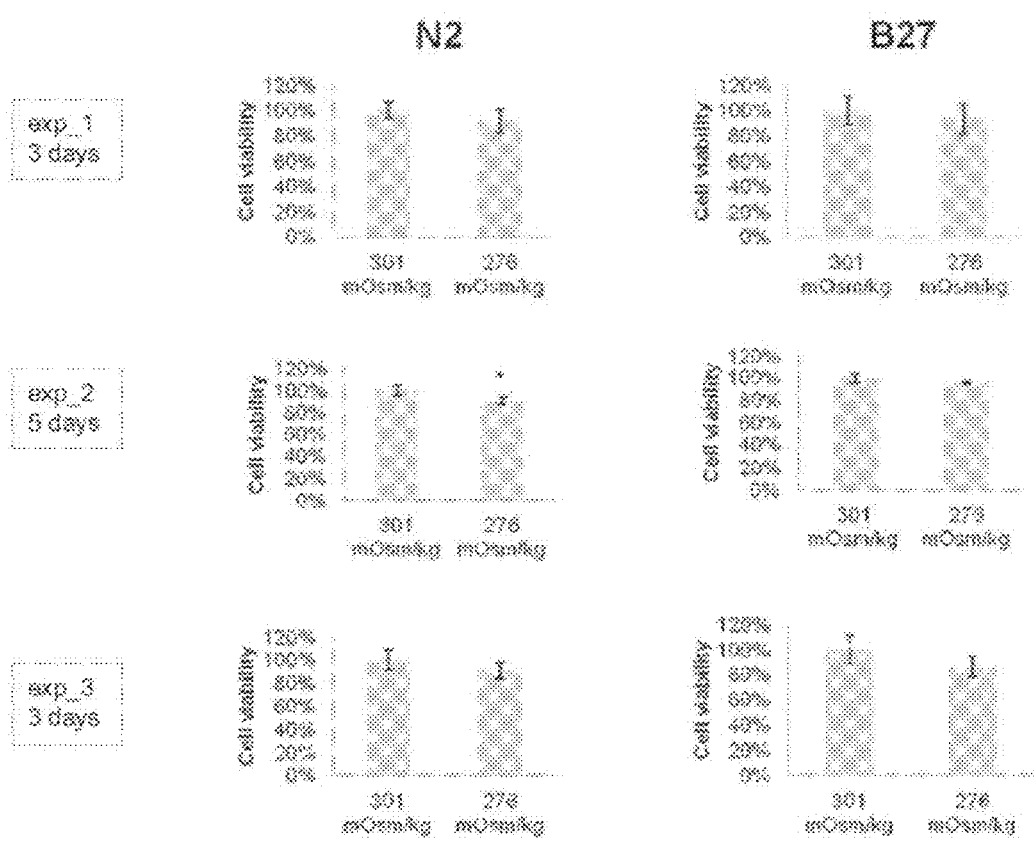
FIG. 8 reflects a comparison experiment testing differing osmolarity of cell culture media on hRPC growth and viability.

The osmolarity of the cell culture medium was also examined by using media of differing osmolarity (osm), in combination with different commercially available supplements. See FIG. 8. Low osm medium (KnockOut DMEM/F12; 276 mOsm/kg) was not beneficial with the commonly used neural supplements N2 or B27, and in some cases resulted in significantly less yield in comparison to normal osm medium (DMEM/F12; 300-318 mOsm/kg). There were indications of a benefit for low osm if a less common supplement was used in combination (STEMPRO™ kit, Invitrogen, data not shown).

In addition to % viability and proliferation rate, an additional metric that presages optimal (e.g., in vitro) outcome of initial harvest was developed, referred to herein as the "time-to-drop". "Time-to-drop" refers specifically to the time for the dissociated cells to settle to bottom of flask in incubated growth medium. Retention in suspension (lack of drop) can be associated with cellular injury or non-viability resulting from the trauma of the isolation process and that successful self-repair by cells is associated with observed ability to restore membrane homeostasis, normal osmolarity, etc and thereby regain negative buoyancy and thus "drop." Delayed self-repair is stressful to cells and results in less active/healthy cultures. Using an approximately 90% drop (based on % of population) as reporting criterion, a ~6 hour drop time for cells from tissue with 21.5 hour transportation time was observed, shortening to approximately 1.5 hour for cells from tissue with 4.5 hour transport time. Cat RPC and brain progenitor cells which were plated immediately resulted in a 1 hour drop time. Drop times of approximately 1 hr or less were achievable with human cells.

Figure 9:
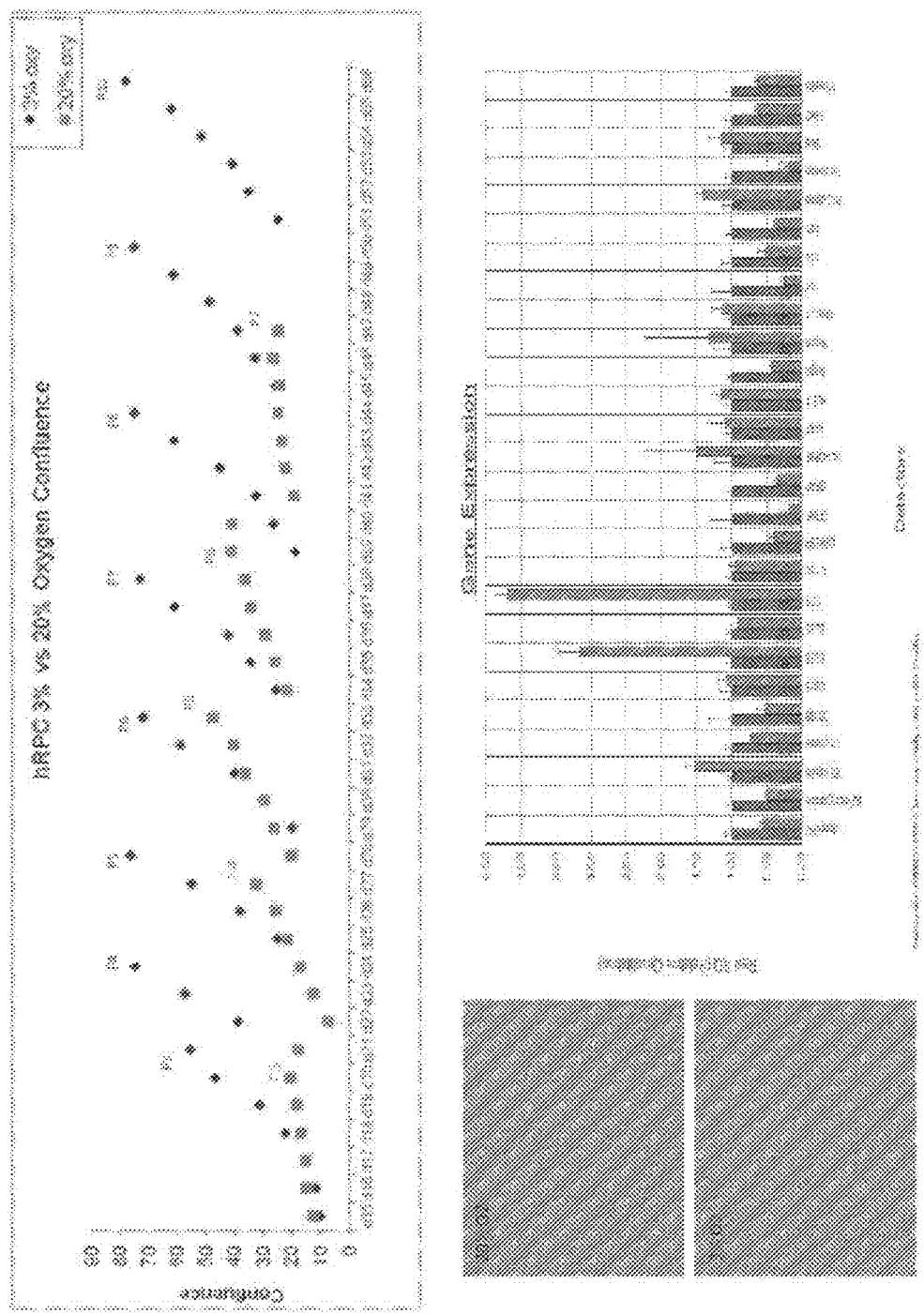
FIGS. 9-11 represent results of experiments where hRPCs were cultured under conditions of atmospheric oxygen and compared to the same cells grown under low oxygen conditions. Growth dynamics, morphology, and gene expression were evaluated.
Figure 10:
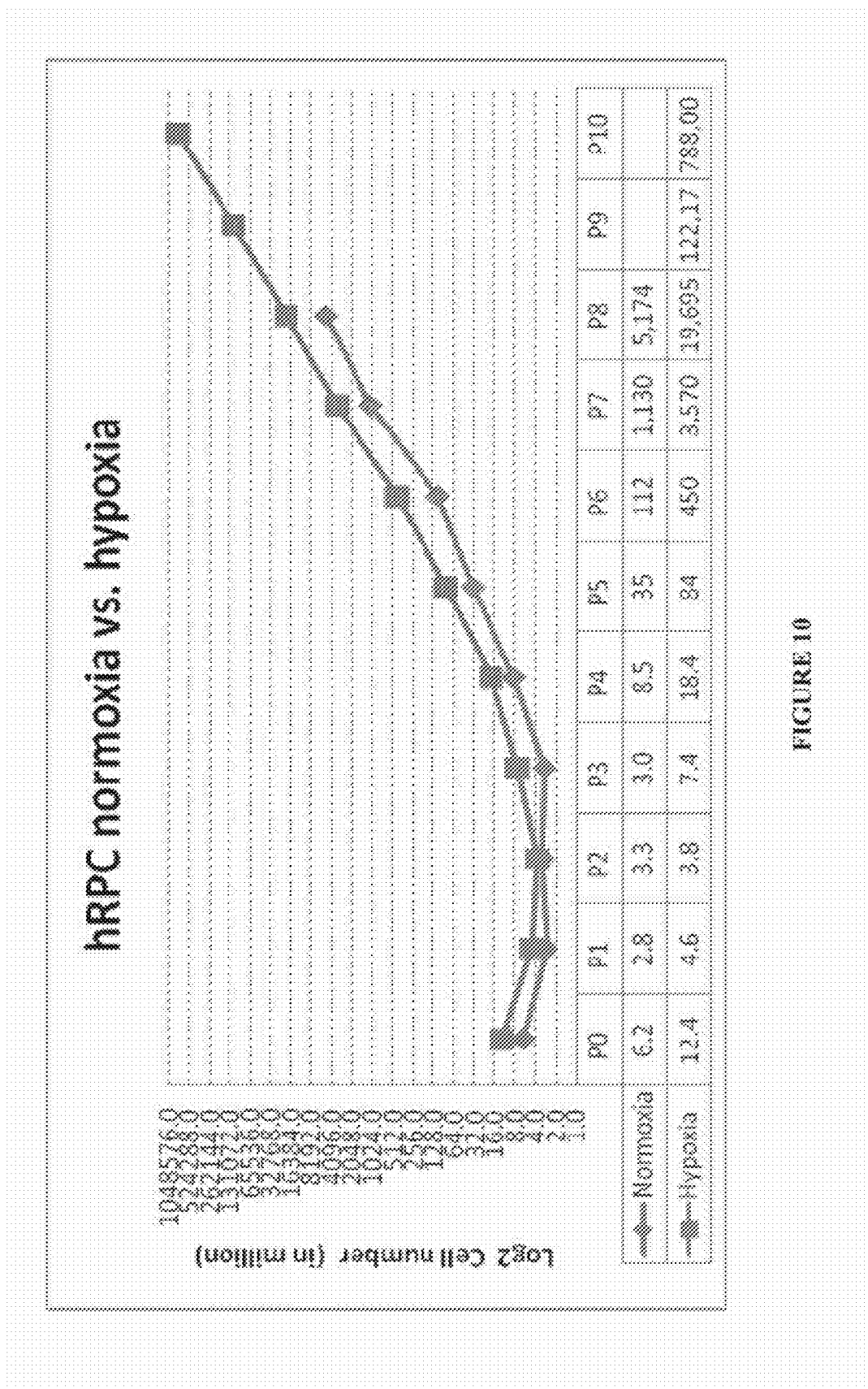
Figure 11:
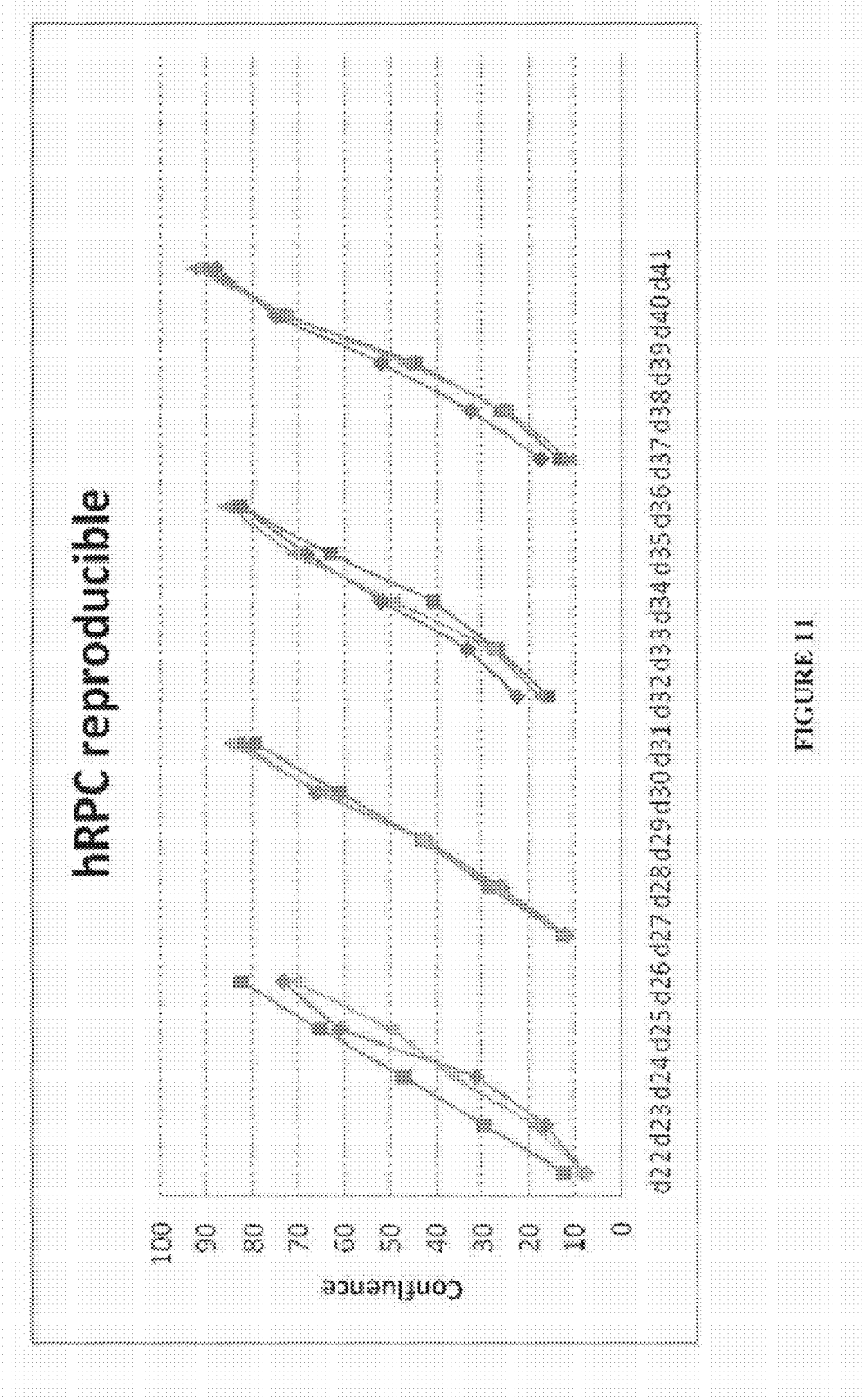

Cells used to demonstrate visual improvement in human with RP were cultured under conditions of atmospheric oxygen. The ramifications of growing RPCs under low oxygen conditions that more closely mimic oxygen levels of developing fetal retina during gestation, in this case 3% oxygen ("lowOx") were explored. As FIG. 9 shows, 3% oxygen ("lowOx") markedly improved proliferation of hRPCs as well as more sustained proliferation (at day 56, P10) and greatly increased overall cell yield from a given donation. Growth characteristics under atmospheric oxygen (20%) are shown for comparison and reveal notably less vigorous proliferation rate as well as earlier senescence of growth (day 47, P7) and inferior total yield. FIG. 9 also shows an inflection point corresponding to an acceleration of growth of hRPCs in lowOx that occurs at a confluence level of about 40%, emphasizing the importance of high density culture conditions for optimal hRPC growth. Similar results are seen in cells grown under hypoxic conditions (FIG. 10). The growth characteristics of WCB cells grown under hypoxic conditions were reproducible (FIG. 11).

Figure 12:
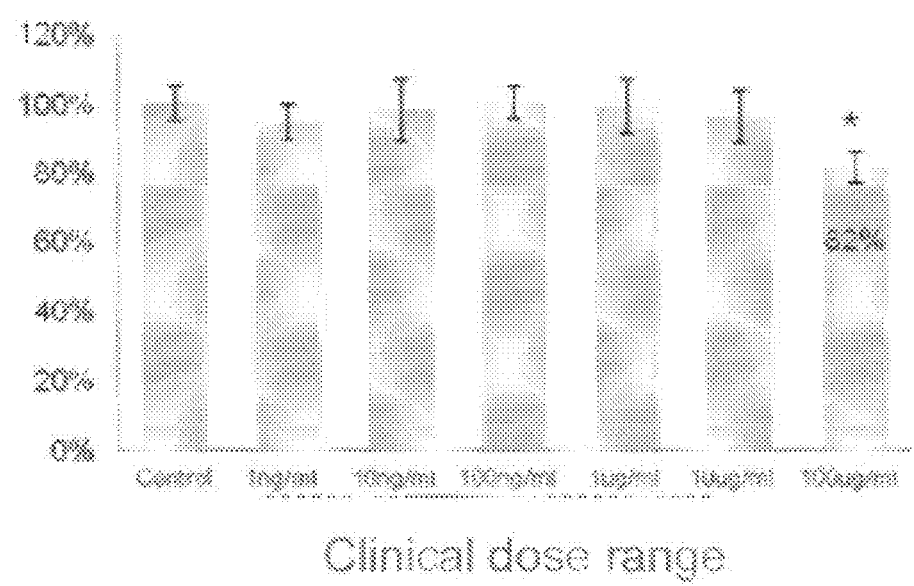
FIG. 12 shows the results of a steroid toxicity test performed on hRPCs.

The cells were also subjected to a steroid toxicity test, since steroids are often used in patients at the time of transplantation. FIG. 12 shows toxicity to hRPC of the steroid triamcinolone acetonide, which is commonly used in ophthalmic applications, but only at levels beyond anticipated clinical usage. Clinical doses of triamcinolone acetonide did not appear to affect cell proliferation, but high doses (about >10 times the expected clinical dose) may decrease donor cell viability.

Figure 13:
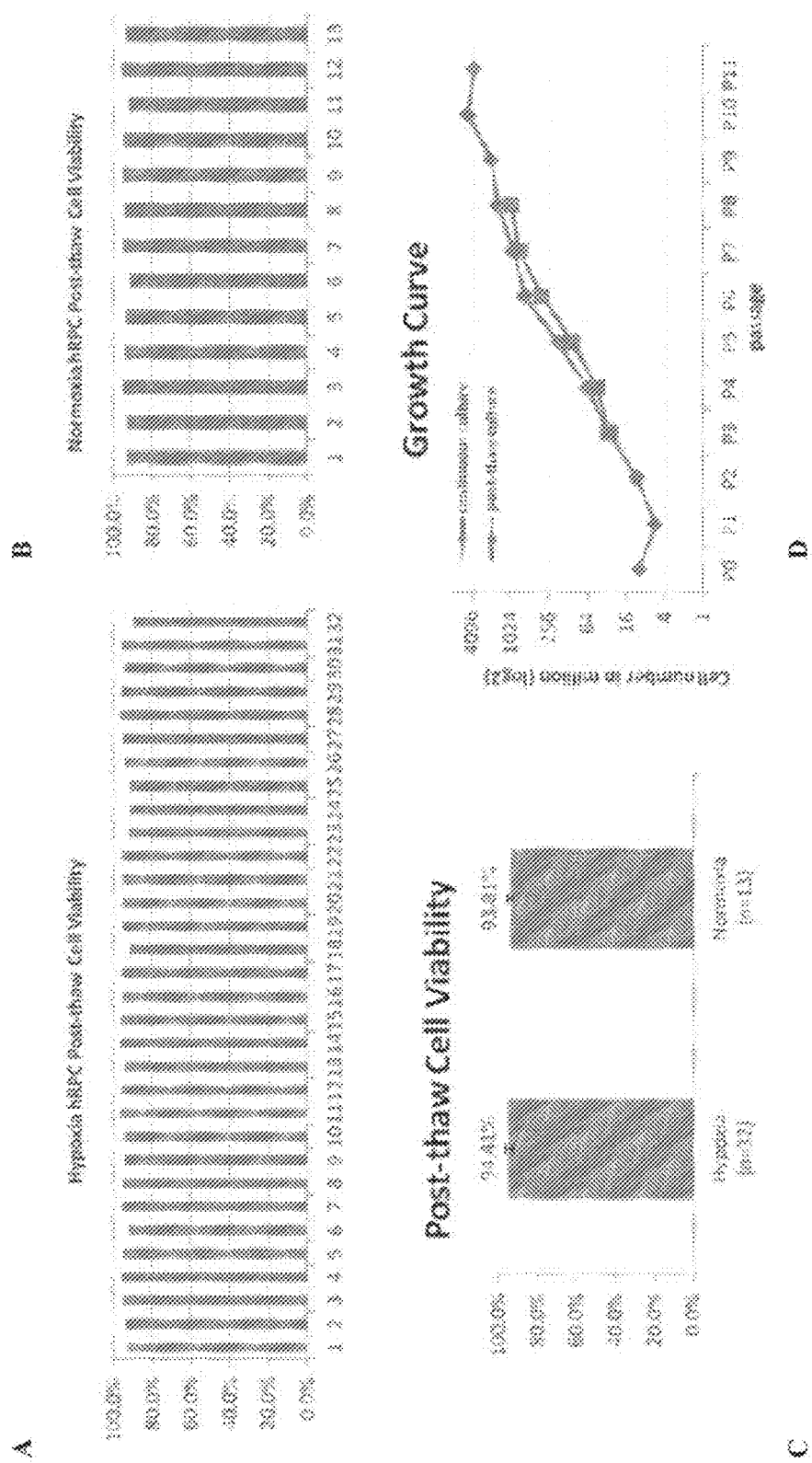
FIGS. 13A-13D are graphs showing the viability and stability of previously frozen hRPCs.

Cells previously frozen in liquid nitrogen were thawed and tested for viability. FIG. 13 shows the results of a freeze-thaw experiment. These previously frozen cells were viable under both hypoxic and normoxic cell culture conditions. Viability of the cells was found to be approximately 94% for both oxygen conditions. Post-thawed cells displayed growth kinetics similar to hRPCs maintained under continuous culture conditions.

Example 2

Characterization of RPCs

Immunocytochemistry

Cells were dissociated and grown on 4 or 8-well chamber slides for 1-3 days, then fixed for 15 minutes in 4% paraformaldehyde and washed 3 times in PBS. The slides were blocked in a solution containing 5% donkey serum and/or 0.3% Triton X-100 for 1 hour, followed by another PBS wash. A panel of antibodies was then incubated overnight at 4° C. to detect antigens expressed by progenitor cells. These included anti-Nestin (Chemicon 1:200), anti-vimentin (Sigma 1:200), anti-Sox2 (Santa Cruz 1:400), anti-SSEA-1 (BD 1:200), anti-GD2 (Chemicon 1:100), anti-Ki-67 (BD 1:200), anti-$\beta$3-tubulin (Chemicon 1:400), anti-GFAP (Chemicon 1:400), and anti-GDNF (Santa Cruz 1:200). This was followed by incubation with anti-mouse Alexa 546 (Invitrogen 1:400), anti-goat Alexa 488 (Invitrogen 1:400), or anti-rabbit FITC (Chemicon 1:800) secondary antibodies. Fluorescence was detected using Leica converse microscopy and visualized by Metamorph software. Percentage positive profiles were calculated by counting those profiles expressing specific immunoreactivity in 6 randomly selected fields, with DAPI used to determine total cell number.

RNA Extraction

Total RNA was extracted by using an RNeasy Mini kit (Qiagen, CA, USA) following the manufacturer's instructions and treated by DNase I. RNA was quantified by spectrophotometer (ND-1000; NanoDrop Technologies Inc., Wilmington, Del.) by measuring optical density (OD) at 260 nm/280 nm 1.90-2.10 and 260 nm/230 nm 1.90-2.20.

Microarray Analysis

All starting total RNA samples were quality assessed before beginning the target preparation/processing steps by running a small amount of each sample (typically 25-250 ng/well) onto a RNA 6000 Nano LabChip that was evaluated on an Agilent Bioanalyzer 2100 (Agilent Technologies, Palo Alto, Calif.). Double stranded cDNA was synthesized from the poly(A)+mRNA present in the isolated total RNA using the GeneChip WT cDNA Synthesis Kit (Affymetrix, Inc., Santa Clara, Calif.) and random hexamers tagged with a T7 promoter sequence. Typically, 100 ng of total RNA starting material was used for each sample reaction. The double stranded cDNA was then used as a template to generate many copies of antisense cRNA from an in vitro transcription reaction for 16 hours in the presence of T7 RNA polymerase using the Affymetrix Genechip WT cDNA Amplification Kit. Ten micrograms of cRNA were used in a second-cycle cDNA reaction with random hexamers that were reverse-transcribed to produce single stranded DNA in the sense orientation.

The single stranded DNA sample was fragmented (WT Terminal Labeling Kit, Affymetrix) to an average strand length of 60 bases (range 40-70 bp) following prescribed protocols (Affymetrix GeneChip WT Sense Target Labeling Assay Manual). The fragmented single-stranded DNA was subsequently labeled with recombinant terminal deoxynucleotidyl transferase and the Affymetrix proprietary DNA Labeling Reagent, which is covalently linked to biotin. Following the recommended procedure, 0.54 μg of this fragmented single-stranded target cDNA was hybridized at 45° C. with rotation for 17 hours (Affymetrix GeneChip Hybridization Oven 640) to probe sets present on an Affymetrix human-gene 1.0 ST array. The GeneChip arrays were washed and then stained with streptavidin-phycoerythrin on an Affymetrix Fluidics Station 450 (Fluidics protocol FS450_007). Arrays were scanned using the GeneChip Scanner 3000 7G and GeneChip Operating Software v1.4 to produce CEL intensity files.

Normalization was performed using the probe logarithmic intensity error (PLIER) estimation method, which includes a quantile normalization protocol within the associated software algorithm. Briefly, the probe cell intensity files (*.CEL) generated above were analyzed using Affymetrix Expression Console software v1.1 using the PLIER algorithm to generate probe-level summarization files (*.CHP). The algorithm used was from PLIER v2.0 (quantification scale: linear; quantification type: signal and detection p value; background: PM-GCBG; normalization method: sketch-quantile). Microarray data was then evaluated using JMP Genomics 4.1 (SAS Americas). The data was analyzed by one-way ANOVA with a post hoc t-test and the resulting p-values corrected using an FDR $\alpha<0.05$. The resulting data table was annotated. The JMP software was also used to generate a Principal Component Analysis, a Venn diagram, as well as a hierarchical cluster and heat map, using the default fast Ward's method, in addition to volcano plots from the ANOVA results.

Real-Time qPCR Assay

Selection of candidate markers was based on the results of previous work with cells of this type, together with potential relevance to the current study. Particular emphasis was placed on markers associated with immature cells of neural lineage, as well as selected markers for neural and glial differentiation. Two micrograms of total RNA from the sample preparation was reverse transcribed with Omniscriptase Reverse Transcriptase kit (Qiagen, CA, USA) and 10 μM random primers (Sigma, MO, USA) according to the manufacturer's instructions. Quantitative PCR was performed using a 7500 fast Real-Time PCR System (Applied Biosystems, Irvine, USA) using Power SYBR green (Applied Biosystems, Irvine, USA) or Taqman gene expression assay (Applied Biosystems).

Resolution of the product of interest from non-specific product amplification was achieved by melting curve analysis when using the SYBR green method. β-Actin or GDNPH were used as endogenous controls to normalize gene expression. The following general real-time PCR protocol was used: denaturation program (95° C. for 10 minutes), quantification program (95° C. for 15 seconds and 60° C. 1 30 min) repeated 40 cycles, melting curve program (95° C. 15 sec and 60° C. 1 min with continuous fluorescence measurements), and finally a cooling program at 40° C. Each reaction was performed in triplicate. Graphs were plotted and analysis was performed by the $\Delta\Delta C_t$ method (7500 Fast system software 1.4 and DataAssist 2.0, Applied Biosystems, Irvine, USA) and JMP software 4.1 (SAS Americas). All data points are expressed as mean±standard Error (SE). Statistical difference was determined using t-test. Data were considered significant when $p<0.05$.

Cytotoxicity Study

Cell Counting Kit-8 (CCK-8; Dojindo Molecular Technologies Inc., Gaithersburg, Md.) was used to determine cytotoxicity of RPCs. The kit uses WST-8, which, upon bioreduction in the presence of the electron carrier 1-methoxy PMS, produces a water-soluble colored formazan. Ninety-six well plates containing 90 µl of cell suspension per well were inoculated with 10 µl of CCK-8 prepackaged solution. The plates were incubator for 2 hours and the $OD_{450}$ of the supernatant was measured. Each experiment was performed in quadruplicate on at least three separate experiments.

Figure 14:
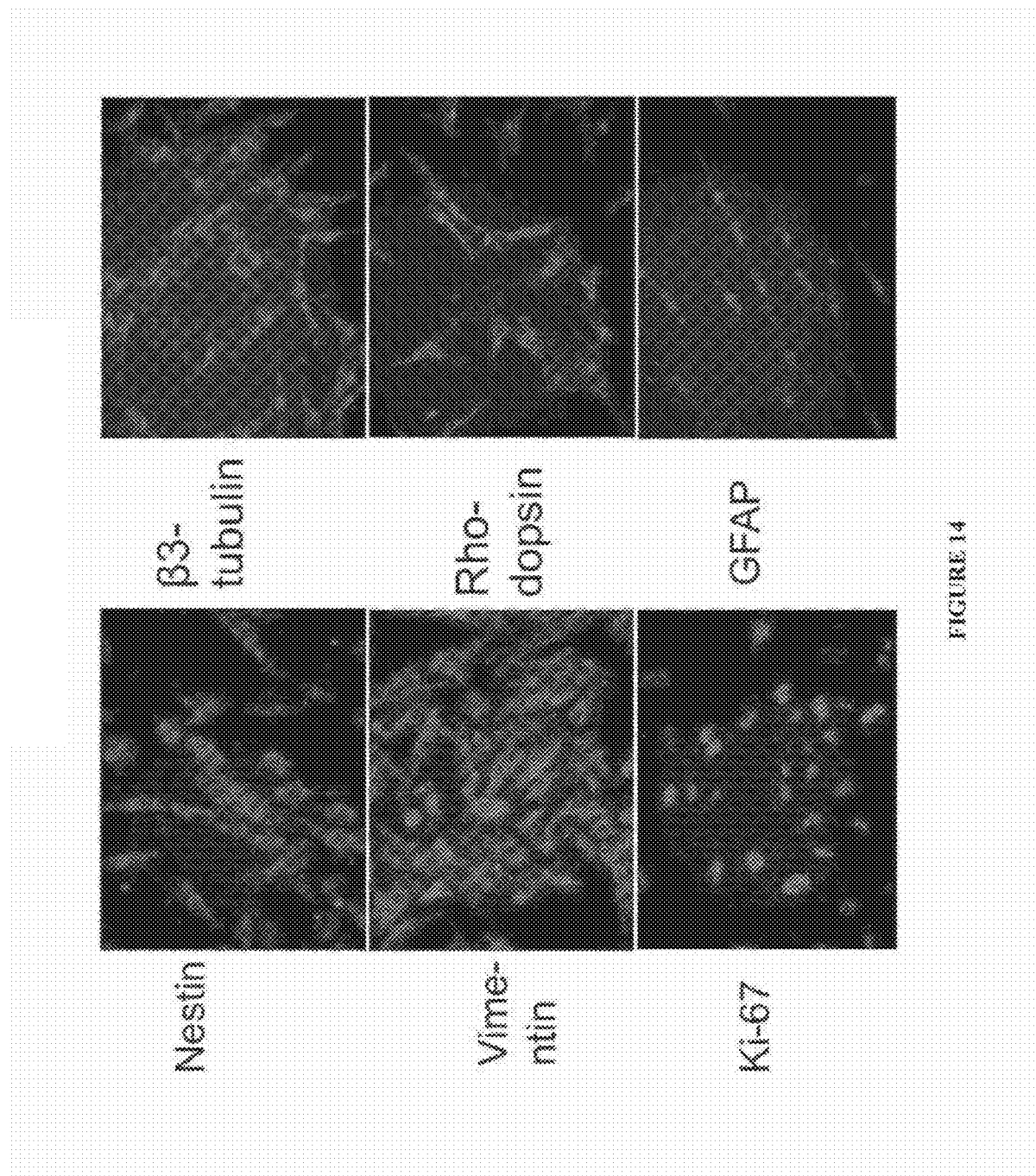
FIG. 14 shows feline RPCs stained by ImmunoCyto-Chemistry (ICC) markers nestin, β3-tubulin, vimentin, rhodopsin, Ki-67, and GFAP.
Figure 16:
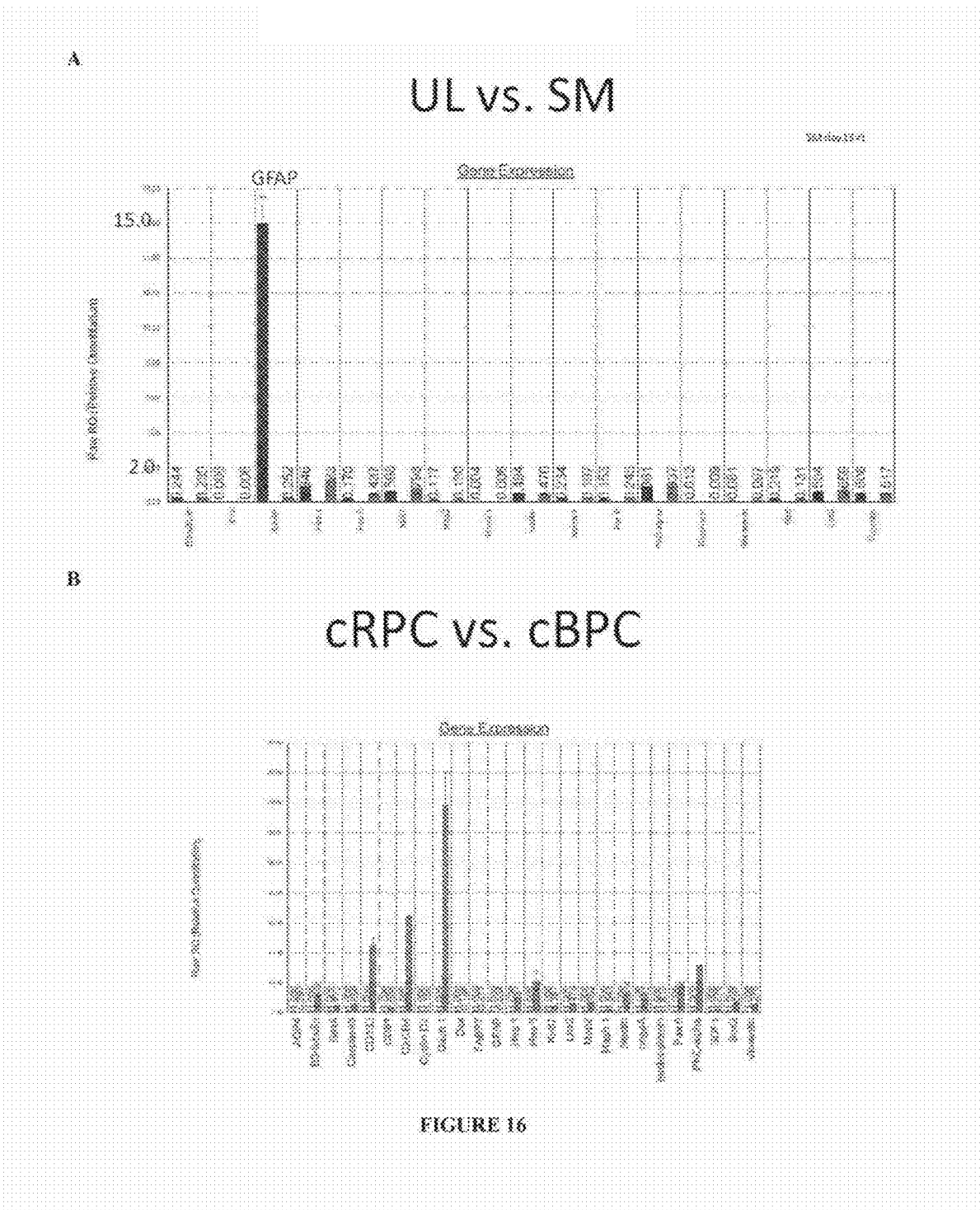
FIG. 16B is a graph illustration of differences in gene expression by qPCR measurement comparing feline RPC versus brain progenitor cells (BPCs).

Feline RPC cells stained by ImmunoCytoChemistry (ICC) markers showed high levels of expression of vimentin. See FIG. 14. The same was observed in human RPCs. Lineage markers including nestin, vimentin, Ki-67, β3-tubulin, glial fibrillary acidic protein (GFAP), and rhodopsin revealed the presence of neurons, photoreceptors, glia and demonstrate the retained multipotentiality and heterogeneity of RPCs cultures. The feline RPC genetic profile was observed over time using qPCR of marker transcripts. Dynamic changes in expression profile: general trend of downward quantitative changes in marker expression with time in culture, as also seen with human RPCs. See, e.g., FIG. 15. Gene expression was also compared between UL and SM cell culture media conditions by qPCR (FIG. 16A). Because proliferation of feline progenitors (both RPC and BPC) was not sustained well in SM cultures, an investigation was made into comparative gene expression. With SM day 13 used as baseline for comparison (set to "1.0"), feline RPCs grown in SM and UL were compared at culture Day 31. Most markers examined showed decreased expression over time in culture, however the SM culture showed marked elevation in GFAP expression, consistent with progressive loss of multipotency and tendency toward restriction along the glial lineage. Cells in UL media did not show this.

Feline RPC versus brain progenitor cells (BPCs) were also compared. See FIG. 16B. Feline RPCs showed relatively increased expression of some markers relative to BPCs; these included Dach1, Lhx2 and Pax6, which are transcription factors involved in retinal specification and development, as well as the transcription factors Hes1 and Hes5, also involved in retinal development. CD133, nestin, Sox2, vimentin are general CNS progenitor markers, while β3-tubulin, Map2, and PKCα are lineage markers.

Figure 17:
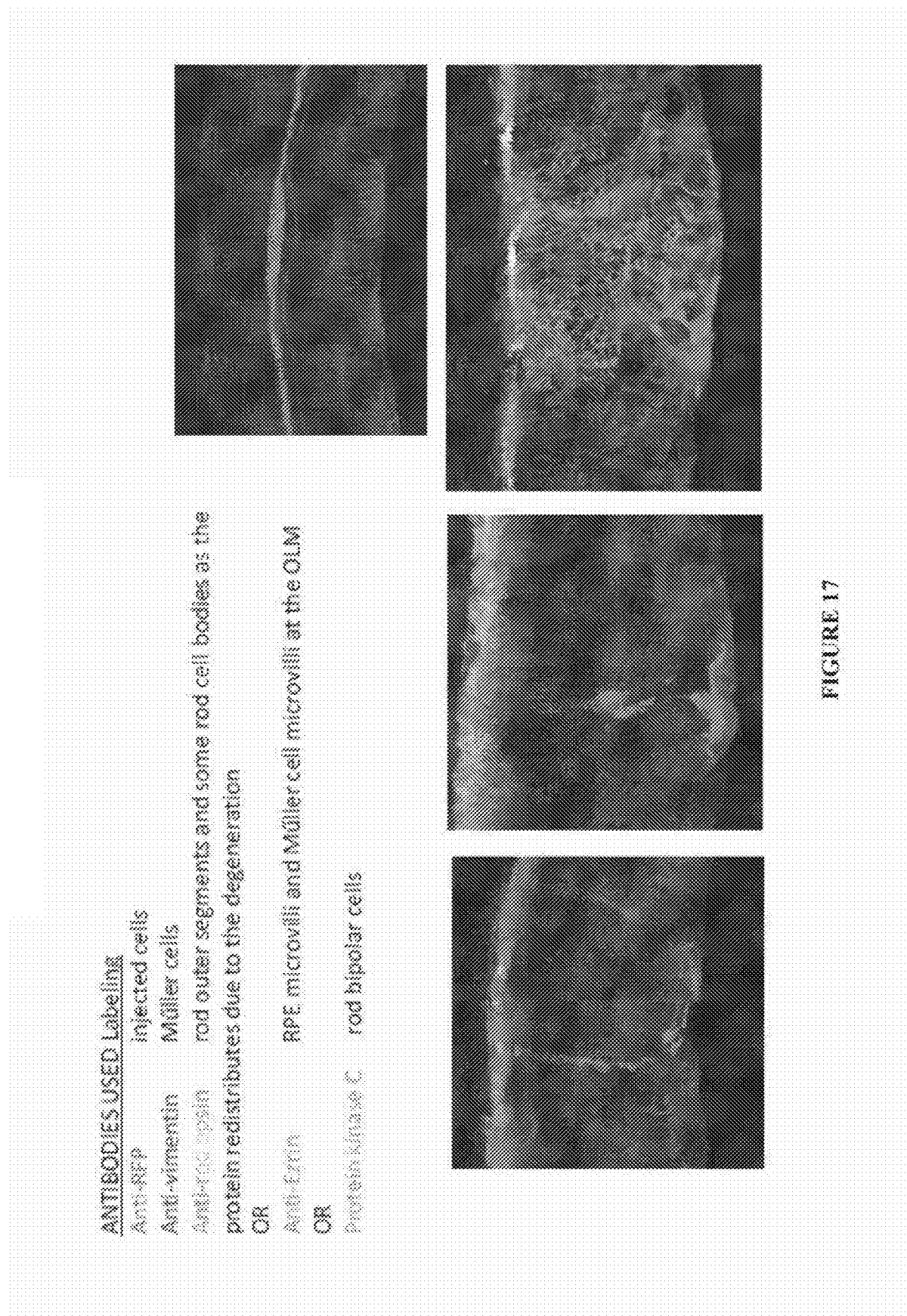
FIG. 17 shows cell staining of RFP, vimentin, or opsin, ezrin or PKC after in vivo transplantation of feline RPCs in the subretinal space of dystrophic Abyssinian cats.

Feline RPCs were transplanted to the subretinal space of dystrophic Abyssinian cats and isolated post-transplantation cells subjected to staining See FIG. 17. The cells survived transplantation to the subretinal space and in addition showed the ability to migrate into the recipient retina. Engrafted cells showed an ability to differentiate into what appear to be Mueller glia, both morphologically and by vimentin labeling. Mueller cells are glia that are specific to the retina and that extend across the full thickness of the retina to provide structural stabilization. They are important to numerous retinal functions, including neuronal survival.

Figure 18:
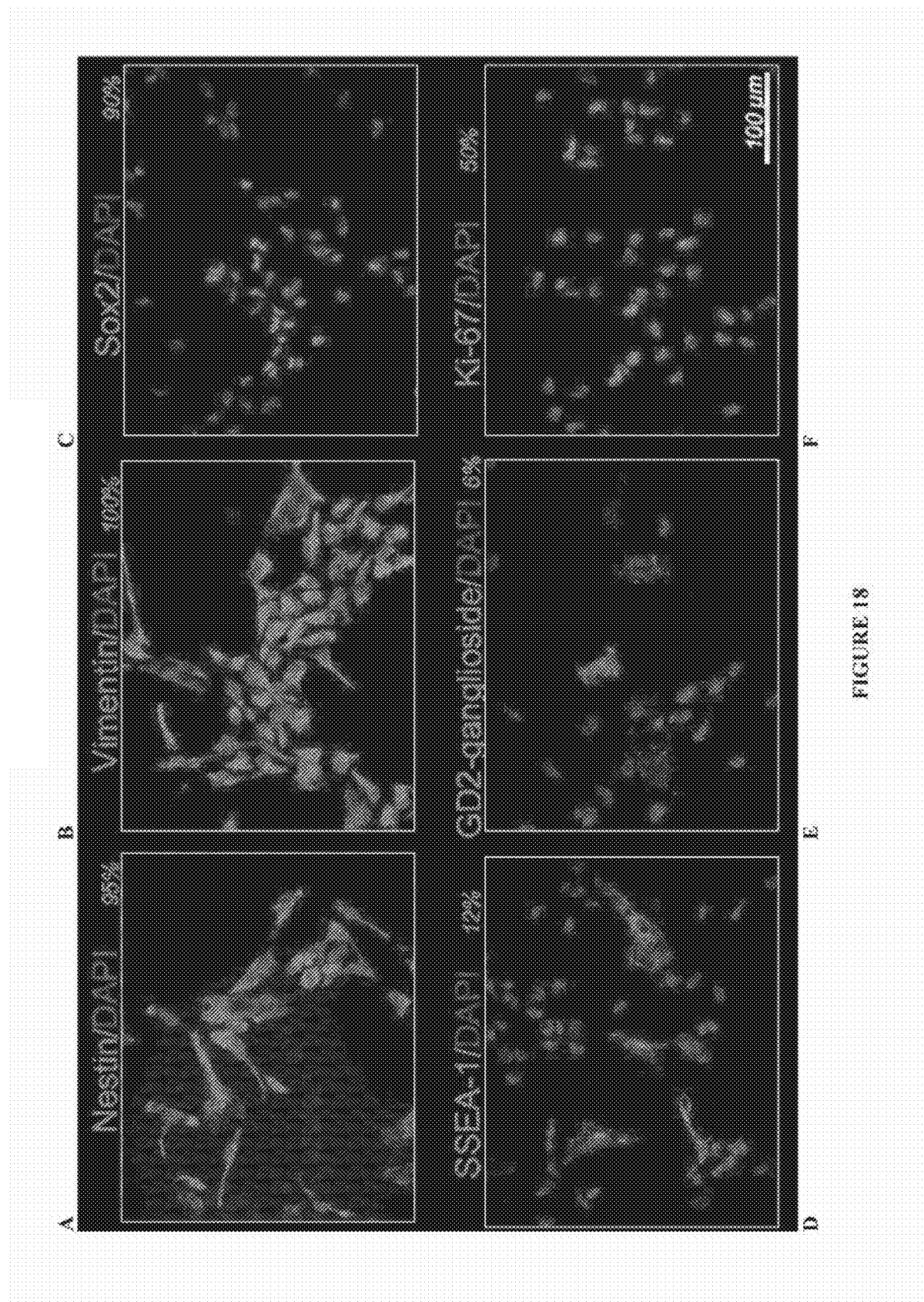
FIG. 18 illustrates the morphology of human cells using marker expression by ICC. The markers include: (A) nestin; (B) vimentin; (C) Sox2; (D) SSEA-1 (also known as CD15, LeX); (E) GD2-ganglioside; and (F) Ki-67.
Figure 19:
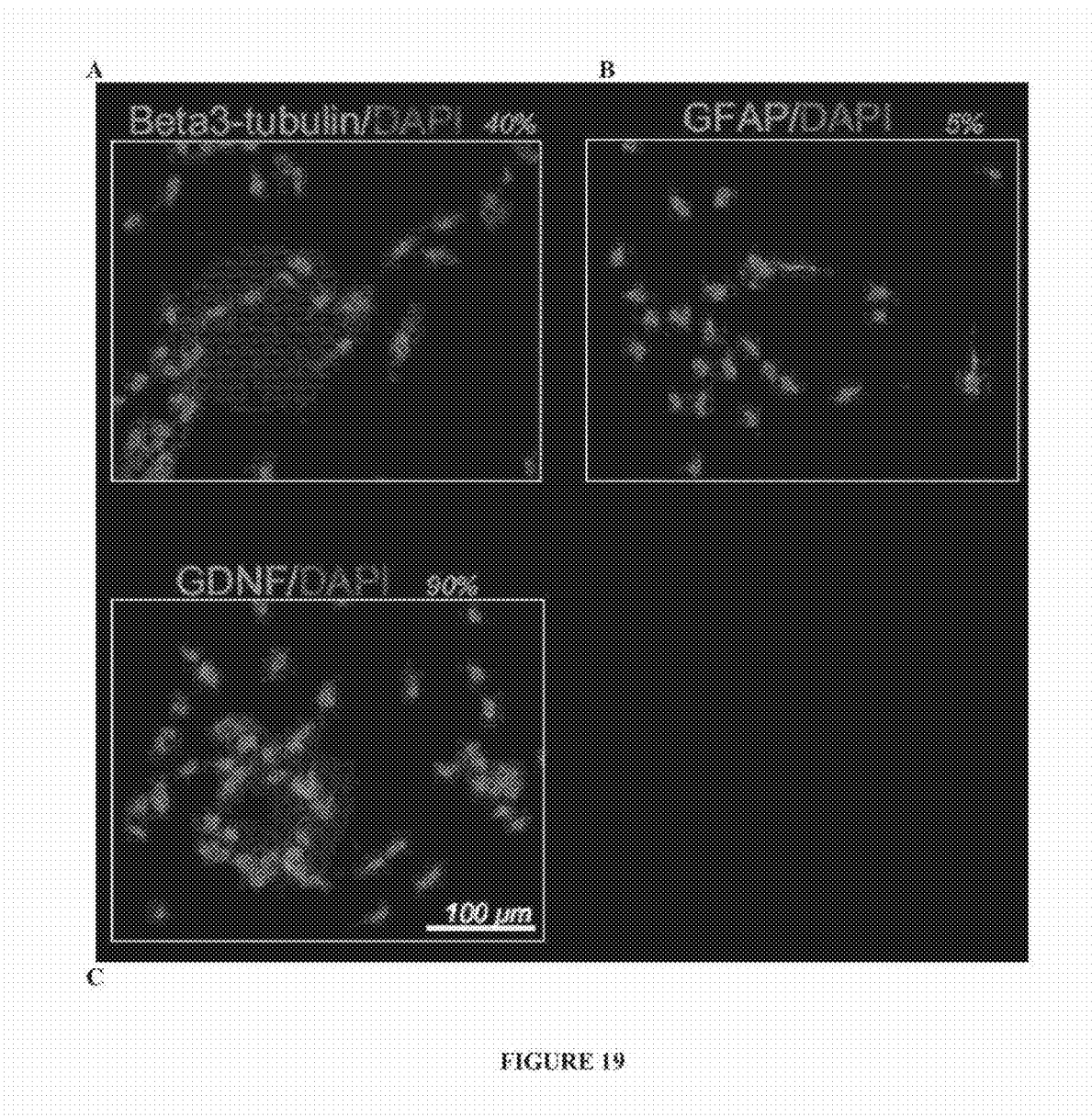
FIG. 19 illustrates the morphology of human cells using marker expression by ICC. (A) shows β3-tubulin staining; (B) GFAP staining; and (C) GDNF staining.

The morphology of human RPCs using marker expression by ICC was determined FIGS. 18 and 19 show the percentage of expression of certain key markers within the cultured population. Nestin expression was confirmed and is believed to be associated with neural stem/progenitor cells and RPCs. Vimentin was very heavily expressed by this population, although its expression was believed to be non-specific to RPCs. Sox2 is transcription factor also associated with neural development and was also present in hRPCs. SSEA-1 (also known as CD15, LeX) has been associated with pluripotency in ES cells; studies have showed expression of this marker by subset of multipotent brain and retinal progenitors (RPCs), which are not pluripotent. Expression of GD2-ganglioside was also seen in hRPCs. Ki-67 is marker of active proliferation and was used to confirm that the cells of this embodiment are proliferative and mitotically active at the time of clinical use. The presence of this marker distinguishes hRPCs from populations of post-mitotic precursors (Surani, M. A. and McLaren A. (2006) Nature 443(7109): 284-285). Ki-67 in the relative absence of OCT4 expression distinguishes RPCs from mitotically active pluripotent stem cells (ES, iPS), which are unsafe for transplantation unless subjected to further differentiation. The level of Ki-67 activity also allowed monitoring of the quality (health and suitability) of the isolated hRPC cultures. β3-tubulin is a marker of neuronal development and was found to be expressed at moderate levels in the cultures, suggestive of neural lineage determination and the potential for differentiation into neurons. Since neuron formation tends to be lost at high passage numbers, expression of this marker may confirm the retention of multipotency by the cultures. GFAP is a marker generally associated with glial differentiation, particularly astrocytes, although it is also expressed by retinal Mueller cells following a variety of perturbations or in culture. Again, the low percentage of GFAP expression seen is suggestive of the rate of spontaneous differentiation into glial cells and helps us confirm the retention of multipotency by the cultures, however GFAP is also known to be expressed by immature progenitors as well. GDNF is a neurotrophic factor associated with rescue of neurons, including photoreceptors, in some animal models and the hRPC populations isolated as described herein can express this factor by ICC, however negative ELISA data indicate that the factor is not necessarily secreted. Additional factors are likely to be more important to RPC-mediated photoreceptor rescue.

Figure 20:
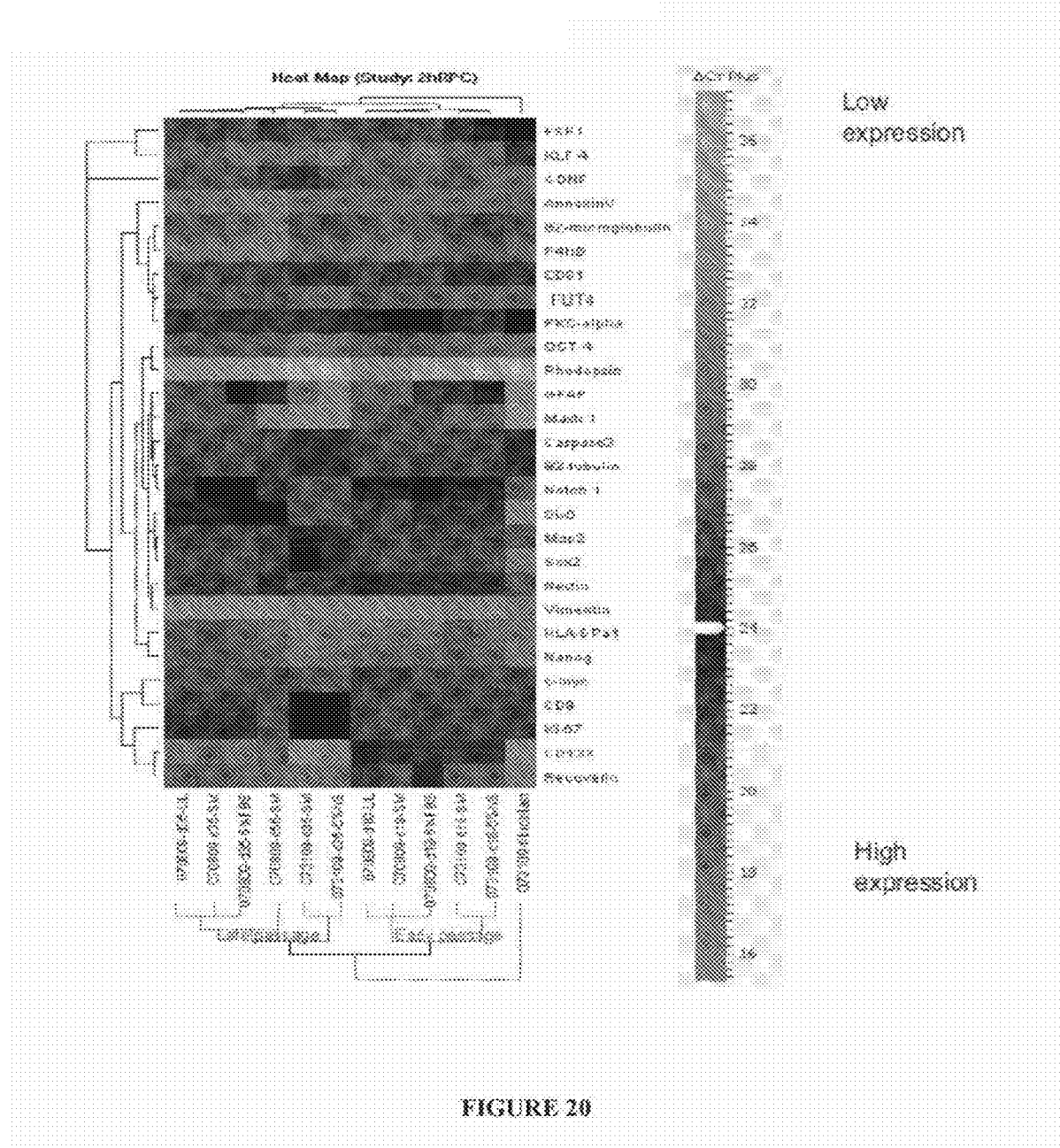
FIG. 20 depicts marker expression at the RNA level, as detected by quantitative PCR heat mapping.
Figure 21:
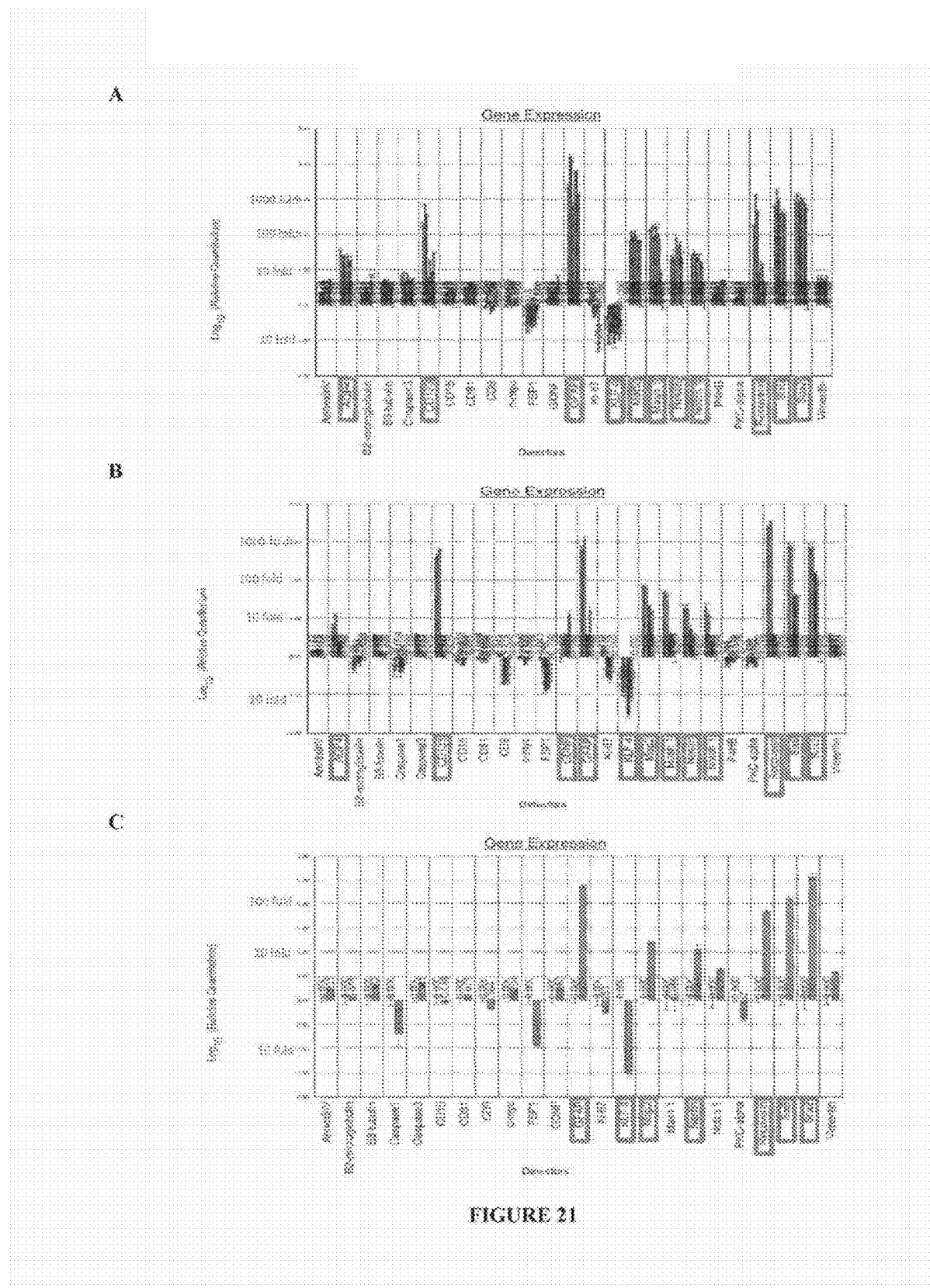
FIGS. 21A-21C show the results of a qPCR experiment comparing hRPC versus hFB and expanding marker detection.

Notably, hRPCs can be distinguished from fibroblasts (hFB) as shown by marker expression at the RNA level. See FIG. 20, which shows a qPCR heat map demonstrating that vimentin is a marker that is very highly expressed by hRPCs but not fibroblasts, and additionally reveals dynamic changes in relative profile expression with time in culture. FIGS. 21A-21C show the results of a qPCR experiment comparing hRPC versus hFB and expanding marker detection. Multiple genes are identified that are higher in RPC (AQP4, CD133, GFAP, MAP2, MASH1, nestin, Notch1, recoverin, SIX6, SOX2, and 1 (KLF4) that is lower (therefore higher in hFB). Expression levels vary with time in culture, but the relative predominance between cell types appears fairly consistent. FIG. 22 contains a list of 11 genes (from the profile of approximately 26 used) that exhibit consistent behavior (in hRPC vs. hFB) between different donations. Genes consistent across all 3 donations are highlighted in yellow, and are as follows KLF4 (RPC<FB); and GFAP, MAP2, nestin, recoverin, SIX6, and SOX2 (RPC>FB).

Figure 23:
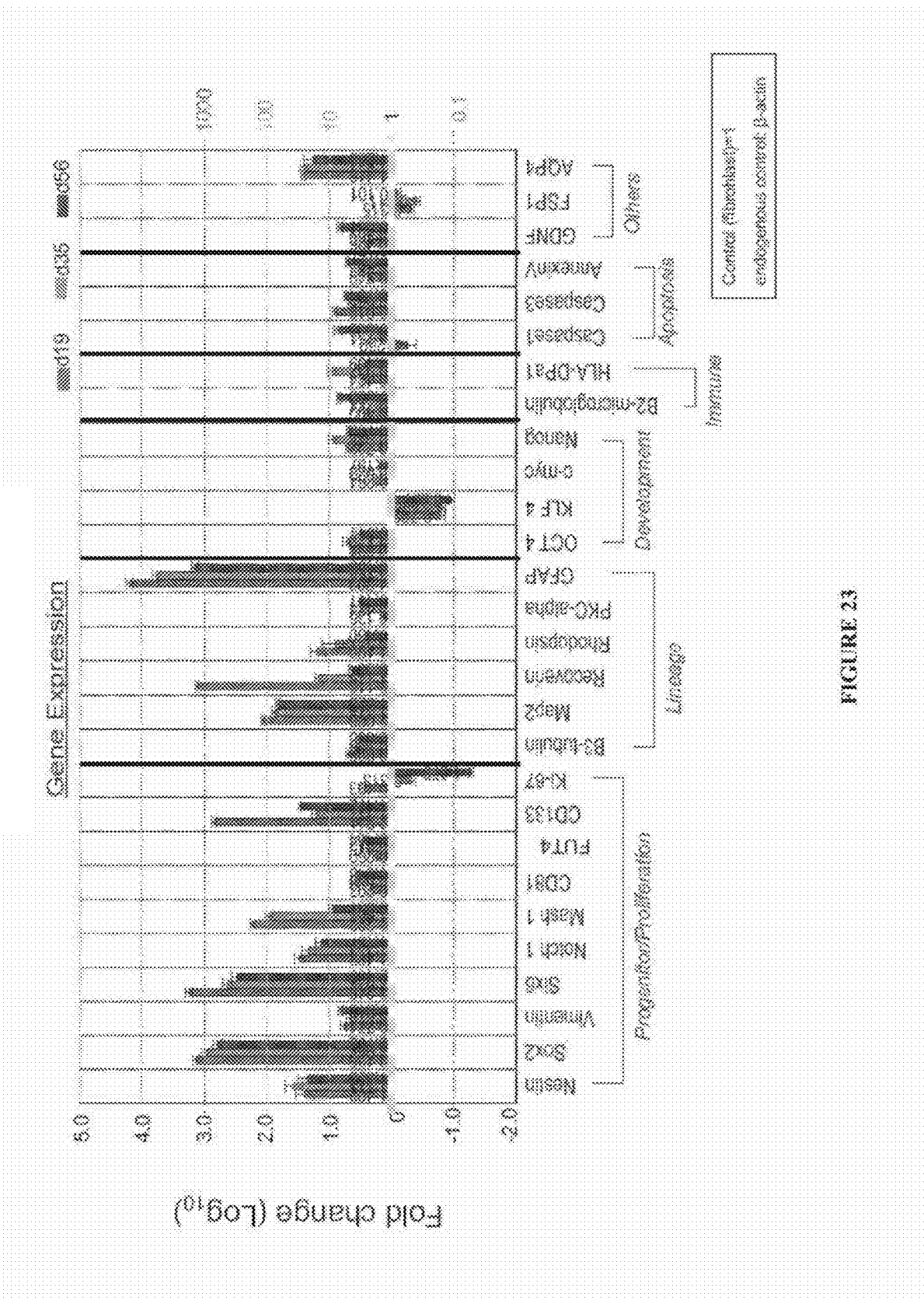
FIG. 23 shows marker expression at RNA level, as detected by qPCR ("real time" PCR) at time points in culture.
Figure 24:
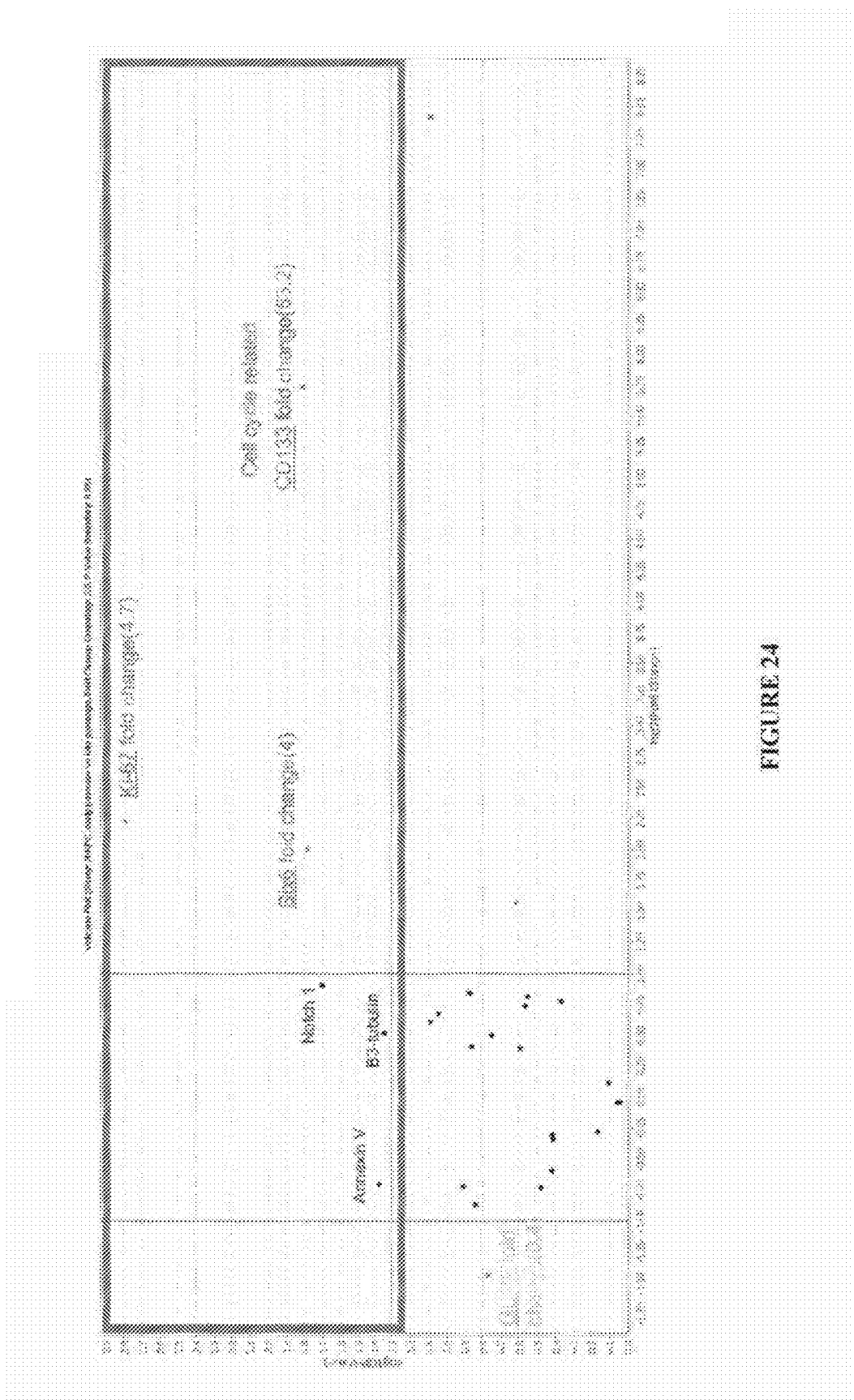
FIG. 24 depicts expression level changes of various markers (e.g., GDNF, annexin V, β3-tubulin, Notch1, Six6, Ki-67, and CD133 in early vs. late passage cells.

The expression levels of selected markers were tracked as a function of time in culture by real time qPCR. As shown in FIG. 23, highly expressed markers tend to ease off of peak expression levels with time. For example, Ki-67 tends to drop with time, consistent with progenitor status and lack of immortalization. MHC and GDNF expression show a modest increase over time in culture. Changes in the expression level of markers in early vs. late passage cells were tested, the results of which are shown in FIG. 24. Cell cycle genes and Six6 (a transcription factor critical to retinal development) are most strongly down-regulated in late passage cells. Conversely, the neuroprotective factor GDNF tends to be up-regulated at late passage, possibly as a result of cellular stress.

Figure 25:
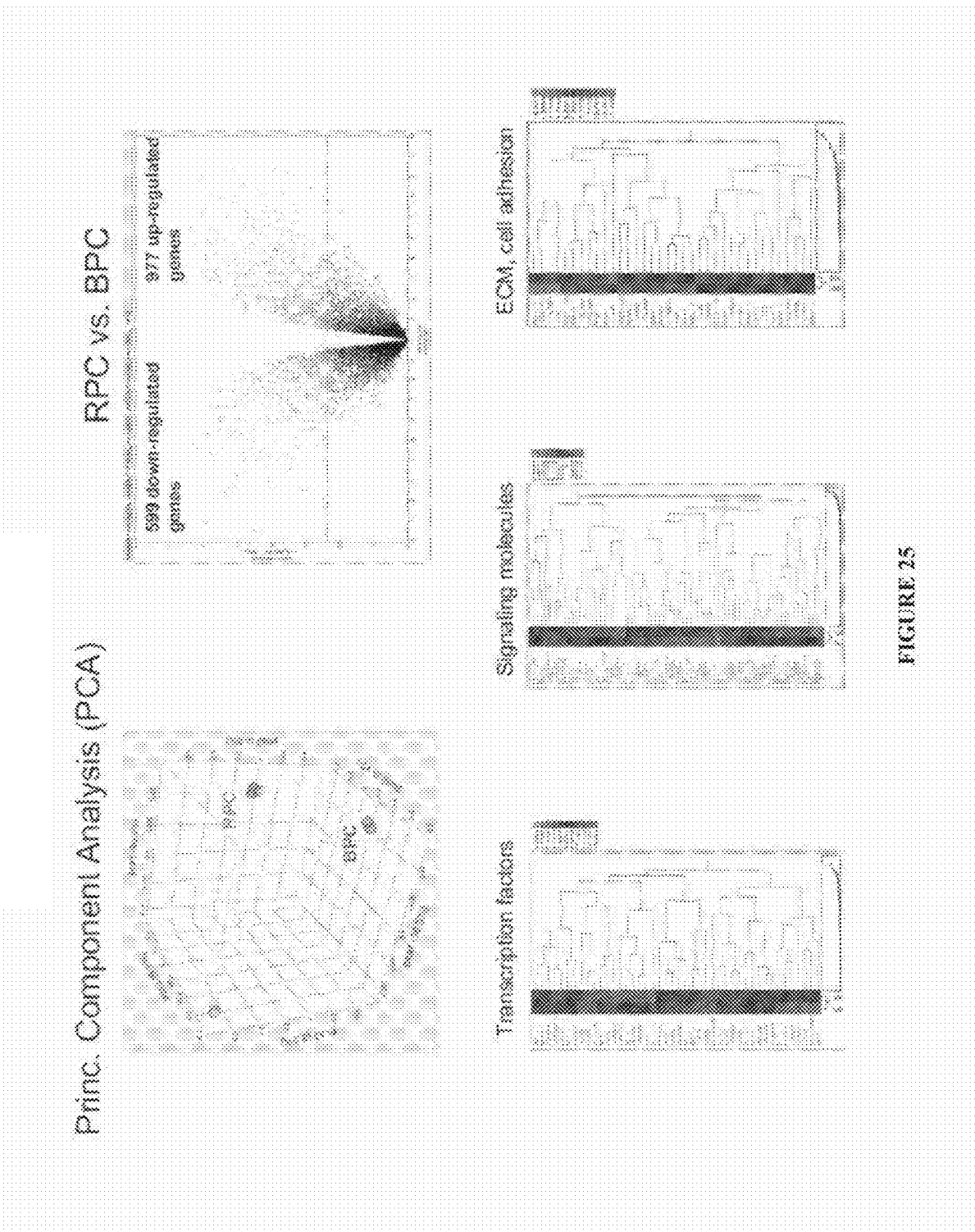
FIG. 25 represents a summary of microarray data that distinguishes hRPCs from neural stem cells (BPCs).

A summary of microarray data that distinguishes (human) RPCs from neural stem cells (BPCs) is shown in FIG. 25. Principal component analysis shows clear segregation of RPC data sets (3) from BPCs (3), demonstration that RPCs as a cell population type can be distinguished from analogous brain-derived cell types, such as BPCs, based upon their transcriptome. A Volcano plot shows the basis of this difference in the form of close to 1000 transcripts significantly up-regulated in RPCs compared to BPCs, as well as ~600 transcripts that are significantly down-regulated. The comparison is further delineated using dendrograms for transcripts according to specific gene categories and specific genes are identified. For instance, the transcription factor BHLHE41 (basic helix-loop-helix family, member e41) is highly expressed by RPCs with very low expression by BPCs. This gene encodes a transcription factor that belongs to the Hairy/Enhancer of Split subfamily of basic helix-loop-helix factors. The encoded protein functions as a transcriptional repressor. Other transcription factors preferentially expressed by RPCs over BPCs include HHEX, SOX3 and SOX13, HOXB2, LHX2, KLF10, TLE4, MYCBP, TFAP2A, FOSL1 and 2, FOXD1, NHLH1, GBX2, NEUROD, MET, etc. In terms of signaling molecules, numerous transcripts are shown to be expressed by RPCs at markedly higher levels than in BPCs/neural stem cells, including for WNT5A and B, KDR, LIF, CALB1, RGS4, CAV2, IL11, IL1R1, IL1RAP, IL4R, IL21R, CXCL6 and 12, CXCR7, DKK1, HBEGF, SMAD7, BMP2, etc. Similarly, the ECM matrix genes fibronectin, LUM, ALCAM, TGFBI, ECM1, PARVA, as well as the collagens: 4A1, 4A2, 5A1, 5A2, 7A1, 9A2, 13A1, 18A1, and a variety of other ECM genes are also preferentially expressed by RPCs.

Figure 26:
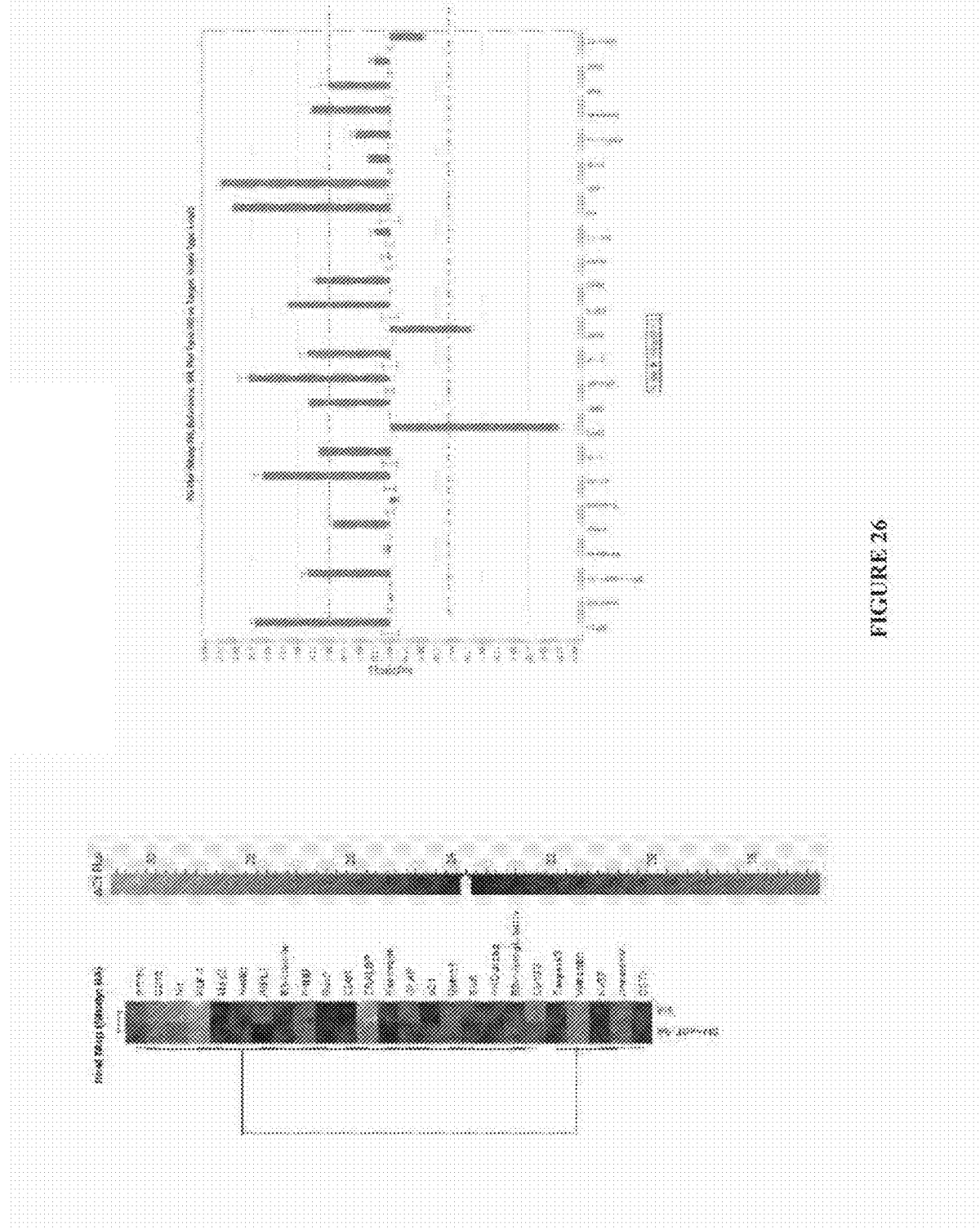
FIG. 26 shows marker expression after differentiation with retinoic acid (RA).

Experiments testing marker expression after differentiation with retinoic acid (RA) in hRPCs were conducted; the results are shown in FIG. 26. The genetic profile of hRPCs grown in standard proliferation medium (SM) were compared to RA-based differentiation conditions (SM without GFs+RA). The proliferation marker Ki-67 is decreased, as is vimentin, while the tumor suppressor gene p21 goes up, along with lineage markers like AIPL-I, MAP2, NRL, CRALBP, GFAP and recoverin. The increase in both glial and neuronal markers is consistent with multipotency of the cultured RPC population. Other markers that can be used to practice the invention to identify hRPC cells are described in U.S. Pat. No. 7,419,825.

Figure 27:
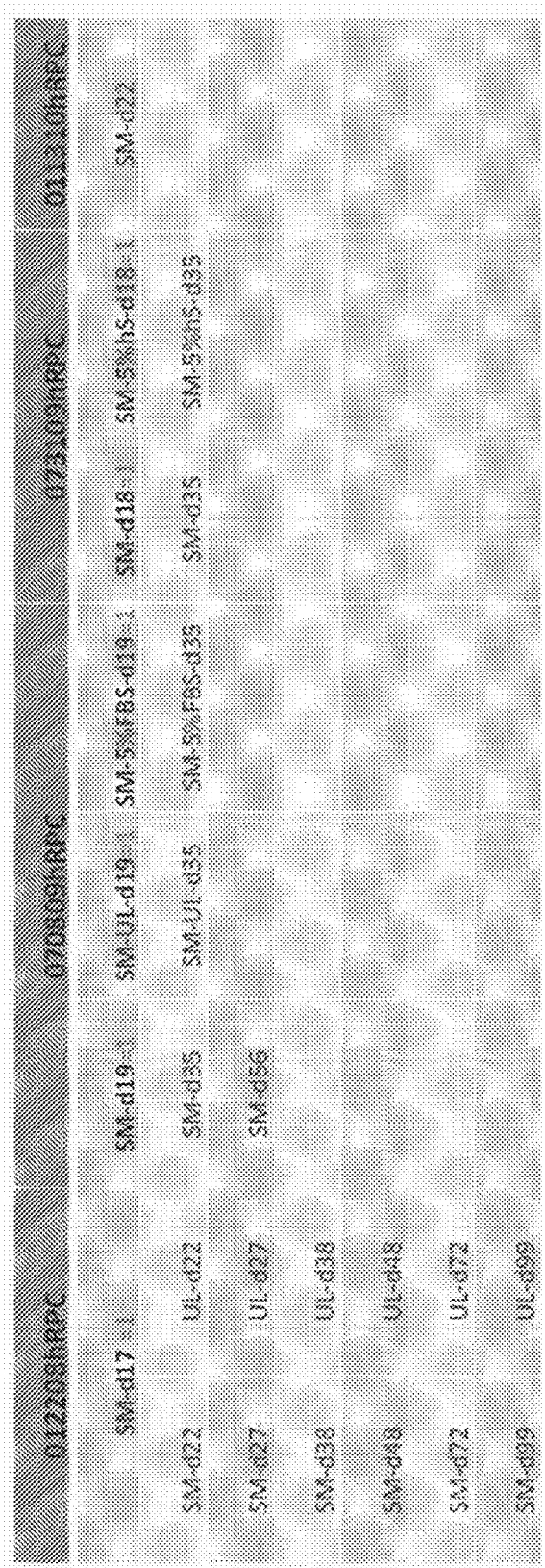
FIG. 27 is a summary table of culture conditions of hRPCs grown from different tissue donations.

In addition, gene expression of hRPCs grown under lowOx conditions in comparison to atmospheric Ox were tested (FIG. 27). The data indicates that there are detectable changes in gene expression, with upregulation of the surface markers CD9 and CD73, but mostly down-regulation of genes was observed, including the tumor suppressor gene p21 as well as the lineage markers CRALBP, GFAP, MAP2, NRL, and recoverin. These changes are most consistent with decreased expression of non-essential genes as the cells proliferate in a sustained manner under these permissive conditions. GDNF is also down regulated, perhaps because of decreased need for autocrine neuroprotection.

Figure 28:
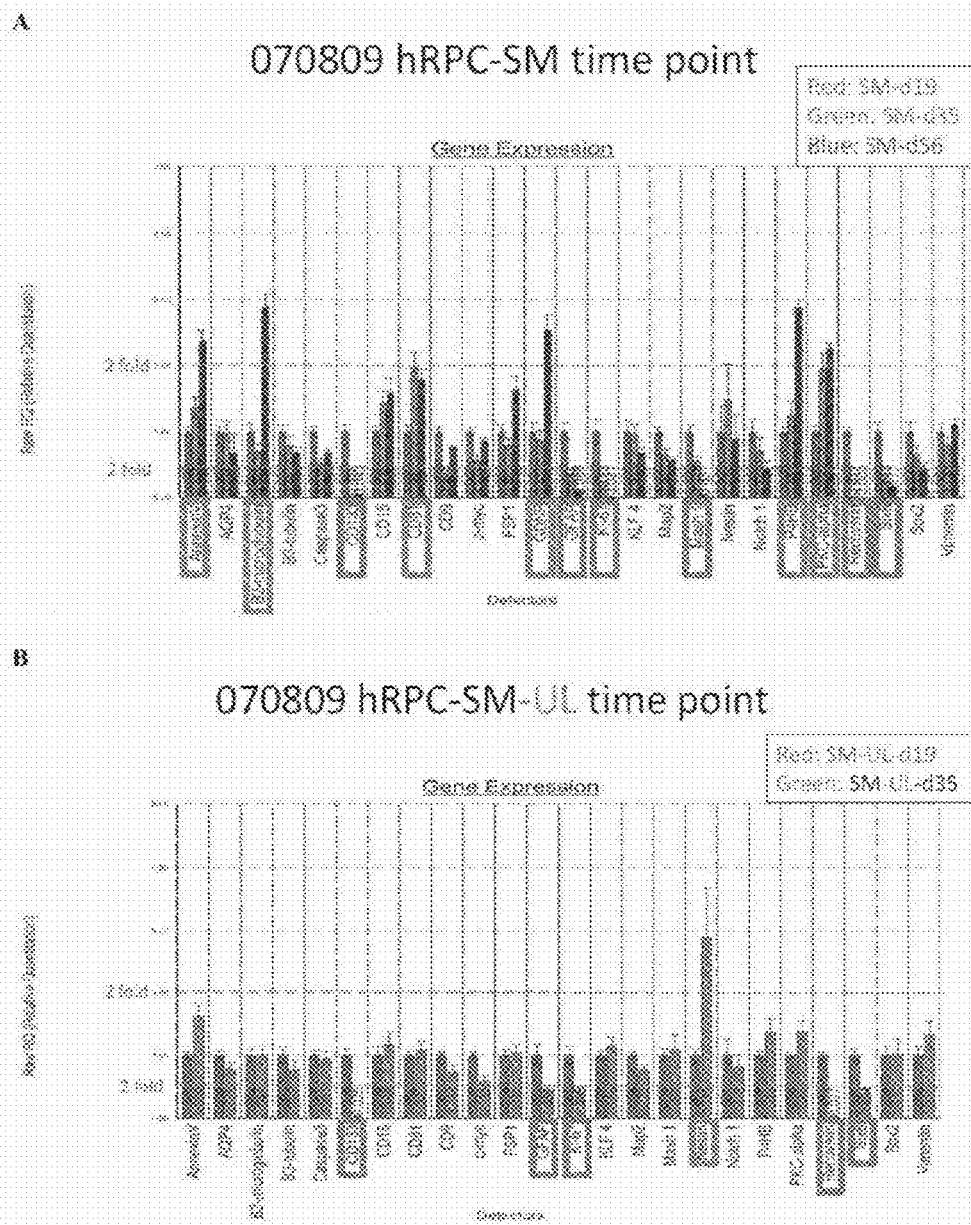
FIG. 28 illustrates differences in gene expression between hRPCs derived from different donors and cultured in a variety of cell culture media conditions and time points were tested.
Figure 29:
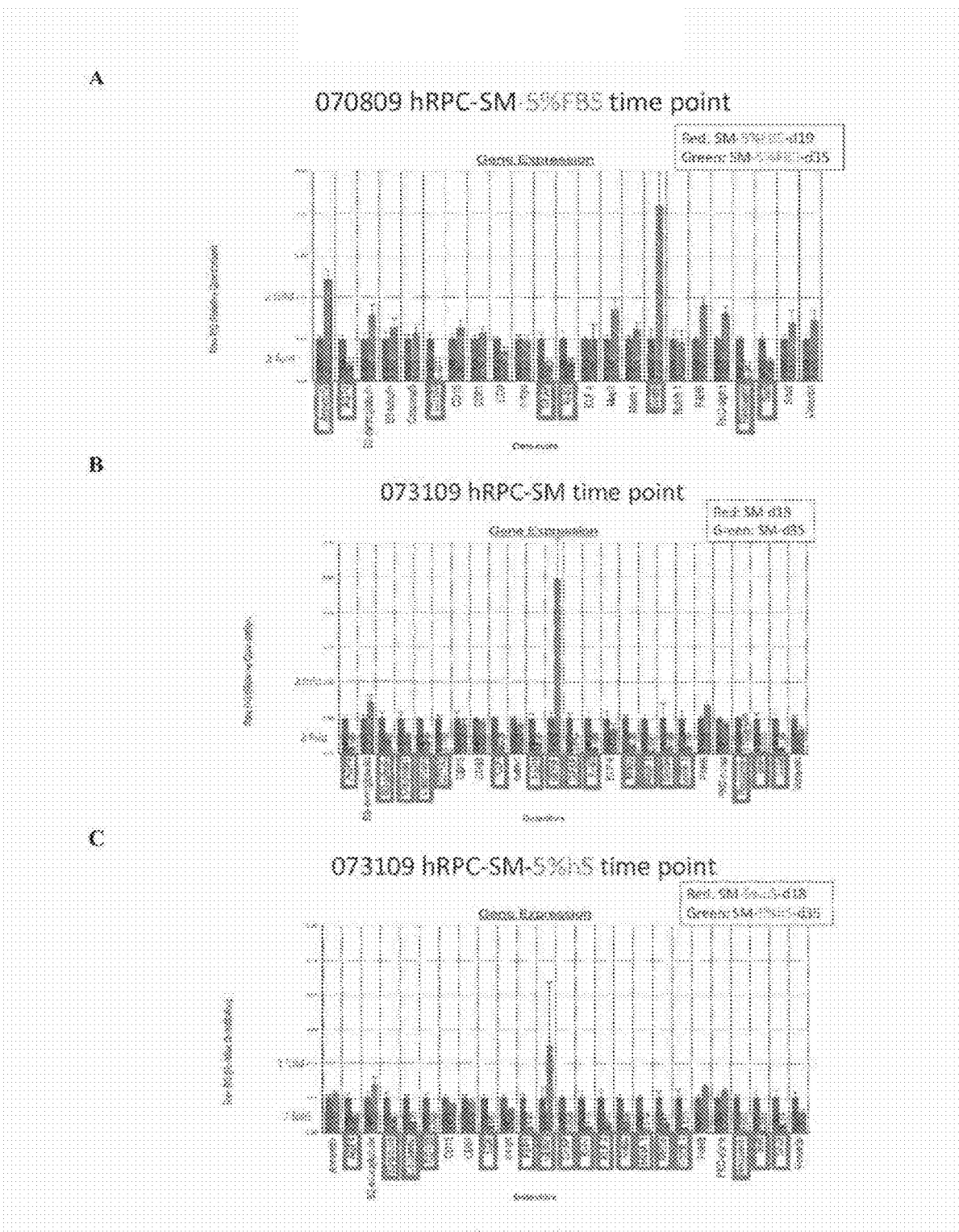
FIG. 29 illustrates differences in gene expression between hRPCs derived from different donors and cultured in a variety of cell culture media conditions and time points were tested.
Figure 30:
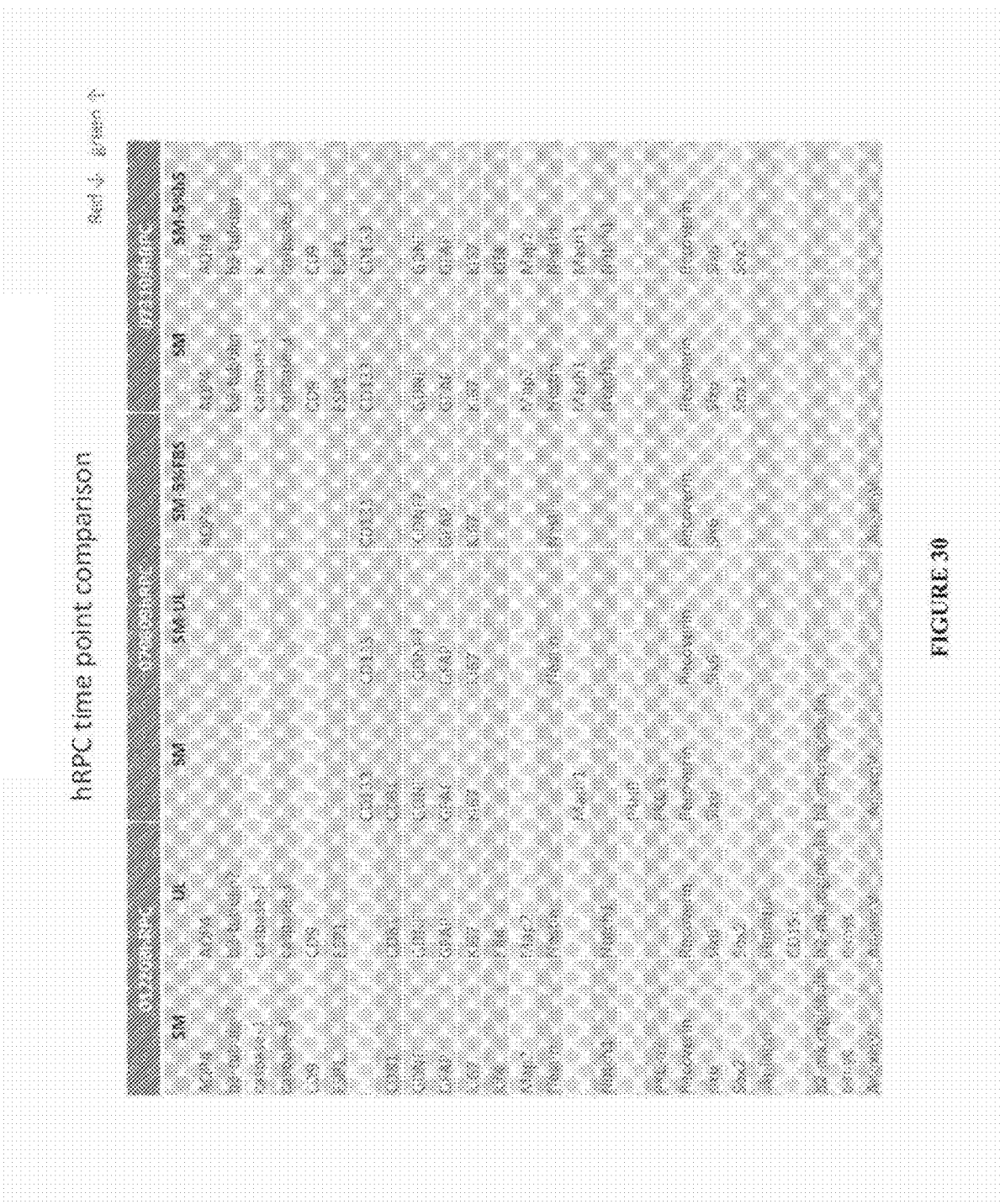
FIG. 30 is a table summary of time point comparison experiment results showing FIGS. 28 and 29. Genes showing strongly consistent trends across treatment conditions are highlighted in yellow.

Differences in gene expression between hRPCs derived from different donors and cultured in a variety of cell culture media conditions and time points were tested and the results are shown in FIGS. 28-30. FIG. 28A shows the results of an experiment that detected gene expression by qPCR at SM conditions at different time points; FIG. 28B illustrates gene expression by qPCR at SM-UL (initial UL, then SM) conditions at different time points; FIG. 29A illustrates gene expression by qPCR at SM-FBS (initial SM+FBS, then SM) conditions at different time points. FIG. 29B illustrates gene expression by qPCR with SM alone, 2 different time points. Most of the tested markers showed decreased expression over time in culture, while some remain roughly level. Notably, of the tested markers, only GDNF expression increased over time in culture. FIG. 29C illustrates gene expression by qPCR with SM (after initial SM+FBS) same 2 time points. As shown in FIG. 29B, only GDNF is elevated. FIG. 30 represents a summary of these time point comparisons.

qPCR was used to further characterize hRPCs in relation to growth factor pathways and was directed at relative expression of secreted factors. Specific panels included angiogenesis and WNT signaling pathways. Cells used in these experiments were derived from hRPCs of low passage that were grown under normoxic (20% oxygen) and hypoxic (3% oxygen) conditions; from a working cell bank, which includes hRPCs of higher passage that were grown under hypoxic conditions; or from human fetal retinal tissue at Day 0 (the day of donation), which represents the baseline origin of hRPCs. Human fetal RPE (hRPE) cells and human fetal fibroblasts (hFB) were used for comparison.

Figure 31:
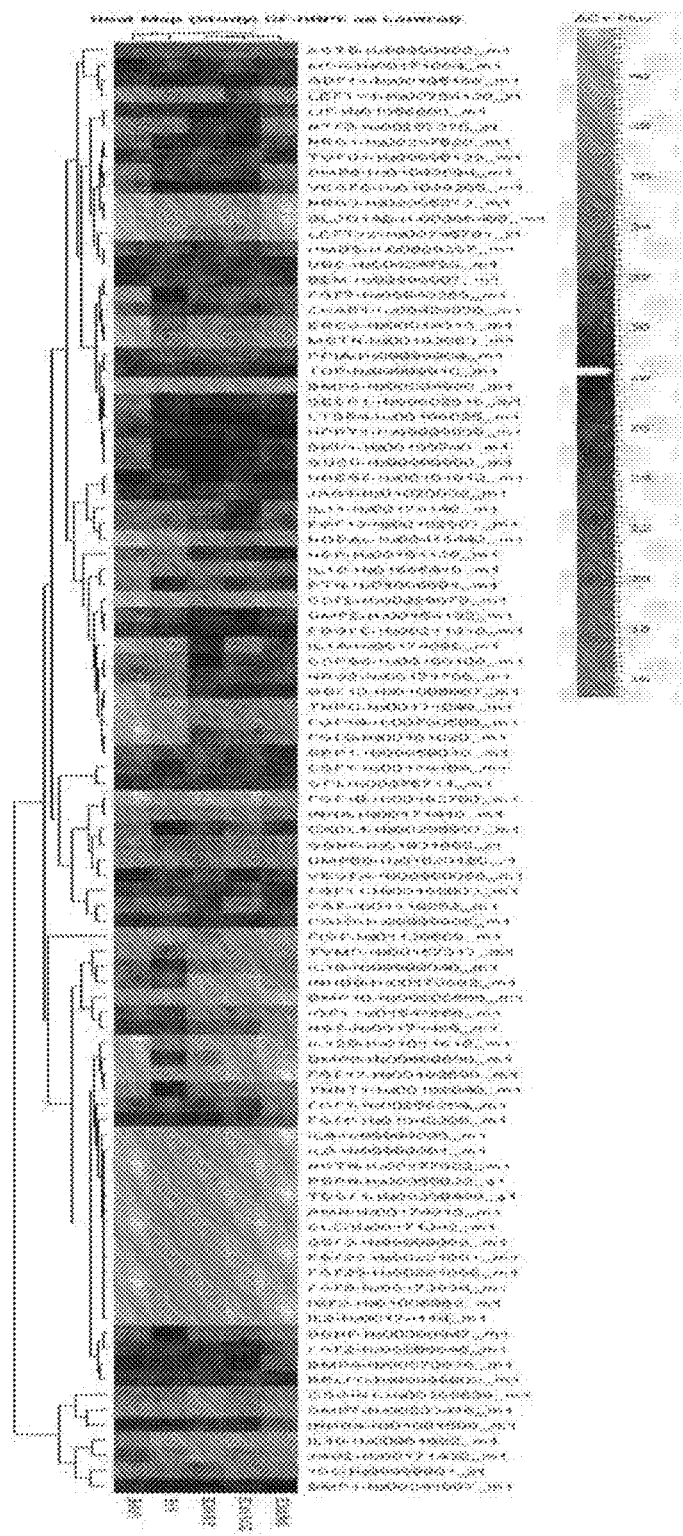
FIG. 31 depicts a heat map analysis of qPCR data obtained from hRPCs.

FIG. 31 is a heat map analysis of qPCR data for growth factor pathway study. Each vertical column is a different cell type or treatment condition. Human fetal RPE and fibroblast cells were used as comparators (first 2 columns), the 3 columns to the right are hRPCs. One cytokine with notably high expression in 2 of 3 hRPC banks, plus intermediate in the other, yet not expressed by RPE or FB is SPP1 (osteopontin, OPN), which is currently a primary candidate for trophic mechanism of action factor. Another candidate is PTN (pleiotrophin), which is also highly expressed, although this factor appears to be less specific than SPP1 (OPN). Other potential candidates from this data in terms of expression level are MDK (midkine), TGFB1 (TGFβ1), JAG1, VEGFA (VEGF A), PGK1 (phosphoglycerate kinase 1) and cases can be made for others to varying extents such as GDF11, DKK1, PPIA (peptidylprolyl isomerase A), and LIF, etc., depending on criteria used. Also, B2M (β2-microglobulin, a component of MHC class I) is not a cytokine per se, but is strongly expressed by hRPCs and a component of MHC class I.

When specificity is emphasized, the dendrogram clustering shows that those listed from HBEGF (heparin-binding EGF-like growth factor, HB-EGF), JAG1, down to SPP1 (OPN) all show a general specificity for hRPCs over fetal hRPE and fetal hFBs, and therefore could contribute to a heterogeneous "cocktail" effect. This includes PTN, as well as low levels of IL1B (interleukin 1β). It is also possible that the 20% MCB has the maximal trophic efficacy in which case the factors listed from MDK down to LEFTY2 would be of interest. UBC (ubiquitin C) was also detected. A number of these genes are known to play a role in retinal development, including GDF11, lefty, nodal, DKK1, LIF, etc. Many are known to be neurotrophic, including SPP1, NTF3, HB-EGF or related to neural development such as midkine, neuregulins (NRG1, 3), the JAGs, etc.

Figure 32:
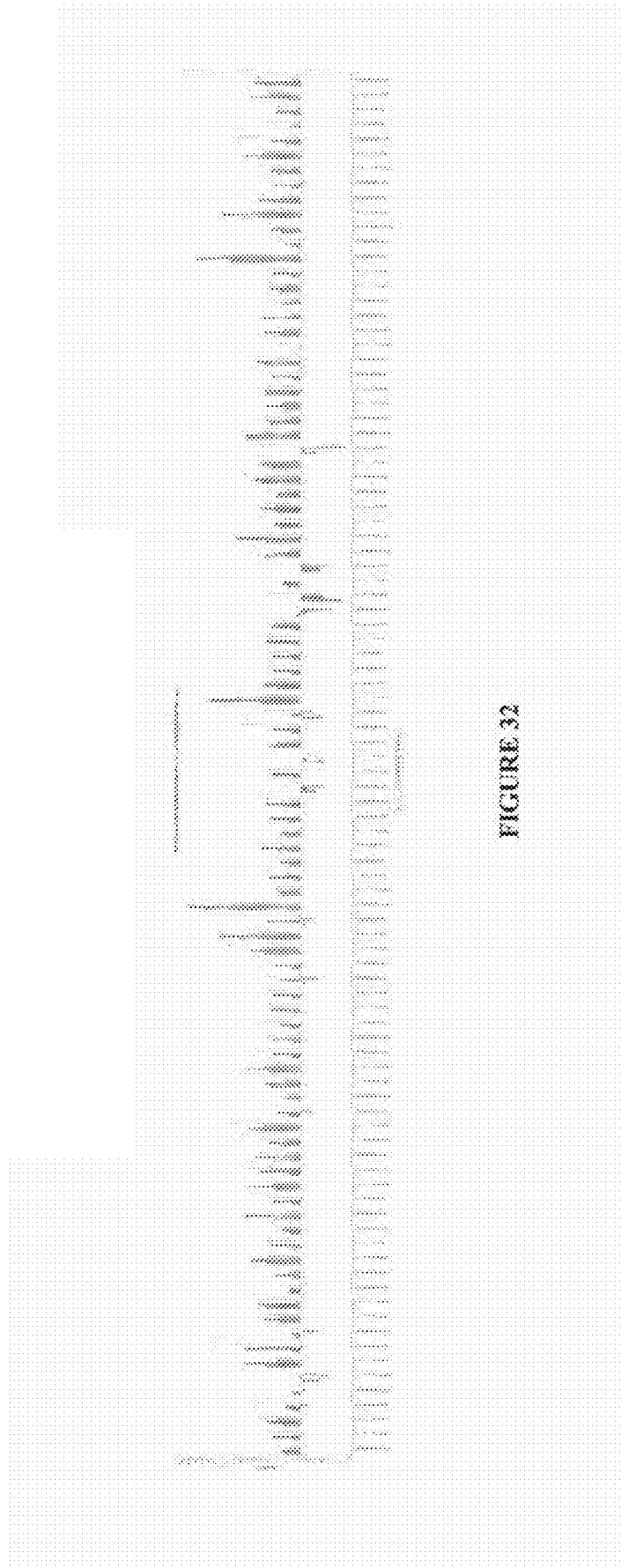
FIG. 32 represents a histogram of qPCR data from hRPCs.

Another view of qPCR data from the growth factor pathway study is provided in FIG. 32, seen here as a histogram. Human fetal RPE cells were used for comparison. Viewed quantitatively in terms of expression level, secreted genes that showed particularly high expression by hRPCs included FGF9, GDF10, IL-1A (interleukin 1 alpha), PTN, and SPP1 (osteopontin, OPN). All of these genes were found to group in what appears to be a relatively hRPC-specific cluster of the heat map, above, and so are considered candidates for mediating a trophic mechanism. Other genes showing lower relative expression, but still elevated, include BMP2, FGF7,13,14, Lefty1,2, nodal, NTF3, thrombopoietin and potentially VEGF A,C. Genes that were preferentially downregulated by hRPCs relative to hRPE were JAG2, NGF, inhibin beta B (INHBB), and IL-10.

RPC are active before and during the period of retinal vasculogenesis and as such can be expected to play a role in angiogenesis, especially as they begin to differentiate. Factors and receptors involved in molecular pathways regulating angiogenesis could also be potentially neurotrophic in the setting of the degenerating retina. Also, activation or inhibition of these pathways could be important in a range of retinal conditions, including AMD, either beneficially or as an undesired side effect.

Figure 33:
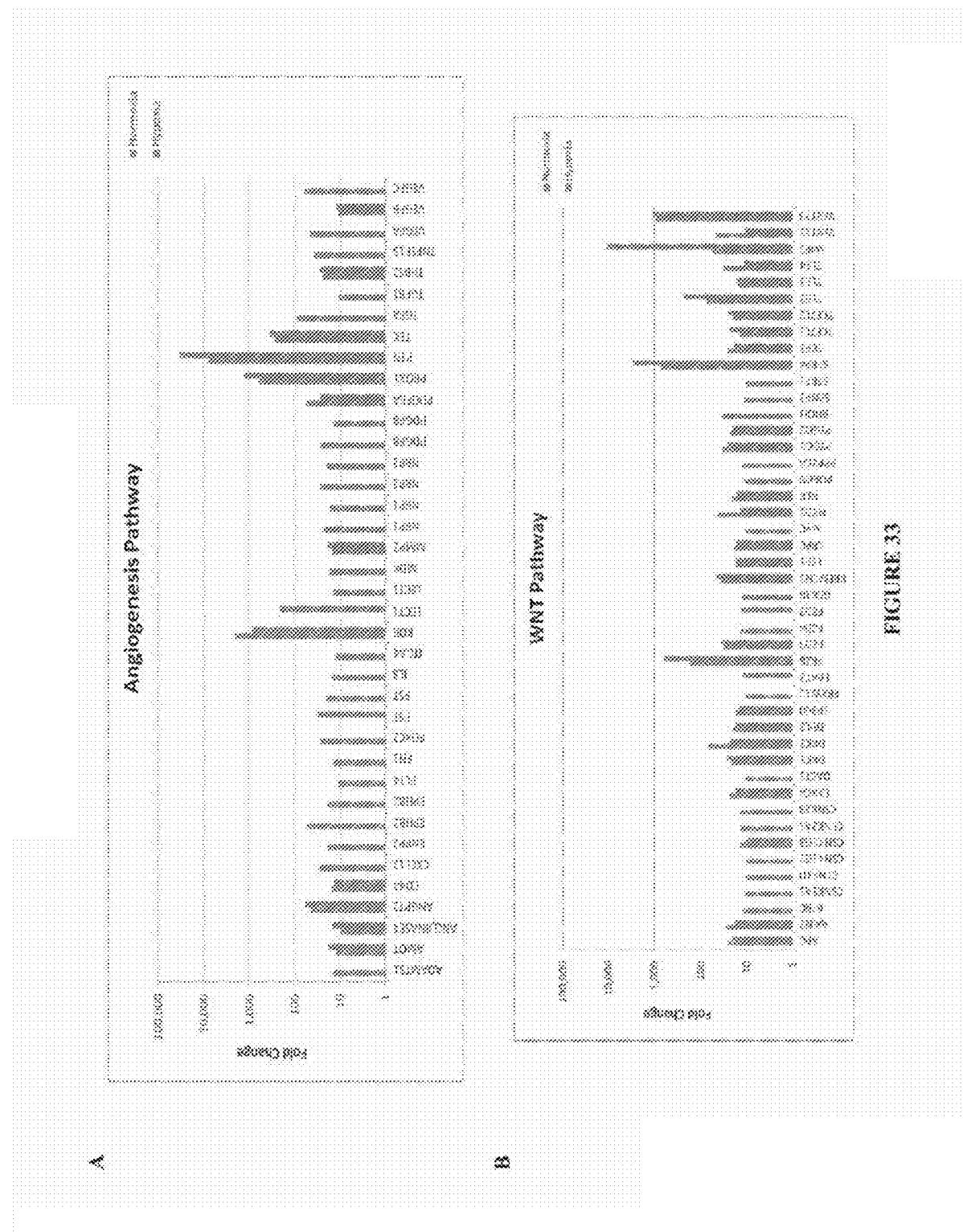
FIG. 33A depicts qPCR expression levels of angiogenesis pathway angiogenesis-related genes in hRPCs.
FIG. 33B depicts qPCR expression levels of WNT-pathway related genes in hRPCs.

All genes shown in FIG. 33A were upregulated compared to RPE by at least 10 fold. Genes upregulated more than 100 fold included the VEGF receptor KDR, chondromodulin/LECT1 (hypoxic condition only), the transcription factor PROX1, and the receptor TEK (TIE2). The factor with the highest expression relative to RPE was pleiotrophin (PTN) at over 10,000 fold for hypoxic hRPCs and approaching that for normoxic cells.

Clear evidence of increased expression of angiogenesis-related genes and additional confirmation of high levels of PTN expression, one of the top trophic factor candidate genes, were detected. Elevated expression of the surface markers KDR and TEK, both identified in previous screens, were also confirmed here. The VEGF receptor KDR was consistently found to be elevated in RPCs versus other cell types. The microarray data also showed KDR expression in hRPC>hBPC (brain progenitors) of 80 fold, and in porcine RPCs>BPCs of 106 fold. KDR is therefore a surface marker potentially useful for identification and enrichment of RPCs, is a way to distinguish RPCs from BPCs (neural stem cells) and is of likely importance to the function of RPCs.

WNT pathways are believed to be important to neural development, including the differentiation of neurons and glia, throughout the CNS and including the retina. Genomic studies have previously identified considerable evidence of WNT pathway activity in hRPCs, based on gene expression levels of WNT-related genes, including WNTs, "frizzled" receptors, and WIF (WNT inhibitory factor). In FIG. 33B, all genes shown were upregulated compared to RPE by at least 10 fold. The genes upregulated by more than 100 fold included FRZB, SFRP4 (normoxic), TLE2 (hypoxic only), and WNT7B (normoxic). SFRP4 (hypoxic) and WNT7B (hypoxic) were both upregulated at levels greater than 1000. Just reaching 10,000 fold change was WIF1 (hypoxic only) showed ~10,000 fold change in expression.

In summary, clear evidence of WNT pathway gene expression, including prominent expression of WNT inhibitory genes, was observed by microarray analysis. Prior microarray data already showed that WIF1 is preferentially expressed by hRPC>hBPCs (brain) by 45 fold. Marked upregulation of SFRP4 and especially WIF1 (both of which can result from FRZB activation) appears to be characteristic of hRPCs grown under hypoxic conditions. This relates to the ability of hRPCs to better maintain an immature state and proliferate for extended periods under hypoxic conditions, thereby hugely increasing the yield of these difficult to grow cells. The qPCR data presented above intersect meaningfully with prior results obtained from microarray. These showed that LIF is preferentially expressed in hRPC>hBPC (brain) by 65 fold, HB-EGF by 30 fold, DKK1 (dickkopf 1) by 23 fold, osteopontin (SPP1, OPN) by 6 fold, TGF beta 1 and BMP2 by 5 fold, and JAG1 by 3 fold. Each of these genes contributes to the composition/identity of hRPCs vis-a-vis the analogous brain stem/progenitor cells (neural stem cells"), as does KDR to an even greater extent (80 fold) and also WIF (45 fold).

Principle component analysis (PCA) data from the microarray data shows the ability to distinguish cellular populations (therapeutic, non-therapeutic/control) based on global gene expression patterns. This also pertains to characterization of hRPCs by showing how closely related the samples are and the extent to which age (time in culture) and culture conditions (normoxic versus hypoxic) influence expression patterns.

Three pairs of fetal eyes (biological replicates) were obtained on the same day and provided RNA at Day 0 (retinal tissue) and were also used to grow RPCs (normoxic and hypoxic), as well as scleral fibroblasts. RNA was later extracted from the cultured cell populations and all sent for simultaneous microarray analysis.

Figure 34:
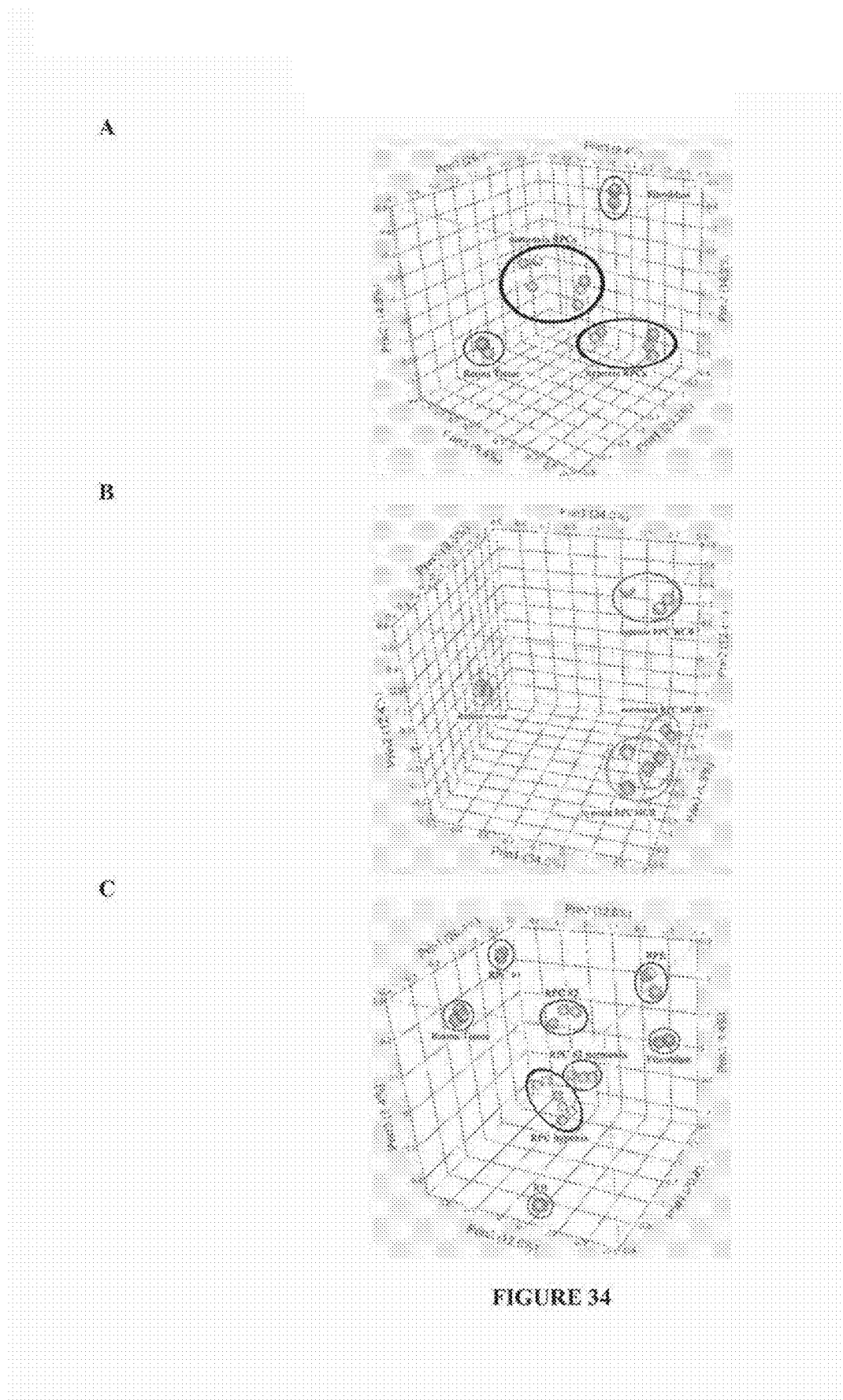
FIG. 34A is a graph summarizing the results of Principal Component Analysis (PCA) showing differences in qPCR gene expression levels between hRPCs vs. tissue and fibroblasts.
FIG. 34B is another PCA graph showing differences in qPCR gene expression between hRPCs vs. tissues obtained from fetal retina at day 0.
FIG. 34C is another PCA graph depicting three-dimensional visualization of the global similarities and differences between cell sample populations, lines are drawn to separate neural retina and neural retina-derived cells (left) from non-neural retinal cells (upper right).

FIG. 34A depicts the PCA data, which clearly shows that the culture RPCs differ in gene expression from the fetal retinal tissue from which they were derived, but also from scleral fibroblast. RPCs are closer to fetal retina than are the fibroblasts. In addition, normoxic and hypoxic RPC can be distinguished, although they appear to form a continuum, with younger cells at one end and older at the other. In FIG. 34B, hRPCs are clearly distinguished from PO retinal tissue of origin.

The influence of time in culture is evident in that the oldest cells (hypoxia WCB) can be distinguished from the other younger samples. The difference between normoxic and hypoxic conditions is not showing strong segregation.

A whole genome microarray study was undertaken to characterize the composition of hRPCs relative to other cells types, including how they differ from tissue of origin (fetal retina) and from grossly deranged and dangerous tumorigenic analogs, i.e., retinoblastoma (RB). Also, the study was undertaken to delineate the similarities and differences between normoxic and hypoxic hRPC cultures. Global gene expression of cell populations was compared on Affymetrix human gene chips.

Principle component analysis (PCA) provides immediate three-dimensional visualization of the global similarities and differences between cell sample populations. See FIG. 34C.

Figure 35:
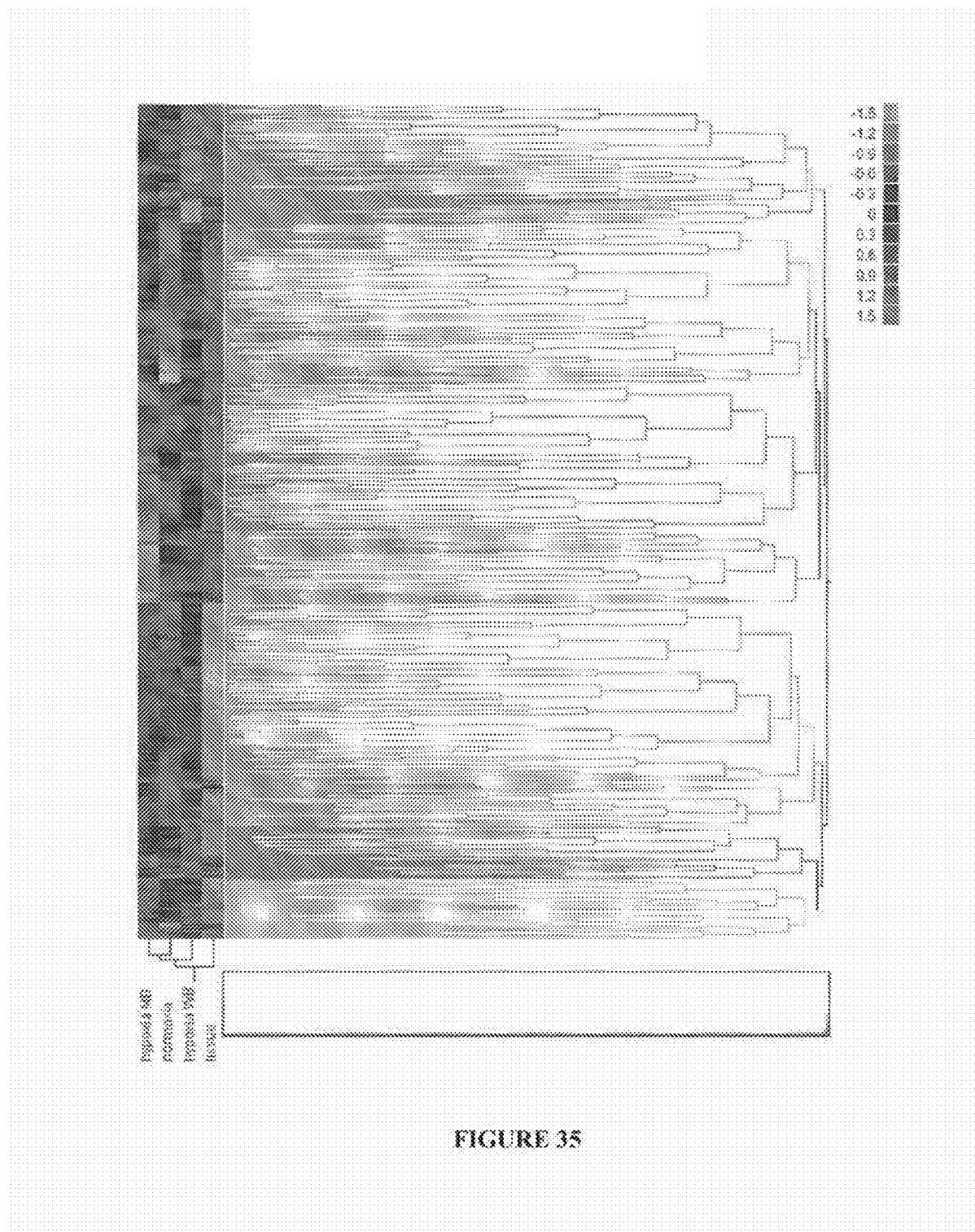
FIG. 35 shows cluster analysis of three hRPC populations (hypoxic MCB, normoxic MCB, and hypoxic WCB) versus fetal retinal tissue.
Figure 36:
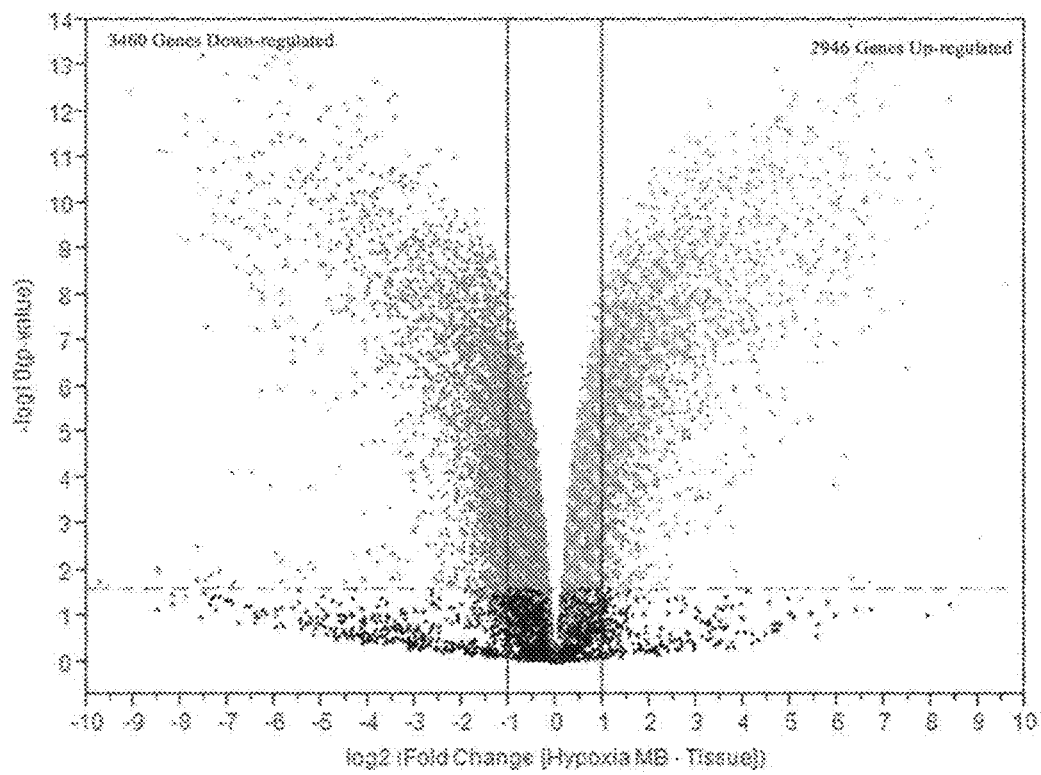
FIG. 36 is a Volcano plot comparing differences in gene expression in hypoxic MCB vs. tissue.

The grouping together of similar samples (all same color, all in triplicate) demonstrates the reliability of the data. Clear separation between fetal retinal tissue ("retina") was seen compared to the 4 different hRPC samples. The RPCs differed somewhat between each treatment condition, yet they segregate away from the other ocular cell types tested, i.e., fetal RPEs, fetal FBs, and RB. A line can be drawn to separate neural retina and neural retina-derived cells (left) from non-neural retinal cells (upper right). Finally, normoxic and hypoxic hRPCs are relatively close to each other and, although it may be possible to distinguish them to some extent, they appear to be closely related. The data shown are consistent with prior data regarding the relative similarities/differences of these different cell types. FIG. 35 shows cluster analysis of 3 hRPC populations (in order: hypoxic MCB, normoxic MCB, hypoxic WCB) versus fetal retinal tissue (triplicates used for each population). FIG. 35 is a Volcano plot showing the results of a comparison experiment between hypoxic MCB and tissue. The data show that hRPC populations are distinguishable from the original tissue populations. With few exceptions, genes that are seen as red in the tissue (right column) are green in the RPCs, and vice versa.

Figure 37:
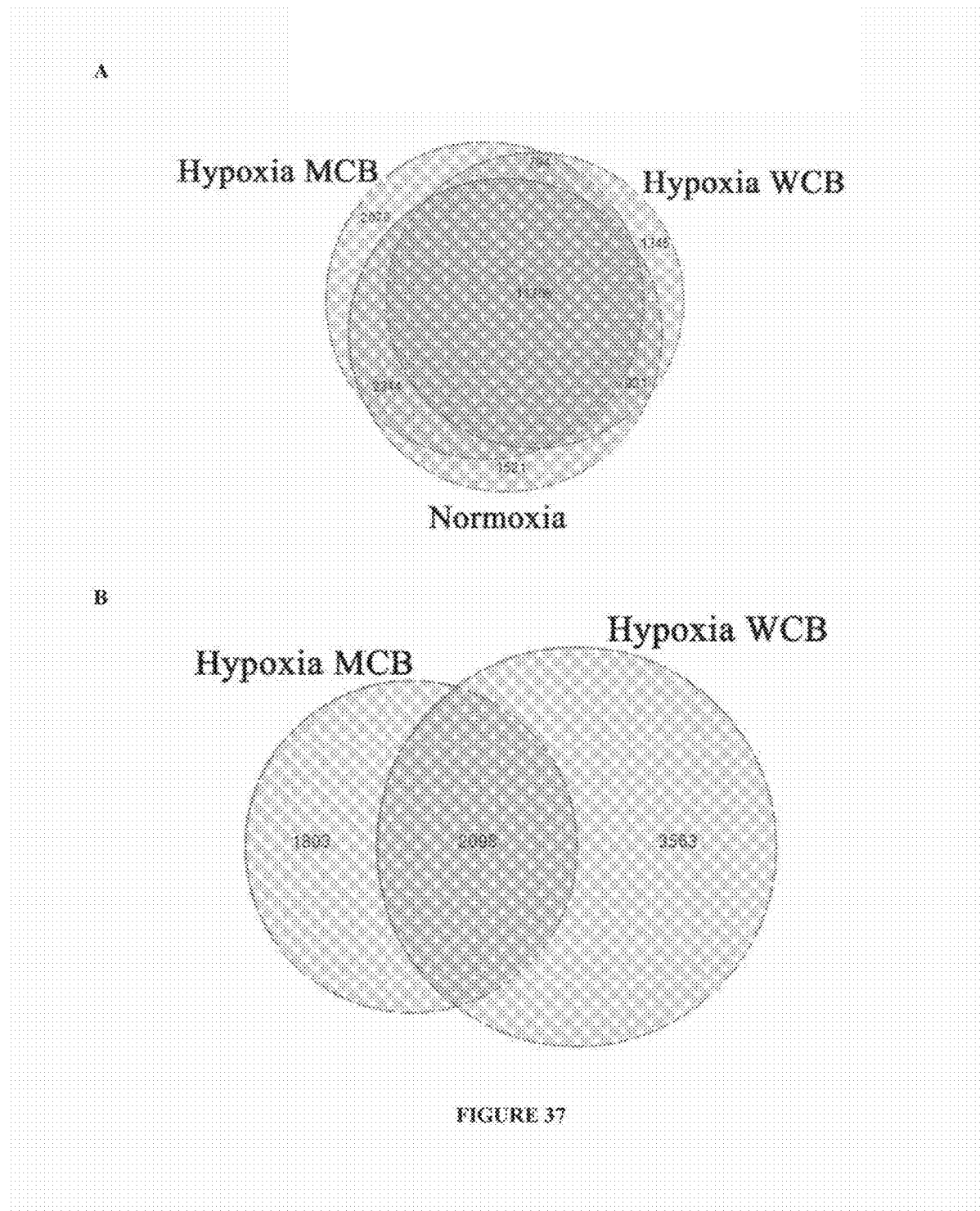
FIG. 37A is a Venn diagram showing the number of differentially expressed genes between hRPC groups as a function of the treatment conditions hypoxia MCB, hypoxia WCB and normoxia, with fetal retinal tissue used as comparator.
FIG. 37B is a Venn diagram showing the number of differentially expressed genes between hRPC groups normalized to tissue, as a function of passage number and treatment conditions hypoxia MCB and hypoxia WCB.

FIG. 37A shows the number of genes expressed differently between hRPC groups as a function of treatment conditions (fetal retinal tissue used as comparator). The majority of differences are accounted for by changes versus tissue (11,706, in center, gray), which are shared among RPC populations, while individual overlap and differences are seen around the periphery of the diagram. Each hRPC population expresses between approx 1300-2100 distinct genes. The number of genes expressed differently between hRPC groups was measured as a function of passage and treatment condition. See FIG. 37B. Cells grown under normoxic conditions were also compared. The hypoxic MCB differs less from the normoxic MCB (same passage number) than does the hypoxic WCB, which is at a later passage number. Thus, time in culture does have a demonstrable influence on gene expression in hRPCs, although it is far less than between cell types, or between hRPCs and tissue of origin.

Figure 39:
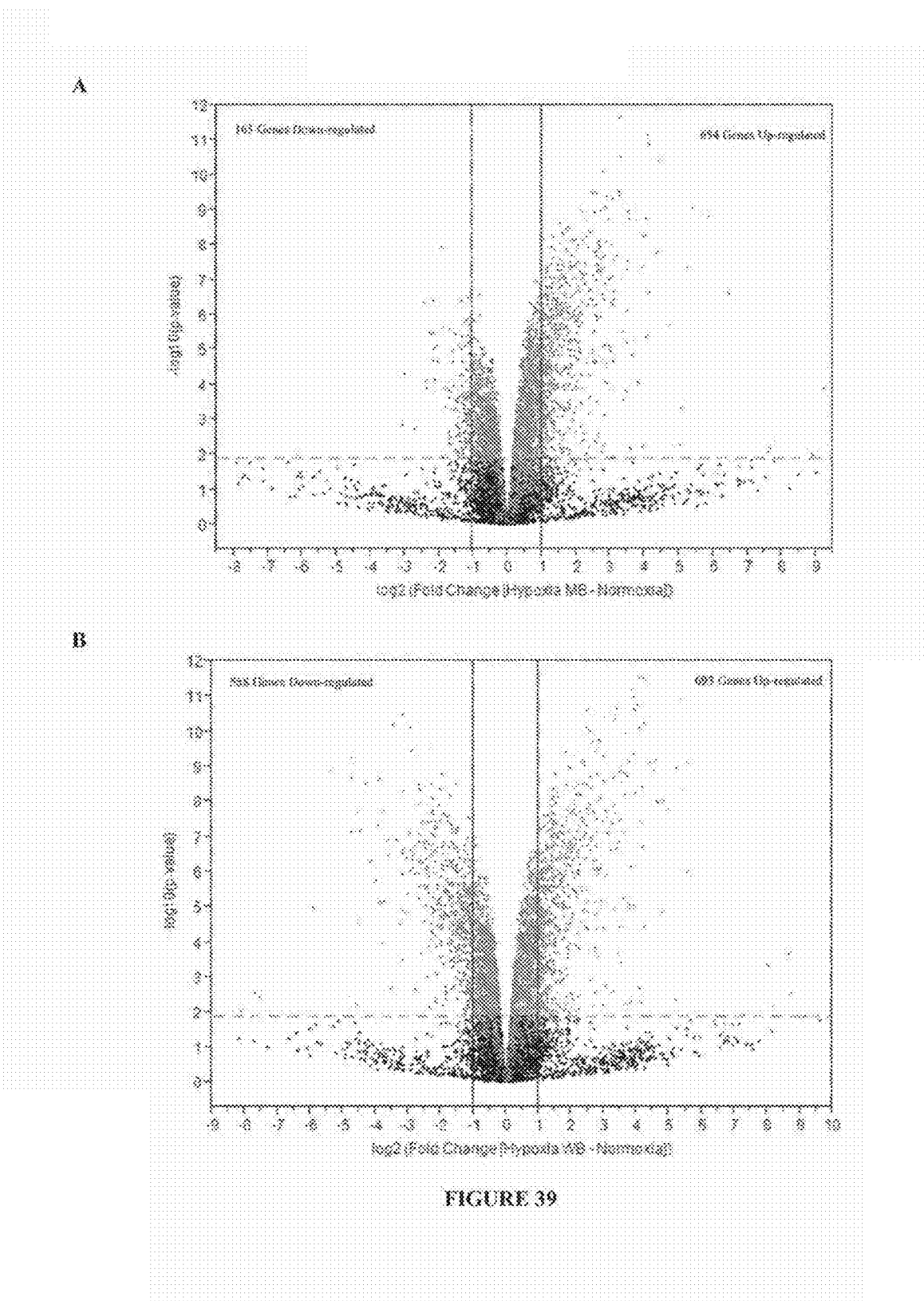
FIGS. 39A and 39B graphically illustrate, or plot, each gene as a data point, plotted relative to fold change (up or down, X axis) and statistical significance (function of p-value, Y axis), providing an overview of how many genes are changing, how much and in which direction (up vs. down), called Volcano plots comparing hypoxic hRPCs vs. normoxic hRPCs.
Figure 41:
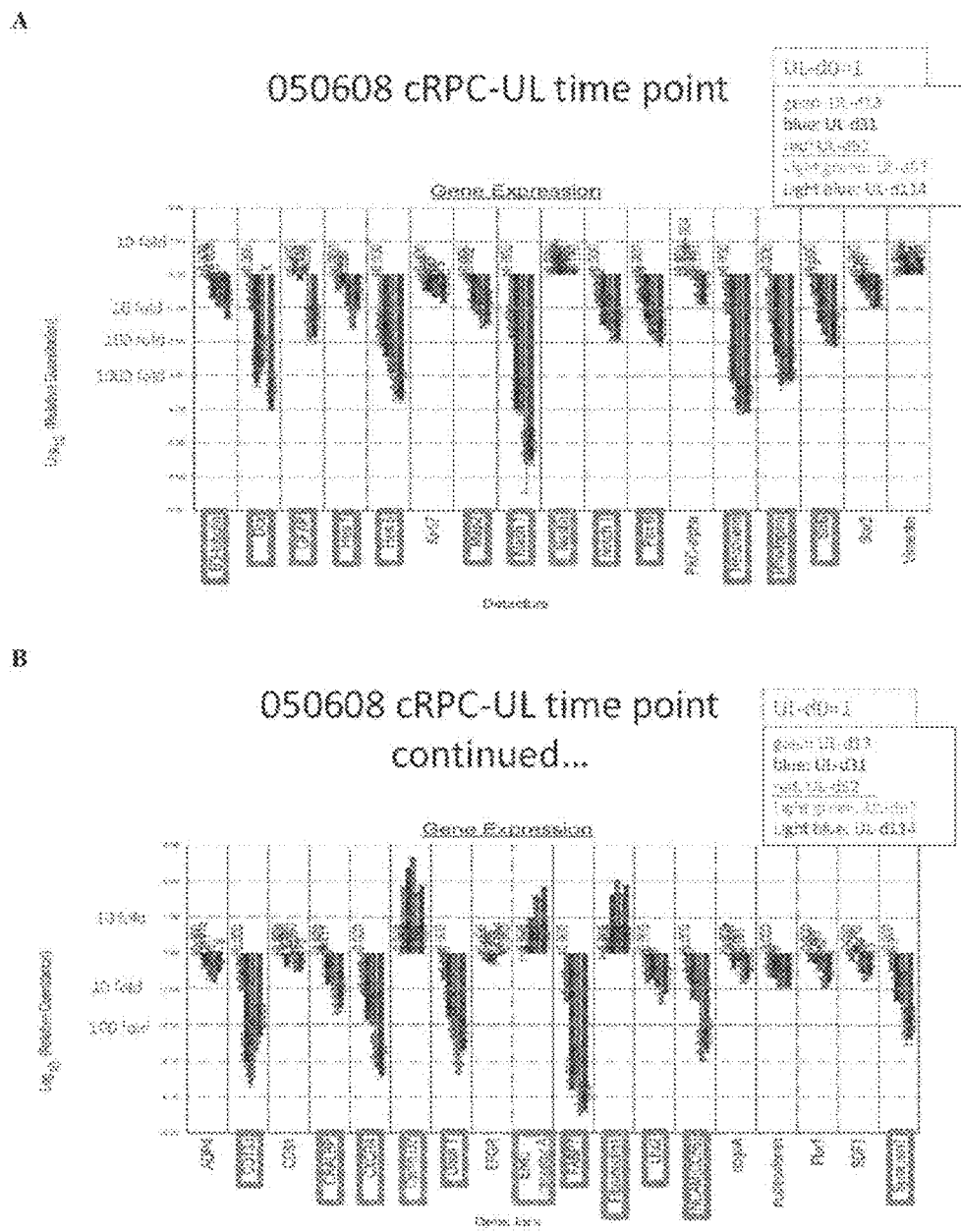
Figure 43:
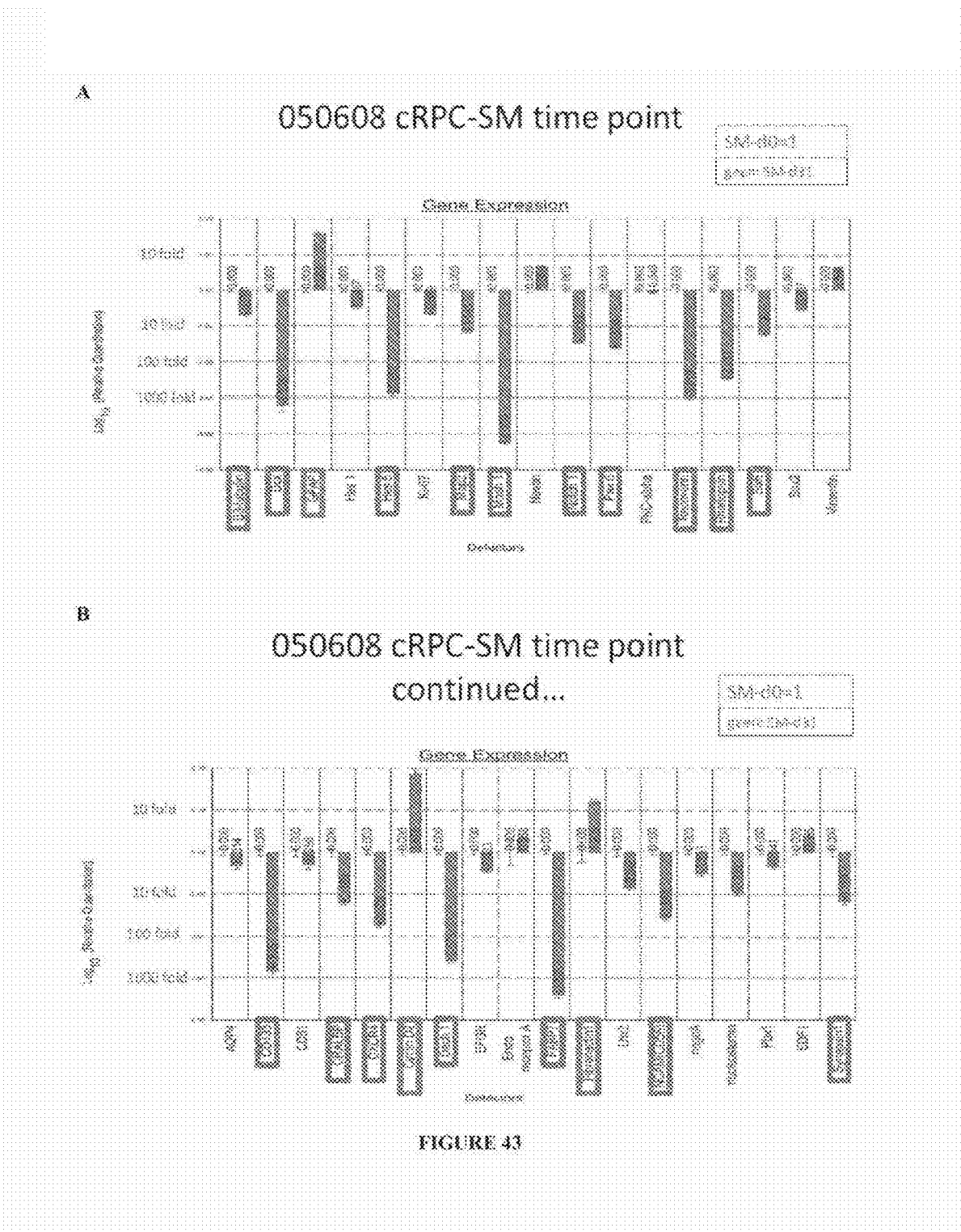
Figure 44:
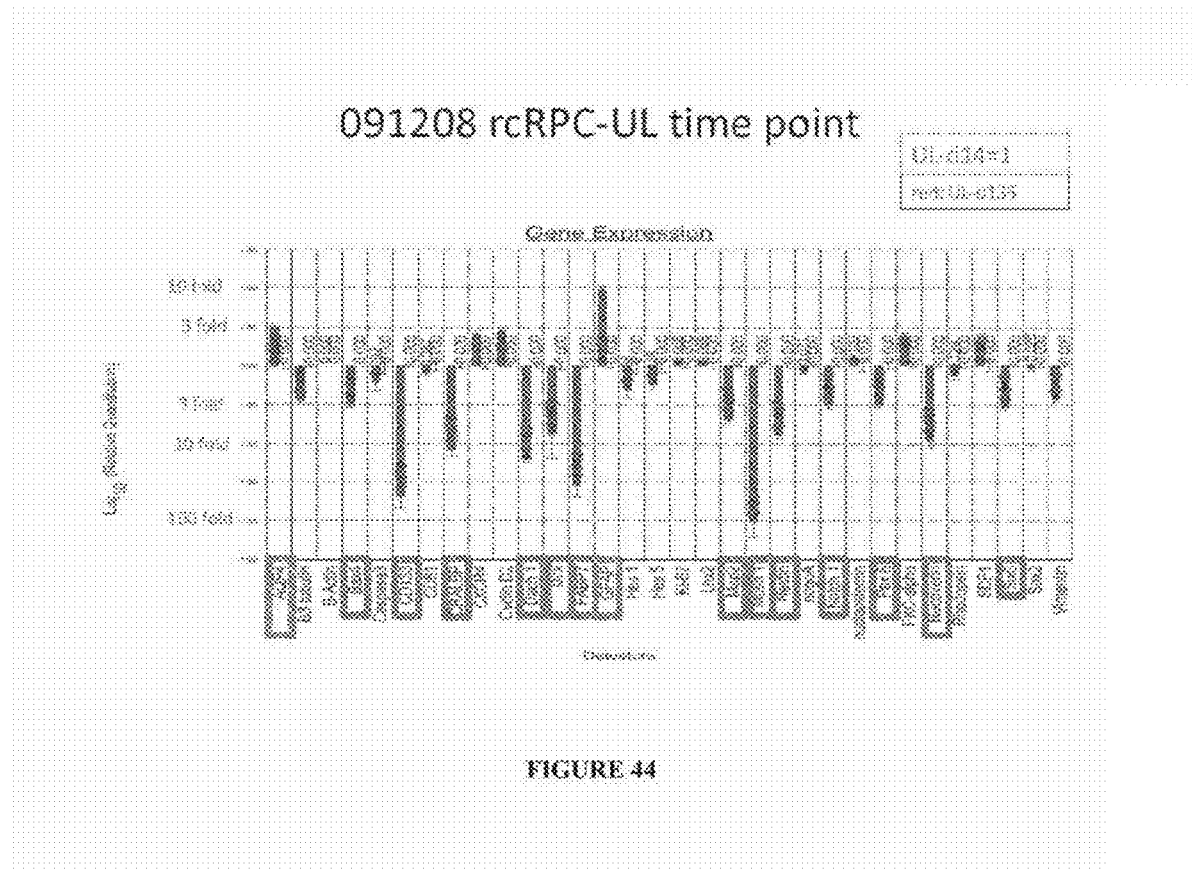

FIGS. 38A and 38B are Volcano plots showing different hRPCs versus tissue of origin, whereas Volcano plots in FIGS. 39A and 39B show hypoxic hRPCs versus normoxic. "Volcano" represents a style of plot showing each gene as a data point, plotted relative to fold change (up or down, X axis) and statistical significance (function of p-value, Y axis), providing an overview of how many genes are changing, how much and in which direction (up vs. down). The results indicate that a larger number of genes consistently change going from tissue to hRPC, than between hRPC conditions. In the former, more genes are downregulated than upregulated, presumably because more differentiated cell types present in the tissue are lost or overgrown in culture by more primitive, proliferative types. However, when comparing hypoxic to normoxic, more genes are upregulated in hypoxic conditions versus normoxic.

Specific genes and pathways were examined by microarray analysis as well. hRPCs, fetal retinal tissue (Day 0), and human fetal fibroblasts (normoxic) were compared. Adrenomedullin was upregulated in hRPCs vs. tissue. Pleiotrophin was found to be upregulated in hRPCs vs. tissue and hFB. Osteopontin was upregulated in hRPCs vs. hFB. Angiogenesis pathways were also found to be upregulated. Angiopoietins generally elevated in hRPCs vs. tissue and in hFB to lesser extent. ANGPTL4 is 30-60 fold upregulated in hRPCs vs. tissue and ~20 fold vs. hFB. BAI3 (inhibitor) is downregulated approximately 30-fold decreased in hRPCs vs tissue. Thrombospondin 1 is upregulated ~100-fold in hRPCs vs. tissue while thrombospondin 2 is upregulated ~40 fold in hRPCs vs. tissue. Matrix metallopeptidase 1 is ~200 fold upregulated in hRPC vs. tissue. The adhesion molecule NCAN (neurocan) is 16-21 fold downregulated in hRPC vs. tissue. The oncogenes/proliferation-associated genes MYC, MYCN, and NBL1 were also measured. MYC is upregulated 8-9 fold in hRPCs vs. tissue, consistent with proliferation of hRPCs. MYCN (v-myc related, neuroblastoma) is 25-40 fold downregulated in hRPCs vs tissue. NBL1 is downregulated 3-4 fold. A wide range of mitochondrial/metabolic genes including ATP synthase $H^+$ transporters and solute carrier family 25, were all generally upregulated 2-4 fold in hRPCs vs. tissue, however SLC25A27 (member 27) was ~20 fold downregulated. These data are consistent with the concept that cultured hRPCs are more metabolically active and more proliferative than cells in fetal retinal tissue of origin.

Growth factor expression was also examined CTGF (connective tissue growth factor) is strongly (>70 fold) upregulated in hRPCs vs. tissue. LIF (leukemia inhibitory factor) is similarly upregulated in hRPCs vs. tissue. BDNF and EGF are moderately (2-14 fold) upregulated in hRPCs vs. tissue. CNTF is downregulated ~25 fold in hRPCs vs. tissue. FGF9, which is a candidate trophic factor based on prior studies, is confirmed to be upregulated (4-6 fold) in hRPCs vs. hFB, and yet is 14-25 fold decreased vs. tissue. FGF5 is the family member most strongly upregulated in hRPCs compared to tissue (20-40 fold), yet expression is lower vs hFB. FGF14 is the most downregulated vs tissue, by 16-38 fold. HGF (hepatocyte growth factor) is 30 fold downregulated vs. hFB. Members of the insulin-like growth factor binding protein family, i.e., IGFBP3, -5, and -7, are generally upregulated in hRPCs vs. tissue. Members 3,5,7 are all strongly upregulated (15-110 fold). IGFBP3 and 5 are most strongly upregulated, specifically in the hypoxic cells (MCB, WCB). NTF3, a candidate factor, was not elevated over tissue, but was 8 fold elevated in normoxic hRPCs vs. hFB. NTRK2 (neurotrophic tyrosine kinase, receptor, type 2) was modestly upregulated in hypoxic hRPCs vs. tissue and strongly upregulated in all hRPCs vs. hFB (50-180 fold). PDGFC (platelet derived growth factor C), another candidate trophic factor, was upregulated 20 fold vs. tissue. VEGFA (VEGF A) was modestly upregulated by hypoxic hRPCs. DACH1 was modestly higher vs. hFB, but strongly downregulated in hRPCs vs. tissue. DLG2 (a synaptic marker) was also strongly downregulated in hRPCs vs. tissue. KLF family members showed downregulation of KLF4 vs. hFBs (3-4 fold), and upregulation of KLF5 vs. tissue (4-5 fold).

NeuroD1 (transcription factor associated with differentiation) was very strongly downregulated vs tissue (>300 fold), as was NeuroD4 and neurogenin 1 (and 2), as well as neuronatin (2-10 fold). NOG (noggin), a fate specification-associated factor is strongly expressed by hRPCs (10-21 fold) vs. tissue. OTX2 (ocular transcription factor) was very strongly downregulated in hRPCs vs. tissue. PAX6, SIX3, SIX6, RAX, RAX2 (ocular transcription factors) were only modestly downregulated in hRPCs vs. tissue. PAX6, at least, is known to be expressed by at least some RPCs.

DCX (post-mitotic neural blast marker) and RELN (reelin) a migratory neuroblast marker were strongly downregulated vs. tissue (the latter in hypoxic hRCs). SOX2, an important neurodevelopmental transcription factor, was unchanged vs tissue, but very strongly upregulated in hRPCs vs. hFB (>100 fold). Basoon, a mature retinal synaptic marker and recoverin (mature retinal cell marker) were strongly or very strongly downregulated vs tissue (20 fold and 50-450 fold, respectively).

CD44, surface glycoprotein, was upregulated 6 fold in hRPCs vs. tissue. CCL2 chemokine (MCP-1) was strongly upregulated (68-105 fold) in hRPCs vs. tissue. CXCL12 (SDF-1) is the ligand for the (nonspecific) hRPC surface marker CXCR4. SDF-1 is downregulated compared to hFBs, so expression is low (as we know from ELISA), however, it is elevated 4-12 fold in hRPCs vs. tissue. CXCR4 is a surface marker of hRPCs and was clearly upregulated in hRPCs vs. hFB. Comparison to tissue was interesting in that normoxic MCB was lower than tissue, but the hypoxic cells similar. This confirms that both hRPC conditions express CXCR4, with hypoxic expressing more, and retinal tissue similar to hypoxic cells.

IL-11 and IL-18 were upregulated vs tissue. IL-1A (IL-la) was upregulated vs. tissue, although "not" for hypoxic MCB. A number of IL receptors were upregulated vs. tissue, most prominently IL-7R (60-105 fold), IL-31RA (28-80 fold), and IL-4R (18-40 fold). These all represent potential positive markers for hRPCs vs tissue of origin.

WNT pathway genes upregulated vs tissue included some previously identified by qPCr, including WNT7B, and SFRP4. Also upregulated in hRPCs vs tissue were DKK2, FZD6 SFRP1, WNT5A. WIF1 was strongly upregulated vs hFB (for hypoxic), yet strongly downregulated vs tissue (for normox). Notch pathway genes were downregulated or unchanged vs tissue except Jag1, which is candidate hRPC trophic marker, which was upregulated (8-13 fold). The most strongly downregulated were DLL4 and HEYL.

JAK-STAT genes were moderately but uniformly downregulated vs hFB (2-5 fold), except STAT3 which was unchanged for hypoxic vs. FB. They were unchanged vs. tissue. Apoptosis genes were mixed. Most elevated vs. tissue was GADD45B. More prominently GADD45G and DAPL1 were downregulated (20-56 fold). BMP2 (candidate) was upregulated vs hFB, but no change seen vs. tissue. Other BMPs were generally decreased vs. FB and also unchanged vs. tissue. TGF beta genes were unchanged throughout.

HIF1A (HIF1alpha) was moderately decreased vs. tissue (4 fold). Neuropilin 1 and especially 2 appear to be increased (except for hypoxic MCB). RICTOR was modestly decreased vs. tissue (2 fold). Toll-like receptors 3-7 and 9 were unchanged vs. tissue. DCX was strongly downregulated vs. tissue, as were a number of other neural markers to a lesser degree, the next most being NRXN1 (neurexin1, >25 fold). GFAP was clearly upregulated vs. hFB, less clearly vs. fetal retinal tissue. A large number of retina-associated genes are strongly downregulated by hRPCs vs. fetal retinal tissue of origin. These include CRX, EYS, IMPG1,2; NRL, recoverin, RGR, RP1, and VSX1, 2. Of 98 small non-coding RNAs (SNORDs) examined, almost all were downregulated vs. tissue, sometimes massively, except 114-6, 49B, 75, and 78, with 114-2, 44, 49A, 74, 79, 96A being suggestive but somewhat inconsistent across conditions. Regardless, upregulation was not to a high level.

In summary, the data indicates that CTGF is an hRPC marker and may be helpful to determine the trophic mechanism underlying therapeutic efficacy. Other such markers include SPP1 (OPN), PTN, LIF, FGF9, JAG1, IL-1A, IL-11, IL-18, and noggin. NTRK2 neurotrophin receptor is a hRPC surface marker, as are the interleukin receptors IL7R, IL-31RA, and IL-4R. Notably, HGF appears to have potential as a negative marker for hRPCs, or alternatively, in a method for detecting contaminating cell types. Downregulation of the ocular transcription factors DACH1, OTX2, CRX, NRL, VSX1,2 and differentiation transcription factors NeuroD1 (and 4), the post-mitotic blast marker doublecortin (DCX), synaptic marker DLG2, many notch pathway genes, neurexin1, as well as the mature retinal markers recoverin and interphotoreceptor matrix genes IMPG1,2 are also useful to distinguish cultured hRPCs from tissue of origin. Cells expressing those markers are more specified, mature, and less proliferative and therefore far less plentiful than in proliferative hRPC cultures. CPA4 is highly upregulated, while PAR4 and a long list of SNORDs are downregulated.

Figure 40:
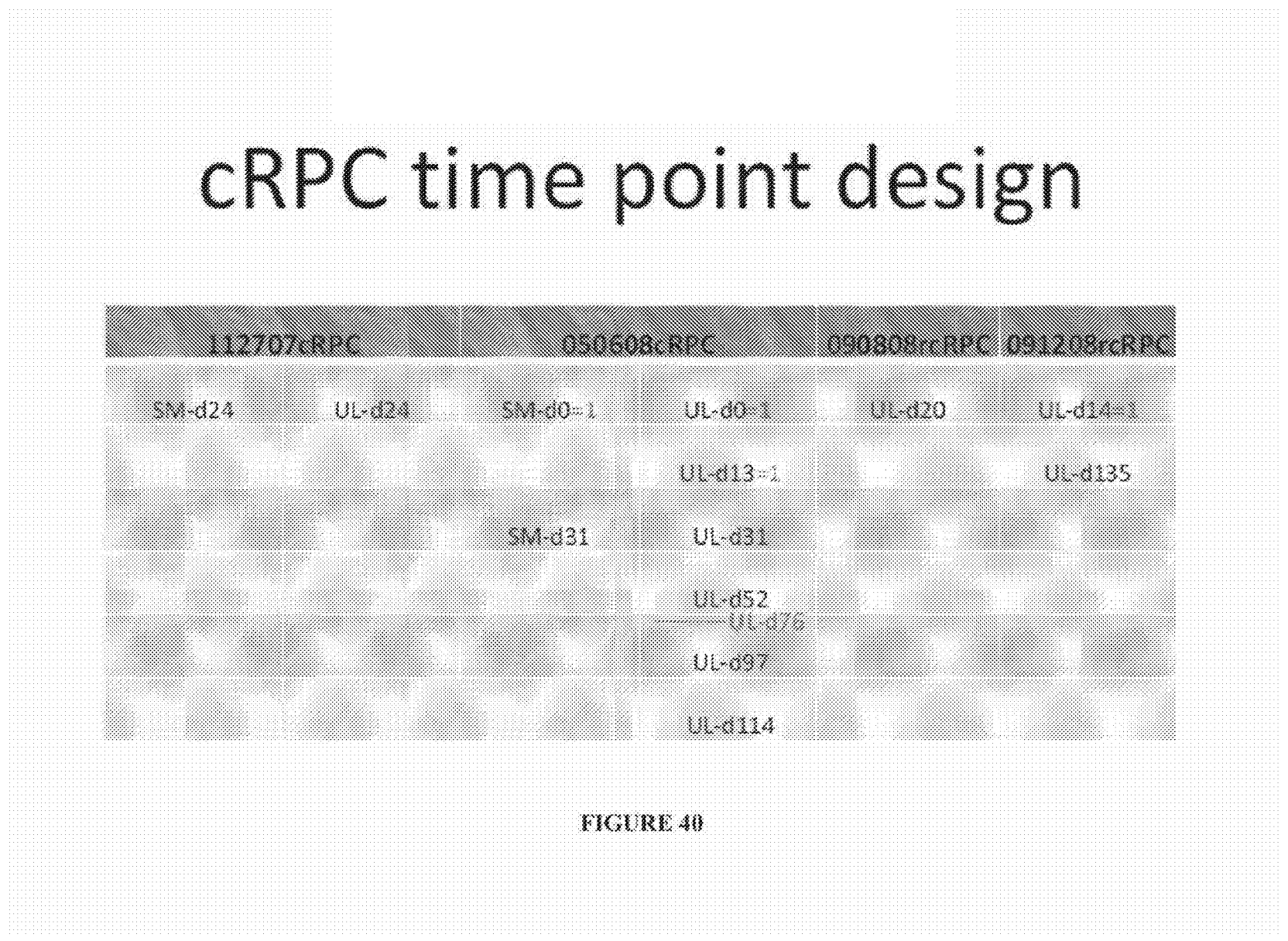
Figure 45:
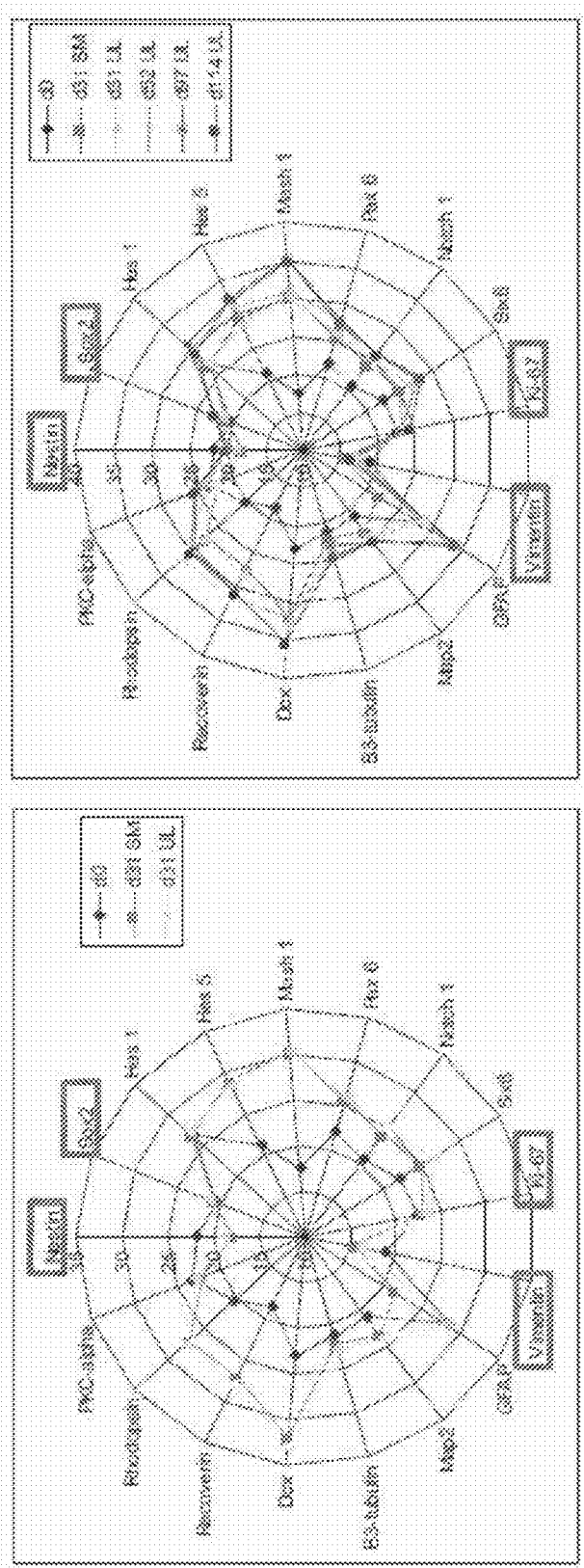
FIG. 45 is a radial graph showing changes in the expression pattern of feline cRPCs by time point and culture conditions.
Figure 46:
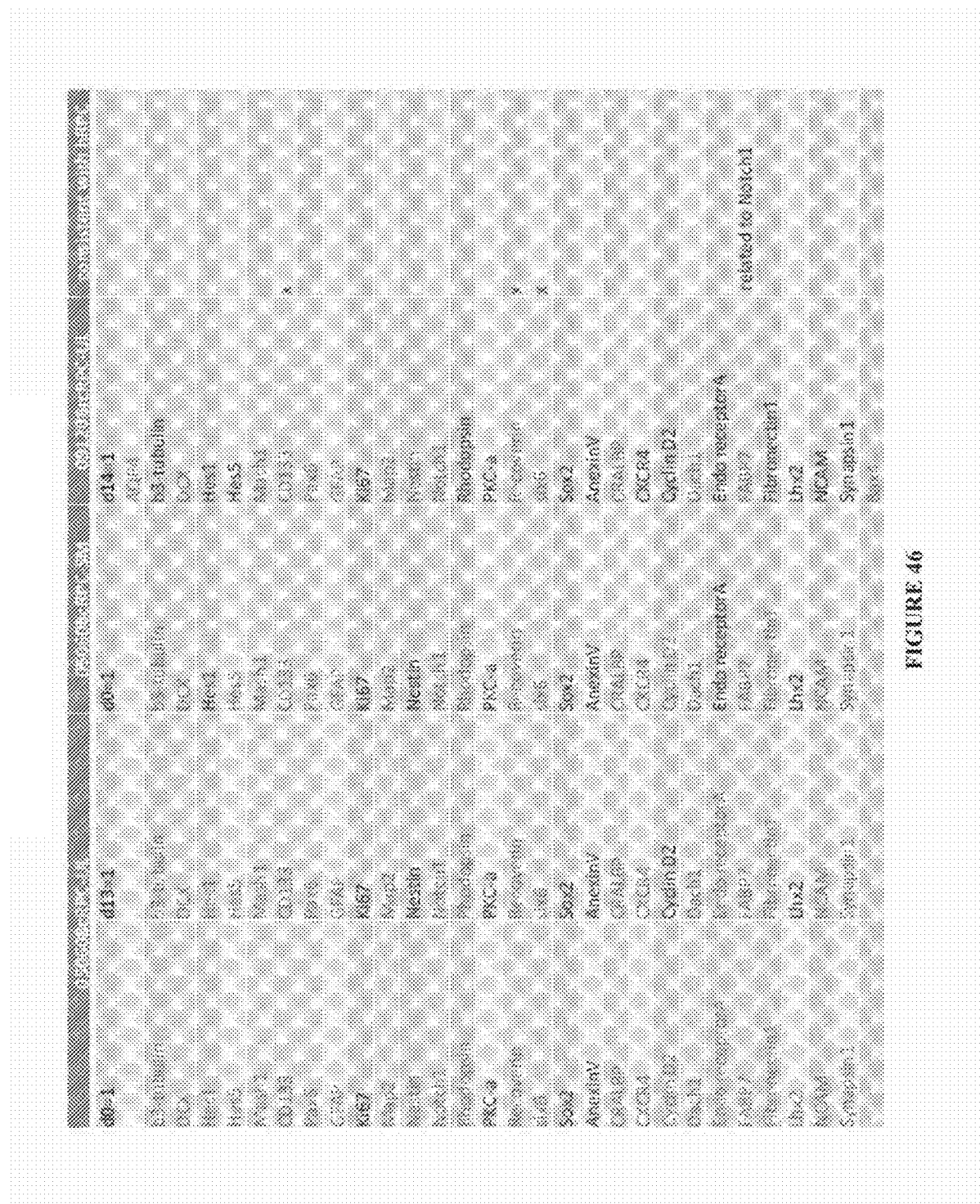
FIG. 46 is a chart summarizing qPCR data obtained from feline RPCs across different donations and culture conditions.

Similar data was obtained for feline RPCs. In FIG. 40, a tabular summary of experiments testing cell culture conditions over time is provided. FIGS. 41-44 show the results of an experiment measuring gene expression in feline RPCs by qPCR in UL media at the various time points. Notably, in UL media, the tested markers were downregulated, with the progenitor markers nestin and vimentin showing elevated expression over Day 0 baseline. Cyclin D2 is elevated in UL at time points after Day 0 baseline. The pattern of changes in expression within the tested profiles for feline cRPCs is presented as a radial graph in FIG. 45. Genes having high copy number are toward the center of the graphs, while genes having lower expression are peripheral. Progenitor markers are listed from nestin at 12 o'clock clockwise (on the radial graph) to vimentin at about 6:30. Lineage markers are also shown. Note that expression tends to be highest across markers at Day 0 (dark blue) and decrease for some, but not all, markers with time. The biggest decrease in expression appears to occur in going from Day 0 to the first time point in culture measured (Day 31). Decreased expression is seen in a subset of both lineage and progenitor markers. A chart summarizing the expression data for feline RPCs is presented in FIG. 46, representing qPCR data across different donors and culture conditions.

An enzyme-linked immunosorbent assay (ELISA) was carried out for the purpose of characterizing hRPCs and potential mechanism of action (i.e., neuroprotection). These studies were performed by either multiplex assay or sandwich ELISA. For multiplex ELISA assay, Assay Buffer was added to a 96 well filter plate and the plate placed on a shaker for 10 minutes. The plate was then cleared by vacuum and 25 μl of Assay Buffer or other appropriate buffer added to each well with 25 μl of standard/sample/control added to the appropriate wells. Then 25 μl of a mixture containing requested cytokines (1:50 dilution) that were conjugated to beads was added. The plate was then placed on a shaker, at 4° C. overnight. The plate was then washed 3 times. Detection antibody was added and the plate placed on a shaker for one hour at room temperature. Then 25 μl of Phycoerythrin (1:25 dilution) was added to each well on the shaker for 30 minutes. The plate was then washed three times and 150 μl of Sheath Fluid is added to each well. The plate was then read using a Luminex 100 reader and Softmax Pro software. The data was calculated using Millipore's BeadLyte Software.

For sandwich ELISA, markers were measured by two-antibody ELISA using biotin-strepavidin-peroxidase detection. Polystyrene plates were coated with capture antibody overnight at 25° C. The plates were washed 4 times with 50 mM Tris, 0.2% Tween-20, pH 7.0-7.5, and then blocked for 90 minutes at 25° C. with assay buffer. The plates were washed 4 times and 50 μl assay buffer was added to each well, along with 50 μl of sample or standard prepared in assay buffer. The plates were then incubated at 37° C. for 2 hours. The plates were washed 4 times and 100 μl of biotinylated detecting antibody in assay buffer was added and incubated for 1 hour at 25° C. After washing the plates 4 times, strepavidin-peroxidase polymer in casein buffer (RDI) was added and incubated at 25° C. for 30 minutes. The plates were washed 4 times and 100 μl of commercially prepared substrate (TMB; Neogen) was added and incubated at 25° C. for approximately 10-30 minutes. The reaction was stopped with 100 μl 2N HCl and the A450 (minus A650) was read on a microplate reader (Molecular Dynamics). A curve was fit to the standards using a computer program (SoftPro; Molecular Dynamics) and cytokine concentration in each sample was calculated from the standard curve equation. Data reflects protein secretion from averaged samples. Expression of five candidate trophic factors, GDNF, BDNF, VEGF, OPN, and SDF-1, was evaluated under standard normoxic (20% $O_2$) as well as low oxygen (3% $O_2$) conditions.

Figure 47:
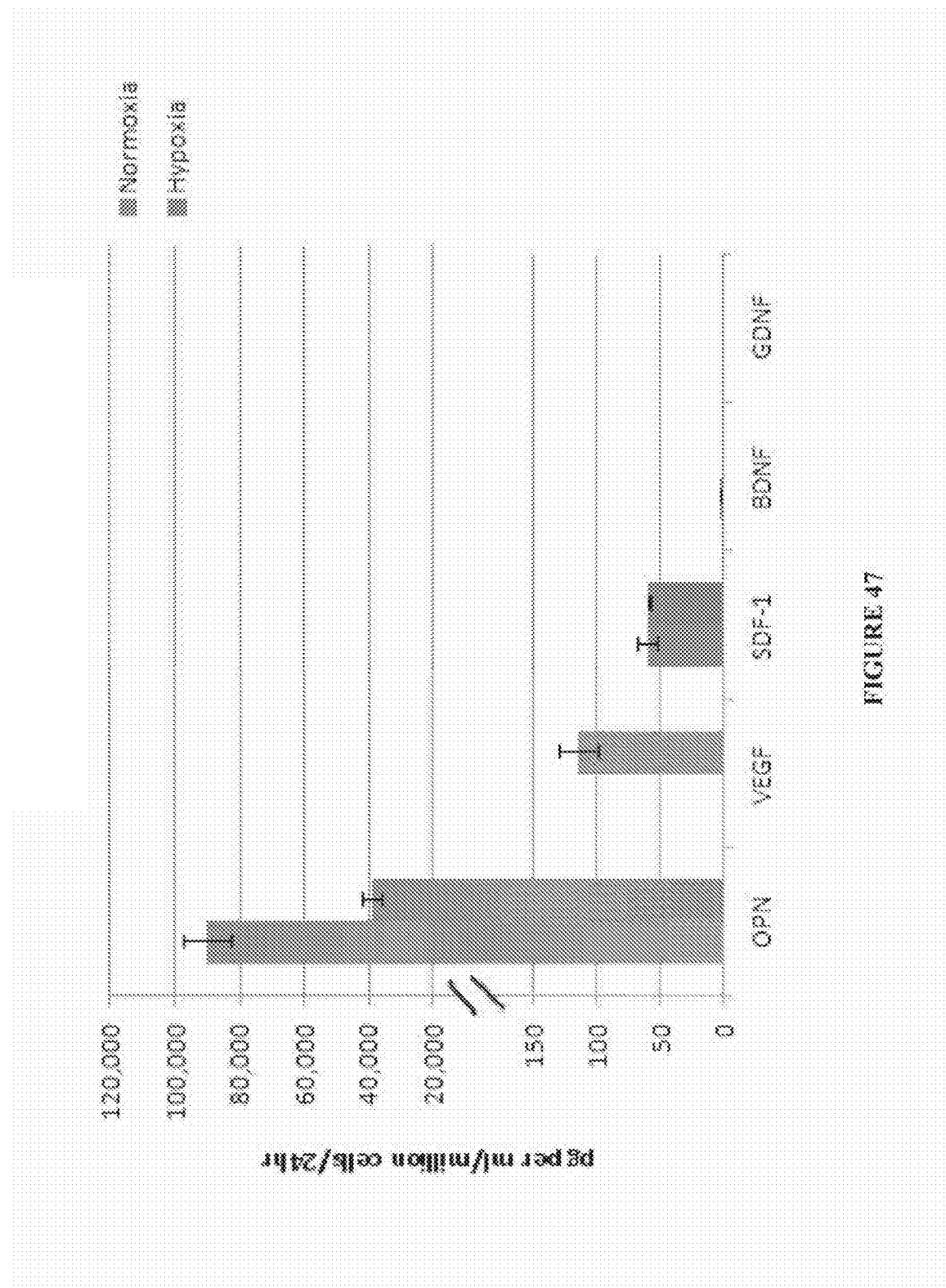
FIG. 47 shows the results of an ELISA test characterizing hRPCs cultured under normoxic and hypoxic conditions. Markers detected include OPN, VEGF, SDF-1, BDNF, and GDNF.

In FIG. 47, GDNF expression was found to be undetectable at level of secreted protein (<0.1 picogram/ml). BDNF expression was out of range (OOR) to the low side, but just detectable at average concentration of 1.58 pg/ml for normoxic conditions and 0.55 pg/ml for hypoxic conditions. VEGF was OOR to low side for the normoxic (20% $O_2$) condition, but detectable for hypoxic (3% $O_2$) at average concentration of 92 pg/ml. OPN (osteopontin, SPP1) expression was strongly positive (nanogram range instead of picogram) under both conditions, approximately double for norm ox versus low ox (average=72.2 ng/ml vs 31.3 ng/ml, respectively). Those are notable levels in both instances and suggest a role for this known neuroprotective/anti-apoptotic factor. SDF-1 (stromal cell-derived factor 1) was OOR to the low side, but detectable with average concentration of approx 48 pg/ml for both norm ox and low ox cultures.

Osteopontin (OPN, SPP1) is highly expressed by hRPCs and secreted into the surrounding media at what are predicted to be physiologically significant concentrations. Other expression data showed differential expression of this gene versus other cell types. Taken together, these data suggest that OPN could play a role in the neuroprotective/cone-reactivating effects of hRPCs. The other factors tested are less likely to play such a role (unless they happen to be massively upregulated following transplantation in response to the microenvironment of the vitreous/degenerative retina, which is less likely).

Fluorescence-activated cell sorting was carried out to characterize hRPCs and defining the extent of marker expression within the population. Cultured cells or dissociated retinal single cells are stained by either conjugated surface antibody marker/isotype control (BD) or fixed and permeabilized, followed by conjugated intracellular antibody marker/isotype control (BD) staining for 30 min at room temperature. After washing in stain buffer (BD) 3 times, cells were run by BD Aria II Sorter. Data were obtained from same 3 simultaneous fetal eye donations used for the microarray studies.

FIG. 48 shows expression of 10 markers, either lineage related or potentially relevant surface or genetic markers in retinal tissue at Day 0 compared to cultured hRPCs grown under normoxic (20%) conditions or low oxygen (3%) conditions. The data show differences between retinal tissue of origin and cultured RPCs, particularly massive upregulation of MHC class I, accompanied by large increase in Fas (CD95), but not MHC class II. GFAP is low but increased, to a lesser degree. Other markers change in varying degrees.

Example 3

In Vivo Efficacy of RPCs

RPCs were prepared for transplantation by first harvesting them with TrypLE Express and collecting them by centrifugation at 1000 rpm for 5 minutes. Cells were washed once in HBSS, and then resuspended in cold HBSS to determine cell viability and cell number. For human transplantation, $0.5 \times 10^6$ cells in 100 μl HBSS were used. For transplantation into rats, varying doses ranging from 4000 to 75,000 cells in 2 μl HBSS were used.

Human RPCs were transplanted as a suspension to the vitreous or subretinal space of dystrophic hooded RCS rats. Rats were maintained on cyclosporin A and steroids to avoid rejection of xenografts. Control eyes received sham injections (subretinal, intravitreal) consisting of vehicle alone. Grafted animals were tested functionally in the unrestrained waking state using a commercial apparatus designed for quantification of the optomotor response (OR). A subset of animals was tested for luminance threshold across the visual field. This was done by electrophysiology via extracellular recordings in the contralateral superior colliculus. At the end of the study, eyes were collected, fixed, and analyzed histologically for evidence of host photoreceptor rescue and donor cell survival.

Figure 49:
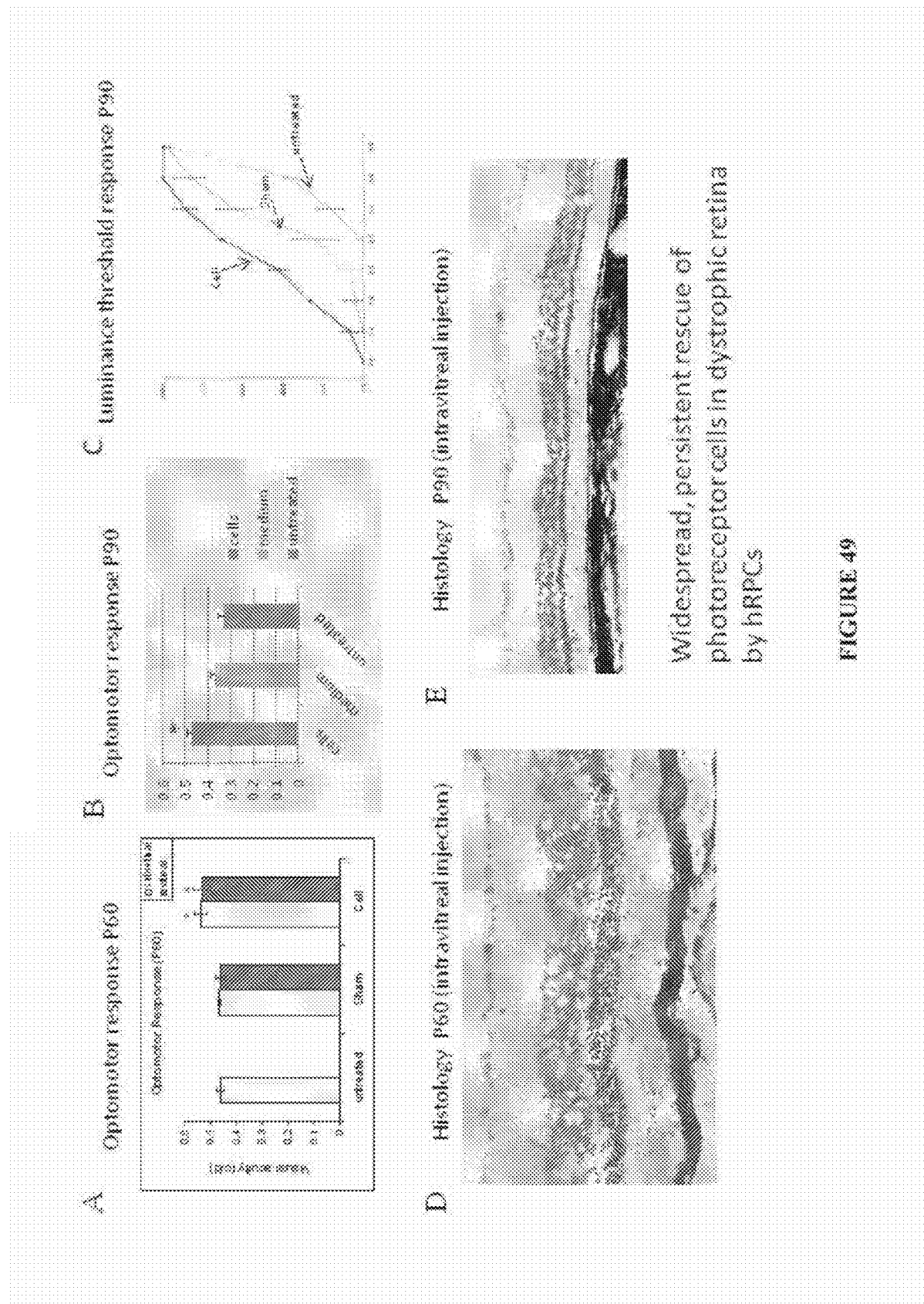
FIG. 49 illustrates proof of concept of methods of the invention using in vivo transplantation of hRPCs into the eyes of dystrophic RCS rats in a model of a hereditary photoreceptor degeneration.
Figure 50:
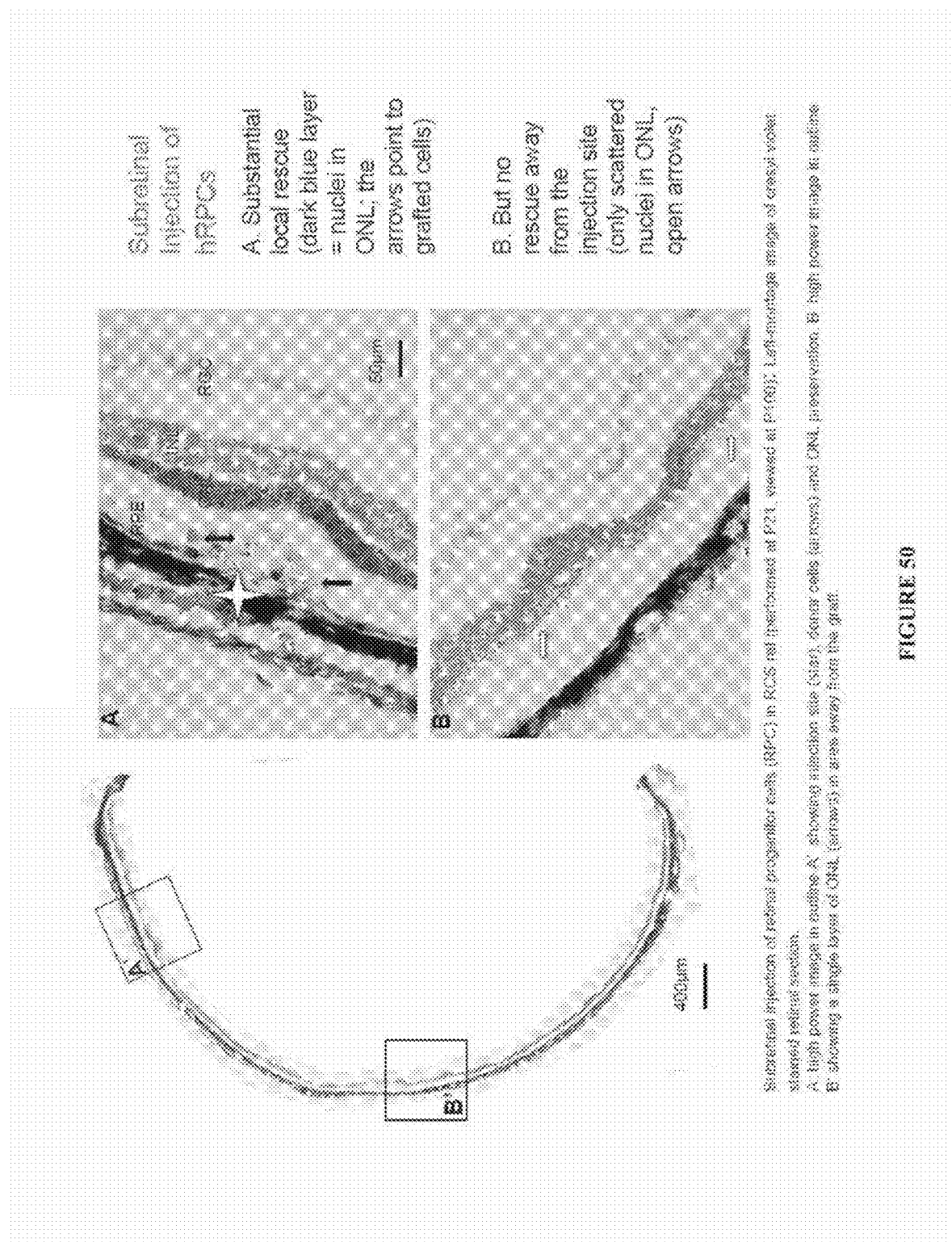
FIGS. 50 and 51 are photographs showing staining of rat retinas after subretinal injection of hRPCs.
Figure 51:
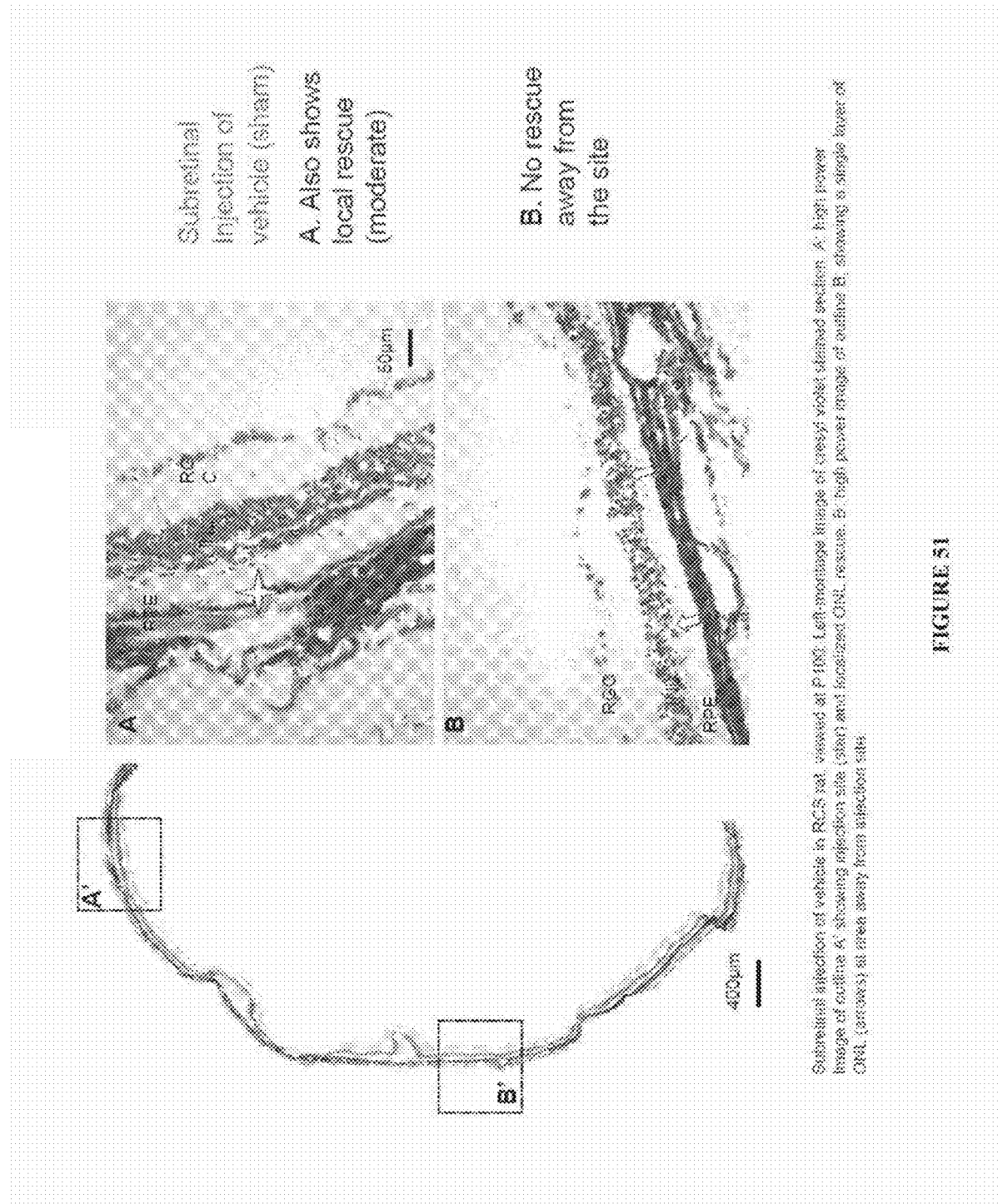
Figure 52:
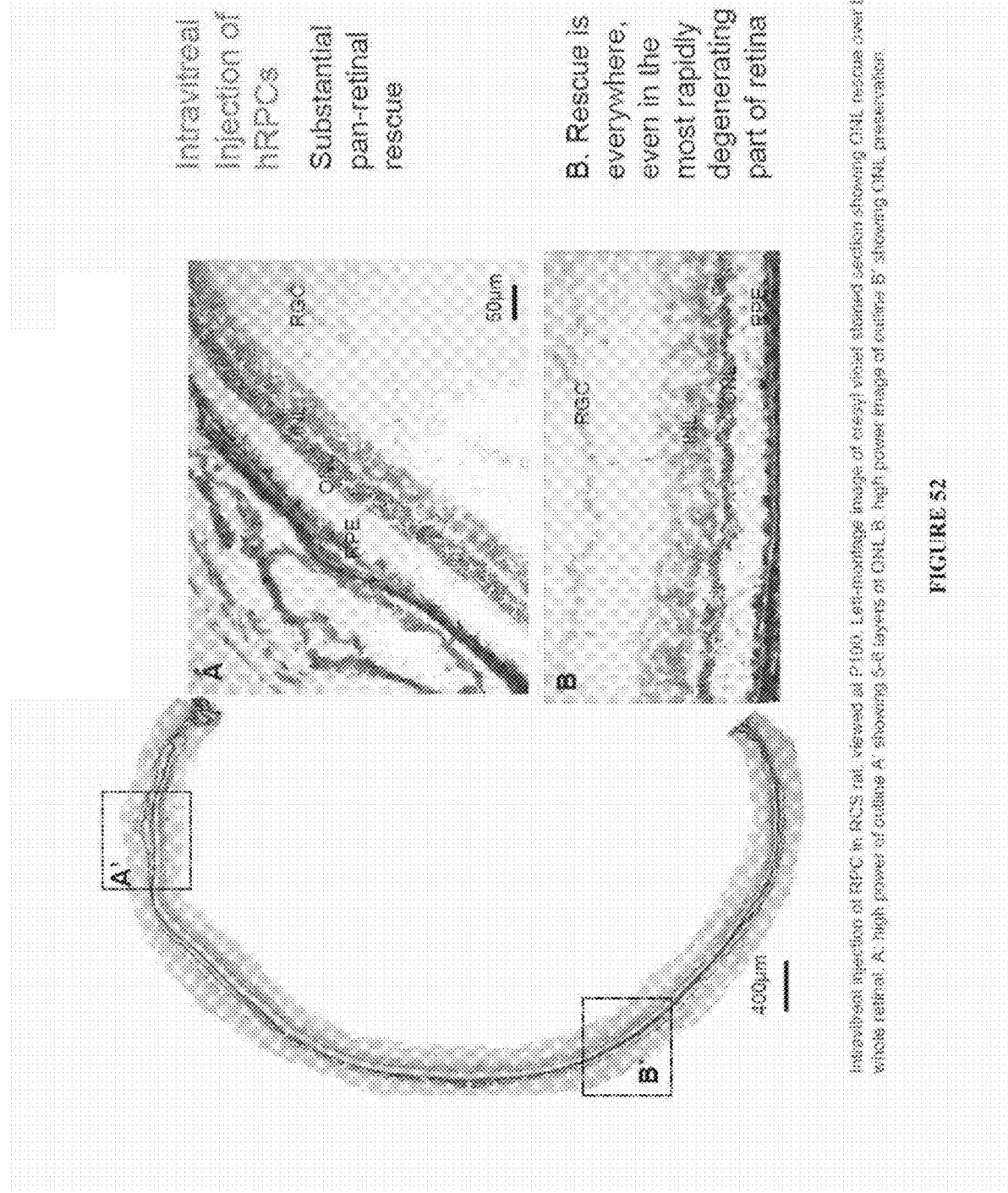
FIGS. 52 and 53 are photographs showing staining of rat retinas after intravitreal injection of hRPCs.
Figure 53:
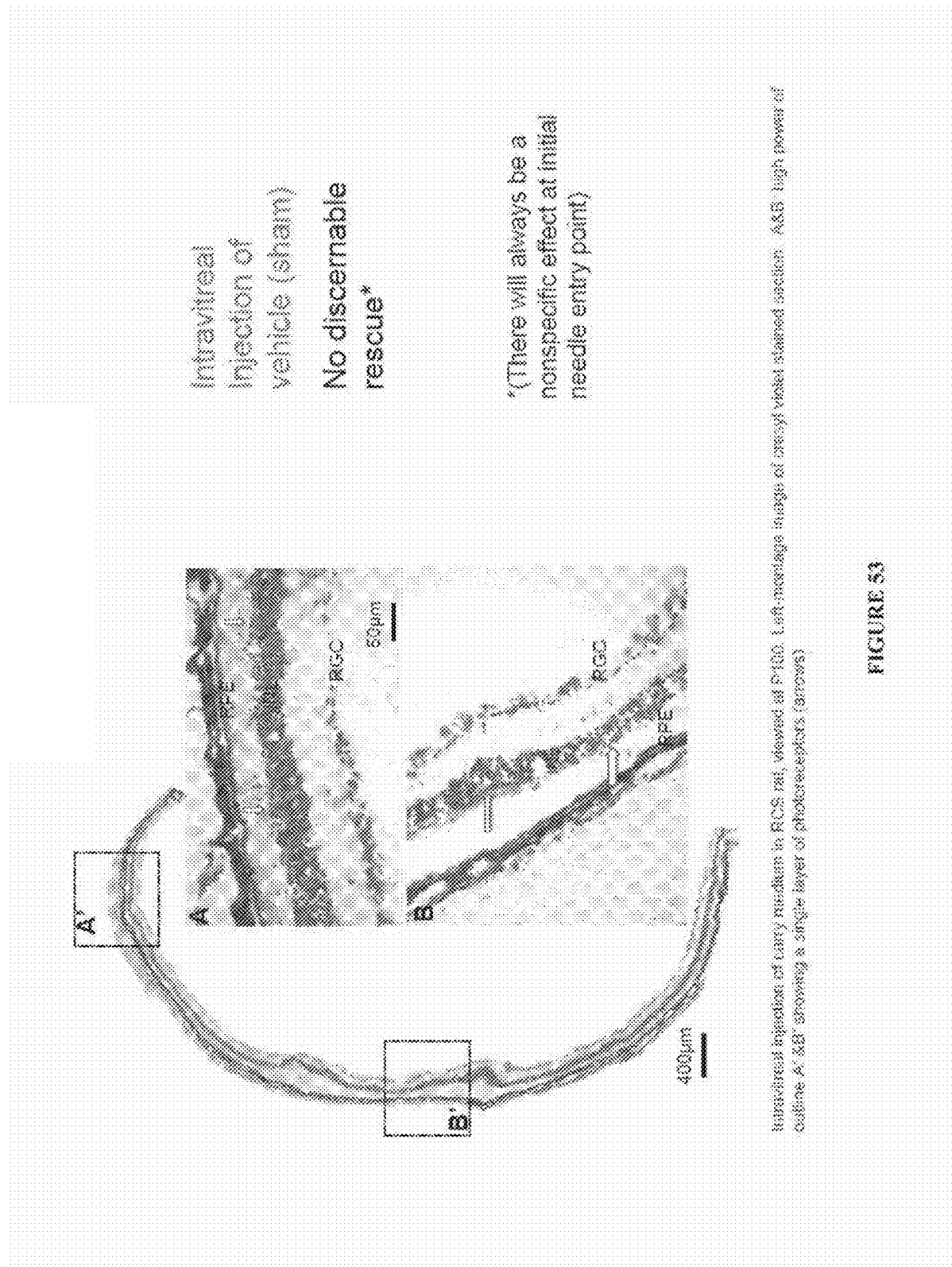
Figure 54:
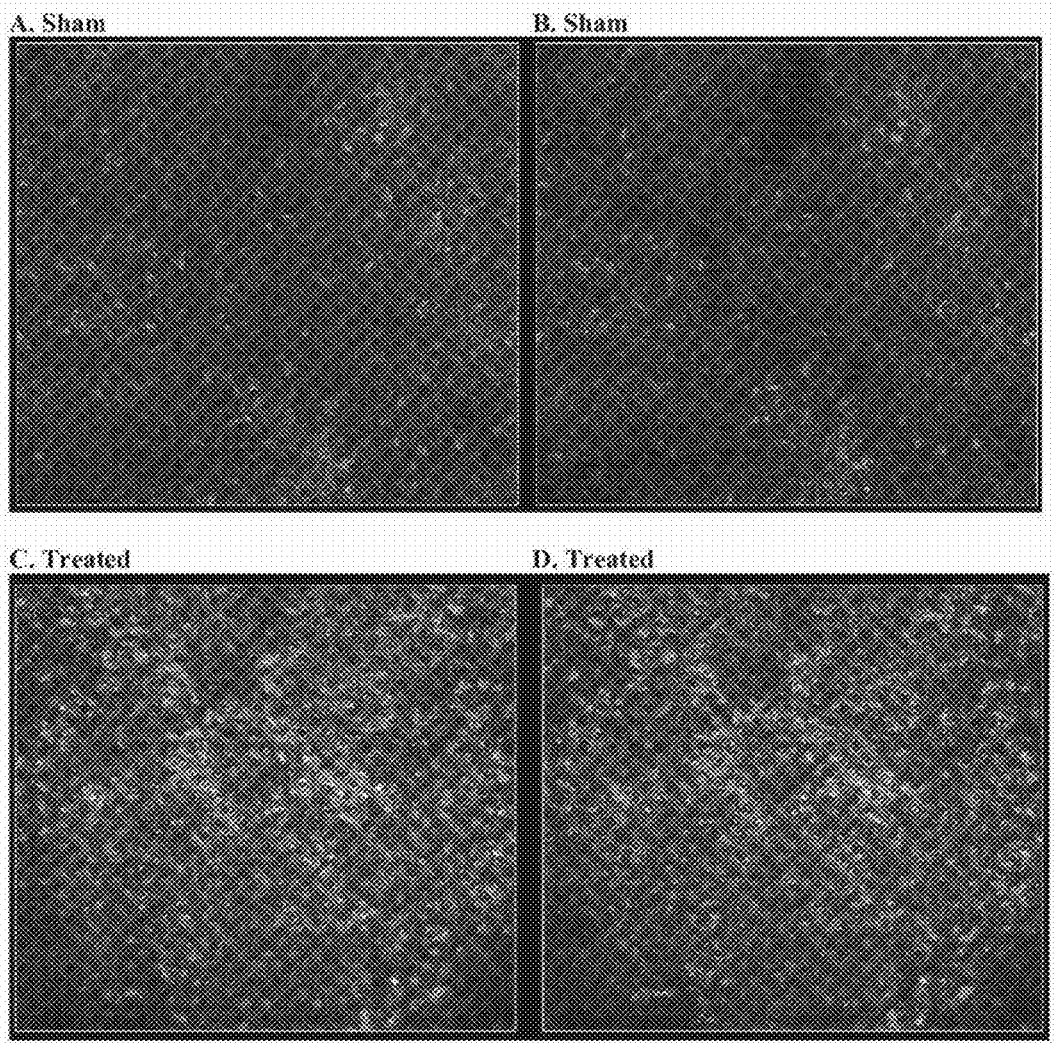
FIG. 54 are photographs showing immunocytochemical staining of RCS whole mounts after injection of hRPCs in rat retinas. A and B: sham; C and D: treated.
Figure 55:
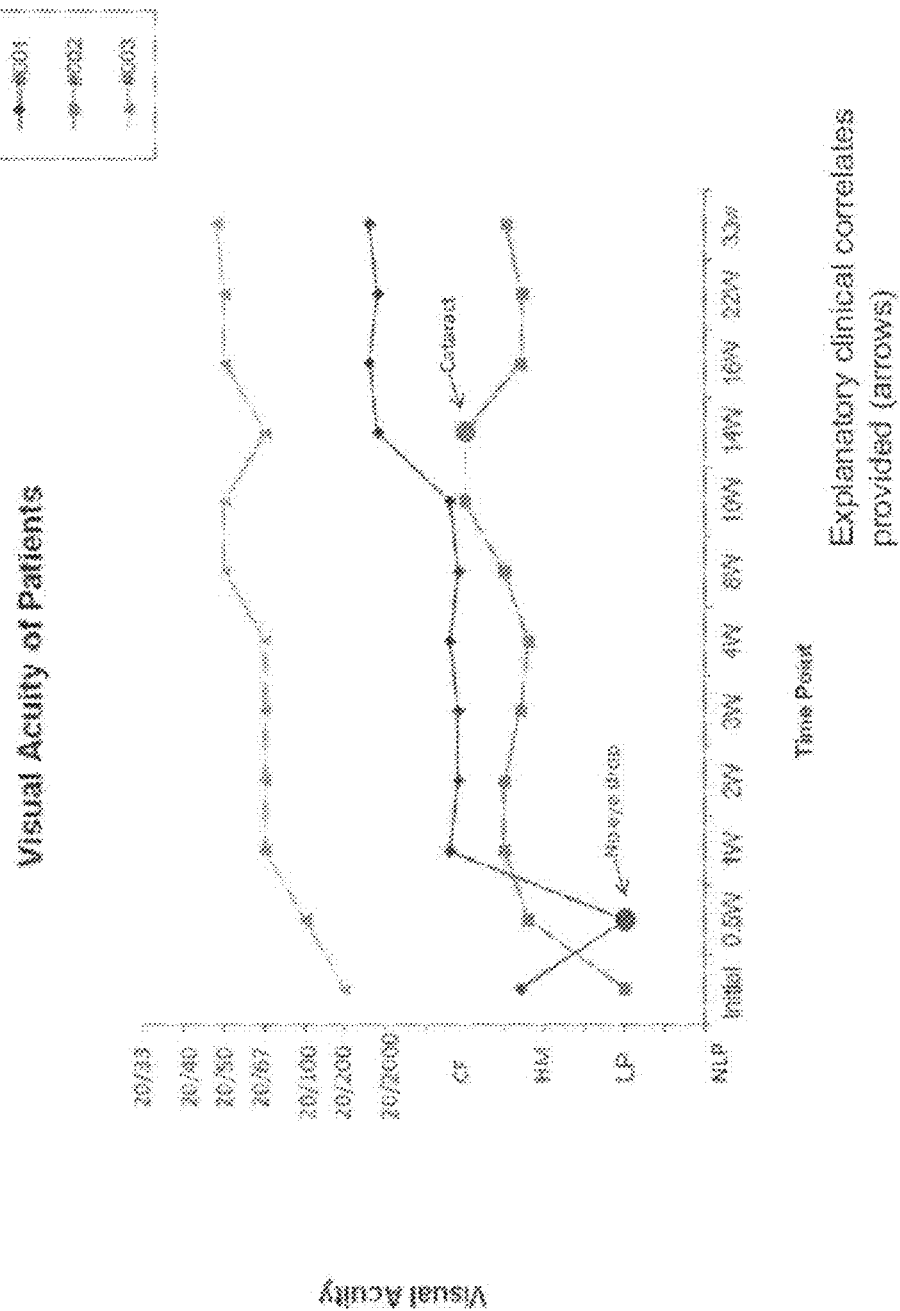
FIG. 55 is a graph showing improvements in visual acuity in patients receiving treatment with hRPCs.

FIG. 49 illustrates proof of concept of methods of the invention using in vivo transplantation: hRPCs (or vehicle alone, "sham") were injected to the eyes of dystrophic RCS rats (model of a hereditary photoreceptor degeneration). Injections were placed in either the vitreous or subretinal space. Animals with hRPC grafts to either location performed significantly better than shams, or untreated controls, at age 60 days. Histology at that time point showed extensive rescue, which was located in the region of the subretinal injection (FIGS. 50-51), or widespread across the retina in the case of intravitreal grafts (FIGS. 52-53). Several cases were further examined for luminance threshold at age 90 days, across the visual field, using electrophysiological recordings in the contralateral superior colliculus. Animals with transplants exhibited significantly improved sensitivity compared to shams or untreated controls. Histology at 90 days showed persistent high level rescue of host photoreceptors. FIGS. 54-55 show the results of immunocytochemistry performed on RCS whole mounts.

The in vivo data confirm and demonstrate that hRPC transplantation is successful at functional and anatomic levels in a rat model. The data also indicate that intravitreal injection can, in certain circumstances, have advantages over subretinal grafts in terms of the extent of host retina that is rescued. RPCs are also effective when placed subretinally, albeit in a more restricted manner (such restriction in rescue is the case with subretinal placement of most if not all non-malignant cells used by variety of investigators).

Example 4

Clinical Study of hRPC Transplantation in Patients

A prospective, open-label, feasibility study of intraocular injections of RPCs in patients with retinal disease to obtain preliminary safety data was carried out. Cells and tissues were first evaluated for safety prior to commencement of the clinical study. Tissues were sourced from Advanced Bioscience Resources, Inc. (ABR), which is also able to provide GTP level tissue samples which are anticipated to form the basis of establishing a CGMP master cell bank based on this technology. Pathology and blood testing of donor samples for exposure to adventitious agents (e.g., HIV, hepatitis B and C viruses, cytomegalovirus) was carried out and tests for endotoxin, mycoplasma, and fungi, such as the limulus amebocyte lysate (LAL) test (kinetic turbidimetric method) for endotoxin detection and the Fungitell kinetic chromogenic method for detection of fungal contamination or final container sterility test by direct inobulation, were performed on cultured donor samples. Cell culture medium was collected and measured in our lab or mycoplasma core service using LookOut Mycoplasma PCR Detection Kit (Sigma) or MycoAlert mycoplasma detection kit (Lonza). Cultured donor samples were also subjected to a soft agar assay to test for tumorigenic potential. Cell suspensions of either $0.2 \times 10^5$ or $1.0 \times 10^5$ cells from different donations and different time points were seeded into growth medium containing 0.35% agar and then overlaid onto 0.7% agar gel. After incubation for 28 days, colonies were stained with 0.005% crystal violet and scored for growth relative to positive and negative controls. Cells for transplantation were also subjected to a test for telomerase activity. One microgram of cell protein from different donations and different time points in culture were tested using TRAPEZE RT Telomerase Detection Kit (Chemicon) with TITANIUM Taq DNA Polymerase (BD Clontech), according to manufacturer's instructions. In addition, cells were karyotyped by a third-party company to detect for the presence of any abnormalities, as they can be indicative of spontaneous immortalization and cancerous behavior of cultured progenitor cells. Finally, cell viability and cell number were determined by Trypan blue (Invitrogen) staining, counted by Countess automated cell counter (Invitrogen) or manually using a hemocytometer (Fisher Scientific).

Clinical lab results indicated that blood samples from donors were negative for lethal viruses and other adventitious agents. Cells for transplantation were negative for endotoxin, mycoplasma, and fungal infection as well. In addition, cells prepared for transplant did not form colonies in soft agar, indicating their lack of tumorigenicity. Karyotype analysis was also performed to ensure clinical safety of cultured hRPCs (was outsourced to established FDA-respected vendor, Cell Line Genetics). Karyotyping revealed no abnormalities either. With regard for cell viability and cell number, harvested cells were left in transplantation medium on ice out of incubator for various lengths of time. A subset was also expelled through a 27 g hypodermic needle to evaluate the effect of that on survival. Expulsion through hypodermic had no detectible effect. The anticipated actual procedure time is less than 1 hour. Survival outside incubator began to drop appreciably at 2.5 hr, but remained greater than 90% (acceptable) out to 3.5 hours. This suggested that the clinical transplantation procedure would not have a major effect on donor cell survival.

Cells prepared for transplantation exhibit low or moderate, but not elevated levels of telomerase activity. Telomerase activity is typically down-regulated in mammalian cells beyond early embryonic development, except in certain cells including those of the germline which must be effectively immortal and transmitted indefinitely. The normal loss of telomerase activity is associated with both a limited lifespan for the organism, but also indicates low probability of tumorigenicity. Increased telomerase activity is seen in mammalian cancer cells and pluripotent stem cells and immortalized human cells in culture. The strong association with malignant activity means that it is potentially dangerous to transplant cells with elevated telomerase levels. The safety tests indicate that the conditions to prepare cells for transplantation do not induce elevated telomerase activity, over a range of time points in culture out to 97 days (i.e., beyond current usable limit). In fact, telomerase activity tends to drop off with time, consistent with developmental "senescence". In other words, the cells eventually become senescent and lose the ability to proliferate.

Eligible patients received one unilateral injection of cells. Eligibility was determined by selecting for patients having any one of severe end stage retinal or optic nerve disease, poor residual central visual acuity of 20/200 or less with the use of a correcting lens, and/or dismal vision prognosis. Patients also must have adequate pupil dilation and clear ocular media to permit stereoscopic fundus photography, intraocular pressure of 21 mm Hg or less and open anterior chamber angle. Patients were excluded if they exhibited narrow anterior chamber angle, anterior chamber synechia or neovascularization, a history of angle closure glaucoma, significant existing media opacities that would obstruct view during treatment, fundus examination, measurement of visual acuity, general evaluation of toxicity, any intraocular surgery in the same eye within three months prior to study entry; having known serious allergies to fluorescein dye used for angiography; a prior history or evidence of severe cardiac disease (NYHA Functional Class III or IV), myocardial infarction within six months, or ventricular tachyarrhythmias requiring continuing treatment, or unstable angina.

Three legally blind patients with retinal disease (i.e., retinitis pigmentosa) and visual acuity no greater than 20/200 with a poor prognosis for improvement in vision were selected. Enrolled patients ranged in age from 46 to 57, two female, one male, all them with the diagnosis of RP. Two had IOL, one had a cataract.

Early passage fetal human retinal progenitor cells were characterized by transcript and protein expression profiles and tested for normal karyotype. The cells were also negative for fungi, bacteria (endotoxin), mycoplasma. Tissues were also screened for adventitious viruses and were found to be negative for HIV1 and HIV2 antibodies, Hepatitis B antigens, Hepatitis C antibodies, syphilis, Herpes simplex virus IgM antibodies, West Nile Virus TMA:singlet, and EBV IgM VCA antibodies. Cells were prepared for intravitral bolus injection at a dose of 100 µl cell suspension (which delivered approximately 0.5 million cells to the eye).

For three days, the patients were self-treated with topical antibiotic drop at home prior to Day 0. On Day 0, patients were subjected to a baseline clinical examination, including fundus photography. Eyes were irrigated and administered topical antibiotics, then pupils were dilated and topical anesthesic drops applied. Awake, non-sedated patients were injected once with cells through the wall of the globe at the level of the "surgical limbus" into the vitreal cavity, using a standard angled-entry approach to create self-sealing entry passage and avoid reflux of graft under direct visualization by surgical microscope under sterile operative conditions. An anterior chamber paracentesis was performed to prevent iatrogenic elevation of intraocular pressure. No immunosuppressive therapy, sutures, or wound closure procedure were involved. Post-injection antibiotics were administered thereafter and intraocular pressure carefully monitored. All patients were discharged same day, with accompanying person and no hospital stay was required. Patients were advised to keep their heads elevated post-injection at least 45 degrees for at least 2 hours, to avoid cellular bolus settling over the macula. Prior to discharge from hospital, patients were instructed to sleep at home with their heads slightly elevated for 2-3 days post-injection.

Clinical follow-ups were scheduled 1 day, 3 days, 1 week, 1 month, 2 months, 3 months, 6 months, 1 year, and annually for 5 years after treatment. Incidence and severity of ocular adverse events were identified by standard ophthalmic examination techniques, including fundus examination, best corrected visual acuity (BCVA), IOP, slit lamp examination, fluorescein angiography (FA), Optical Coherence Tomography (OCT), stereo-fundus photography, and cone flicker electroetinography (ERG) response.

Follow up slit lamp examination of all patients revealed that cells of graft can be visualized in the vitreous, some congealing into strands-like structures, confirming that the transplanted cells had entered eye and stayed there, and that vitreous placement resulted in a collection of vitreal cells. Notably, this did not negate visual improvement due to obscuration of visual axis (blocking subjects view out of the eye) as might theoretically occur.

A follow up B Scan was carried out, wherein an ultrasound device followed vitreal cells at 4 months post-operation. Results show no tumor formation in the eye and no tumor formation in the anterior orbit (behind the eye). The persistence of grafted cells (and persistence of visual improvements) suggests that there is no need for routine immune suppression in patients receiving the transplanted cells. No evidence of tumors, vascular complications or retinal detachment was seen either on examination or by fundus photography. Notably, no patient experienced loss of vision due to procedure and all patients reported detectable improvement in vision. Improvements were related to severity of disease: the worse the initial vision, the more limited the improvement, while the better the initial vision, the greater and more rapid the improvement. One patient (002) with hand motion vision was able to see the eye chart again at 4 months. Another patient (003) regained central fixation and a degree of macular function (which is needed to achieve visual acuity better than 20/200). Patient 003 achieved an improvement in visual acuity of "20 letters" on the eye chart, which is a very large and significant improvement. Visual improvements were sustained and acuity gains persisted to at least 1.5 years. Patients also reported better visual function in general and improved activities of daily living.

The results of the visual acuity test as used for comparison of trend between patients is provided in FIG. 55. Neither scale is precisely linear. Evidence of rapid improvement in vision was observed within the $1^{st}$ week in all three cases, most consistent with a clinically significant trophic effect on host retina. Also, tendency toward additional improvements were seen after 1 month, which may include engraftment and retina cell replacement. Some issues with the patients correspond to certain obvious deflections in the data trends. Patient 002 (blue) was non-compliant with post-operative drops and developed an anterior uveitis that rapidly resolved with standard post-op medications. Notably, her long-term progress shows improvement. Patient 001 (pink) had a pre-existing cataract which worsened over the first few months post-transplantation, perhaps due to the procedure, and that may have related to her secondary decline of vision (although vision was improved over the initial level). No abnormalities of IOP were found to be associated with transplantation of hRPCs (See Table 1).

TABLE 1

Intraocular Pressures of Study Eyes

| | Intraocular Pressure (mm Hg) | |
|---|---|---|
| Patient No. | Initial | Final |
| 001 | Normal | Normal |
| 002 | Normal | Normal |
| 003 | Normal | Normal |

In a visual field test, all 3 patients had lost central fixation prior to treatment because of poor visual acuity associated with loss of macular function due to end stage retinitis pigmentosa. Patient 003 regained central fixation at day 3, and was able to perform automated visual field testing which revealed a small 2-degree area with 20 DB sensitivity (normal). Visual sensitivity in this patient was also elevated in another area nasal to the foveal fixation point. Since this patient regained central fixation, it was possible to test his visual field using automated perimetry (HVF). This test showed that he had regained a small, but highly sensitive island of vision in the central foveal region. Data supports the concept that this treatment involves a rapid trophic effect from the grafted cells, distributed to the retina through the vitreous body, and which appears to restore function to residual host cones. Reports of improved night vision (multiple patients) and improved ERG performance (patient 003) support a role for improved rod photoreceptor function as well. These improvements may also be due to functional cellular integration into the host retina. Other retinal exams such as retina topography, RNFL, OCT, and others were performed. No evidence of tumor formation or immunological tissue rejection were seen.

In summary, all patients in the clinical trial experienced improved visual acuity with treatment. Visual benefits persisted for at least 20 months post-injection. At least one patient had improved visual field characterized by a return of central fixation. No surgical complications or evidence of immune rejection were observed, despite the lack of immune suppression or administration of immunosuppressant drugs. No significant donor cell proliferation was seen in vivo, based on all clinical examinations, i.e., slitlamp, indirect ophthalmoscopy, ultrasound (B scan) of eye and orbit, and fundus photographs. No tumor formation was seen for up to at least 20 months.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

What is claimed is:

1. A method for treating a retinal degeneration in a subject in need thereof comprising administering to the subject an effective amount of a composition comprising non-immortal human fetal retinal progenitor cells,
   wherein the effective amount of the composition comprises between 1000 and 10 million cells per dose and the composition is injected into a vitreous cavity of the subject,
   wherein the composition is prepared by:
      (a) harvesting a sample of cells comprising a plurality of human fetal neural retinal cells from human at about 12 weeks to about 28 weeks gestational age;
      (b) mechanically, enzymatically, or mechanically and enzymatically digesting the harvested sample of cells to make a dissociated suspension of cells and cell clusters; and
      (c) culturing the suspension in serum-free media in culture flasks or plates coated with a xeno-free fibronectin, and ornithine, a polylysine, or a laminin, for between about 10 and 30 passages,
wherein the cells are passaged at between about 40 to 90% confluence and treated with an enzyme at each passage to dissociate the cells and the culture media supplemented with between 0.01 mg/ml and 0.5 mg/ml vitamin C is changed every 1 to 2 days, thereby making non-immortal human retinal progenitor cells and increasing human retinal progenitor cell yield by about 30%,
wherein the non-immortal human retinal progenitor cells express one or more markers selected from the group consisting of nestin, Sox2, Ki-67, MHC Class I, and Fas/CD95,
wherein nestin is expressed by greater than 90% of the cells in the population,
wherein Sox2 is expressed by greater than 80% of the cells in the population,
wherein Ki-67 is expressed by greater than 30% of the cells in the population,
wherein MHC Class I is expressed by greater than 70% of the cells in the population, and
wherein Fas/CD95 is expressed by greater than 30% of the cells in the population,
wherein the injected non-immortal human retinal progenitor cells provide neuroprotective trophic or regenerative influences without integration into the subject,
thereby treating the retinal degeneration.

2. The method of claim 1, wherein the subject is a human or a non-human mammal.

3. The method of claim 1, wherein the retinal degeneration comprises retinitis pigmentosa (RP).

4. The method of claim 1, wherein the cells in the composition further express one or more markers selected from the group consisting of vimentin, CD9, CD81, AQP4, CXCR4, CD15/LeX/SSEA1, GD2 ganglioside, CD133, β3-tubulin, MAP2, GFAP, OPN/SPP1, PTN, KDR, and TEK.

5. The method of claim 1, further comprising measuring changes in vision in the subject after administering to the subject the effective amount of the composition.

6. The method of claim 1, wherein the retinal degeneration comprises Usher's syndrome.

7. The method of claim 1, wherein the retinal degeneration comprises a rod-cone or cone-rod dystrophy.

8. The method of claim 1, wherein the retinal degeneration comprises a ciliopathy.

9. The method of claim 1, wherein the retinal degeneration comprises age related macular degeneration (AMD), wet AMD, or dry AMD.

10. The method of claim 1, wherein the retinal degeneration comprises a retinal photoreceptor disease.

* * * * *